(12) United States Patent
Wissner et al.

(10) Patent No.: US 6,251,912 B1
(45) Date of Patent: Jun. 26, 2001

(54) SUBSTITUTED QUINAZOLINE DERIVATIVES

(75) Inventors: Allan Wissner, Ardsley; Hwei-Ru Tsou, New City; Bernard D. Johnson, Stony Point; Philip R. Hamann, Garnerville; Nan Zhang, Suffern, all of NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/124,365

(22) Filed: Jul. 29, 1998

Related U.S. Application Data

(60) Provisional application No. 60/055,072, filed on Aug. 1, 1997.

(51) Int. Cl.[7] ............... A61K 31/517; C07D 239/88; C07D 239/93; C07D 239/94
(52) U.S. Cl. ............... 514/259; 544/284; 544/278; 544/293
(58) Field of Search ............ 514/259; 544/293, 544/284, 287

(56) References Cited

U.S. PATENT DOCUMENTS

| | | | |
|---|---|---|---|
| 4,343,804 | 8/1982 | Munson et al. | 424/258 |
| 5,475,001 | * 12/1995 | Barker et al. | 514/258 |
| 5,480,883 | 1/1996 | Spada et al. | 514/322 |

FOREIGN PATENT DOCUMENTS

| | | |
|---|---|---|
| 2148324 | 11/1995 | (CA) . |
| 0520722 | 12/1962 | (EP) . |
| 0566226 | 10/1993 | (EP) . |
| 0602851 | 6/1994 | (EP) . |
| 0635498 | 1/1995 | (EP) . |
| 9515758 | 6/1995 | (WO) . |
| 9519774 | 7/1995 | (WO) . |
| 9519970 | 7/1995 | (WO) . |
| 9521613 | 8/1995 | (WO) . |
| 9523141 | 8/1995 | (WO) . |
| 9524190 | 9/1995 | (WO) . |
| 9609294 | 3/1996 | (WO) . |
| 9615118 | 5/1996 | (WO) . |
| 9633978 | 10/1996 | (WO) . |
| 9738983 | 10/1997 | (WO) . |

OTHER PUBLICATIONS

Fry D. et al., Science 265:1093 (1994).
Ife R. et al., J. Med. Chem., 35:3413 (1992).
Maguire M. et al., J. Med. Chem., 37:2129 (1994).
Marecki P. et al., J. Pharm. Sci., 73:1141 (1984).
Rewcastle G. et al., J. Med. Chem., 38:3482 (1995).
Sarges R. et al., J. Med. Chem., 36:2828 (1993).
Pellerano, C., et al., IL Farmaco, 45:269 (1990).
Savini L. et al., IL Farmaco, 48:805 (1993).
Dolle R., et al., J. Med. Chem., 37:2627 (1994).
Bridges, A. J. et al., J. Med. Chem., 39:267 (1996).

* cited by examiner

Primary Examiner—Richard L. Raymond
(74) Attorney, Agent, or Firm—John W. Hogan, Jr.

(57) ABSTRACT

This invention provides compounds of formula 1 having the structure

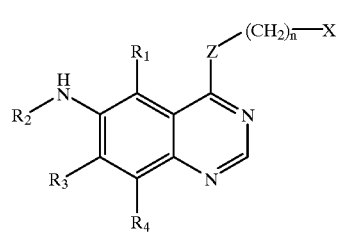

wherein:
$X, R_1, R_2, R_3, R_4, Z, X$, and n are as defined hereinbefore in the specification, which are useful as antineoplastic agents and in the treatment of certain kidney diseases, such as polycystic kidney disease.

18 Claims, No Drawings

SUBSTITUTED QUINAZOLINE DERIVATIVES

This application claims the benefit of U.S. Provisional Application No. 60/055,072, filed Aug. 1, 1997.

BACKGROUND OF THE INVENTION

This invention relates to certain quinazoline compounds as well as the pharmaceutically acceptable salts thereof. The compounds of the present invention inhibit the action of certain growth factor receptor protein tyrosine kinases (PTK) thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment of polycystic kidney disease in mammals. This invention also relates to the manufacture of said quinazolines, their use for the treatment of cancer and polycystic kidney disease, and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology*, DeVita V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.*, 7,459 (1987)], and tumors involving other major organs [Gullick, W. J., *Brit. Med. Bull.*, 47, 87 (1991)]. Because the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future*, 17, 119 (1992) and Chang, C. J.; Geahlen, R. L., *J. Nat. Prod.*, 55, 1529 (1992)].

It is also known that deregulation of EGF receptors and abnormal location of these receptors are a factors in the growth of epithelial cysts in the disease described as polycystic kidney disease [Du J., Wilson P. D., *Amer. J. Physiol.*, 269(2 Pt 1), 487 (1995); Nauta J., et al., *Pediatric Research*, 37(6), 755 (1995); Gattone V. H., et al., *Developmental. Biology*, 169(2), 504 (1995); Wilson P. D., et al., *Eur. J. Cell Biol.*, 61(1), 131, (1993)]. The compounds of this invention, which inhibit the catalytic function of the EGF receptors, are consequently useful for the treatment of this disease.

In addition to the above utilities some of the compounds of this invention are useful as intermediates for the preparation of other compounds of this invention.

The compounds of this invention are certain substituted quinazolines. Throughout this patent application, the quinazoline ring system is numbered as indicated in the formula below:

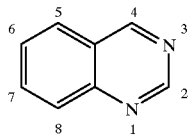

A number of 4-anilinoquinazolines which differ both in the nature and placement of the substituents at positions 5–8 compared to the compounds of this invention have been noted to have PTK inhibitory activity. The application EP-92305703.8 describes 4-anilinoquinazolines that contain simple substituents such as chloro, trifluoromethyl, or nitro groups at positions 5 to 8. The application EP-93300270.1 is similar but with a much larger variety of substituents allowed at positions 5 to 8. The application WO-9609294 describes compounds with similar substituents at positions 5 to 8 and with the substituent at to 4-position consisting of certain polycyclic ring systems. Some simple substituted quinazolines are also described in the applications WO-9524190, WO-9521613, and WO-9515758. The applications EP-93309680.2 and WO-9523141 cover similar quinazoline derivatives where the aryl group attached at position 4 can be a variety of heterocyclic ring structures. The application EP-94305195.3 describes certain quinazoline derivatives that have alkenoylamino and alkynoylamino groups among the substituents at position 6 but require a halogen atom at position 7. The application WO-9519774 describes compounds where one or more of the carbon atoms at positions 5–8 are replaced with heteroatoms resulting in a large variety of bicyclic systems where the left-hand ring is a 5 or 6-membered heterocyclic ring; in addition, a variety of substituents are allowed on the left-hand ring. The application EP-682027-A1 describes certain pyrrolopyrimidine inhibitors of PTKs. The application WO-9519970 describes compounds in which the left-hand aromatic ring of the basic quinazoline structure has been replaced with a wide variety of different heterocyclic rings so that the resulting inhibitors are tricyclic. The application WO-94305194.6 describes quinazolines where an additional 5 or 6-membered heterocyclic ring with optional substitution is fused at positions 5 and 6. The application WO-9633981 describes 4-anilino quinazolines that have at the 6-position various alkoxyalkylamino groups. The application WO-9633980 describes 4-anilino quinazolines that have at the 6-position various aminoalkylalkoxy groups. The application WO-9633979 describes 4-anilino quinazolines that have at the 6-position various alkoxyalkylalkoxy groups. The application WO-9633978 describes 4-anilino quinazolines that have at the 6-position various aminoalkylamino groups. The application WO-9633977 describes 4-anilino quinazolines that have at the 6-position various aminoalkylalkoxy groups. It is noteworthy that none of the compounds in the aforementioned applications have the unique combination of substituents contained in the compounds of the present invention.

In addition to the aforementioned patent applications, a number of publications describe 4-anilinoquinazolines: Fry, D. W., et. al., *Science*, 265, 1093 (1994), Rewcastle G. W., et. al., *J. Med. Chem.*, 38, 3482 (1995), and Bridges, A. J., et. al., *J. Med. Chem.*, 39, 267, (1996). None of the compounds described in these publications have the unique combination of substituents contained in the compounds of the present invention. In addition, it is noteworthy that no demonstration of an in vivo anti-cancer effect is described in these reports.

A PTK catalyses the transfer of a phosphate group from a molecule of ATP to a tyrosine residue located on a protein substrate. The inhibitors so far known in the art are usually competitive with either the ATP or the protein substrate of the kinase. Some of these inhibitors, the so-called mixed competitive inhibitors, can be competitive with both ATP and substrate simultaneously; all such competitive inhibitors function as reversible inhibitors. The 4-anilinoquinazolines known in the art are reversible inhibitors that are competitive with ATP [Fry, D. W., et. al., *Science*, 265, 1093 (1994)]. Since the concentration of ATP in a cell is normally very high (millimolar), compounds that are competitive with ATP may show poor in vivo activity since it is unlikely that said compounds can reach the concentrations within the cell for the extended period of time that would be necessary to displace the ATP from its binding site for a long enough time to inhibit tumor growth. Unlike the more conventional quinazoline inhibitors, the quinazoline inhibitors of this invention have the unique ability of inhibiting these PTKs in an irreversible manner and are therefore non-competitive with ATP or protein substrate. The compounds of this invention can function as irreversible inhibitors by virtue of the fact that they can form covalent bonds to amino acid residues located at the active site of the enzyme. This can result in an enhanced therapeutic usefulness of the compounds of this invention when compared to the reversible type of inhibitor. In particular, it is the unique nature and combination of substituents contained in the compounds of the present invention that lead to the irreversible binding of the inhibitor to the enzyme.

DESCRIPTION OF THE INVENTION

This invention provides a compound of formula 1:

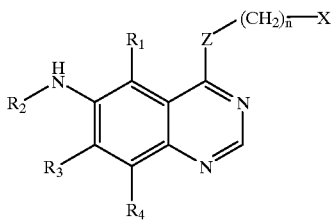

1 wherein:
X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

$R_1$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_7$—$(C(R_6)_2)_g$—Y—, $R_7$—$(C(R_6)_2)_p$—M—$(C(R_6)_2)_k$—Y—, or Het-W—$(C(R_6)_2)_k$—Y—

Y is a divalent radical selected from the group consisting of

—$(CH_2)_a$—, —O—, and —$\underset{R_6}{N}$—;

$R_7$ is —$NR_6R_6$, or —$OR_6$;
M is >$NR_6$, —O—, >N—$(C(R_6)_2)_p$$NR_6R_6$, or >N—$(C(R_6)_2)_p$—$OR_6$;
W is >$NR_6$, —O— or is a bond;
Het is a heterocycle, optionally mono- or di-substituted on carbon or nitrogen with $R_6$ and optionally mono-substituted on carbon with —$CH_2OR_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;

$R_2$, is selected from the group consisting of

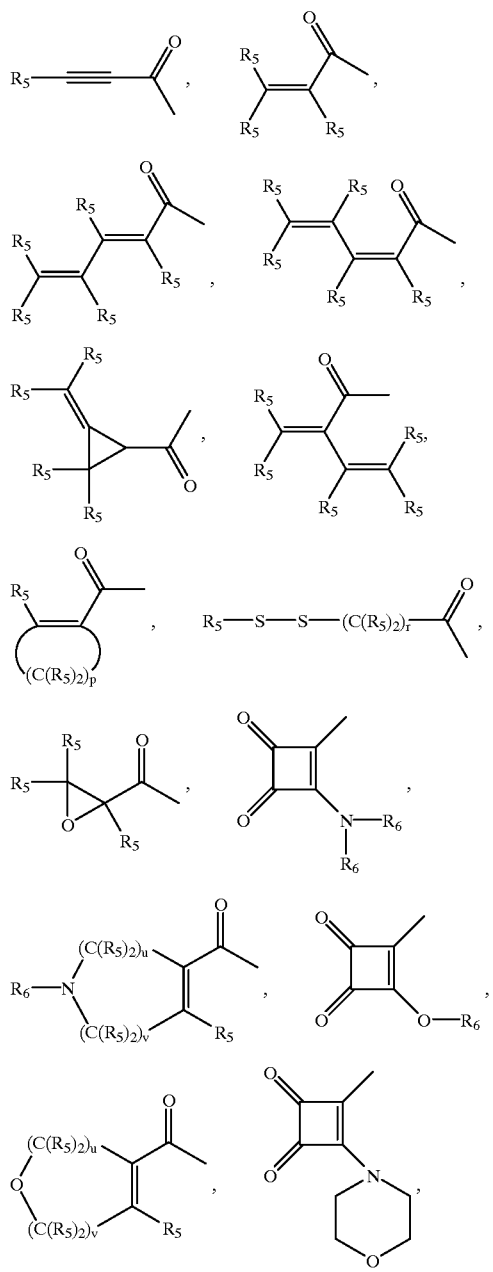

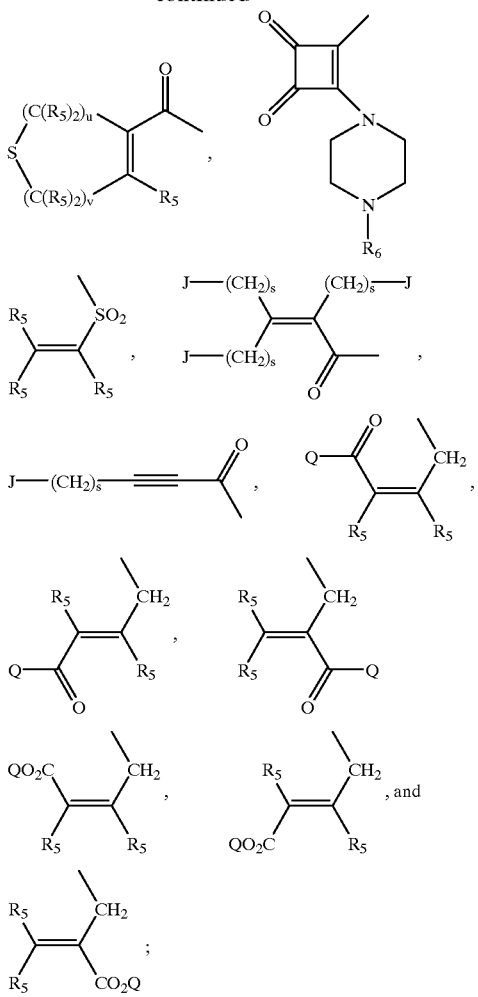

$R_5$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0 or 1;

g=1–6;

k=0–4;

n is 0–1;

p=2–4;

q=0–4;

r=1–4;

s=1–6;

u=0–1 and v=0–4, wherein the sum of u+v is 2–4;

or a pharmaceutically acceptable salt thereof, provided that when:

Z is NH;

n is 0;

$R_2$ is selected from the group consisting of

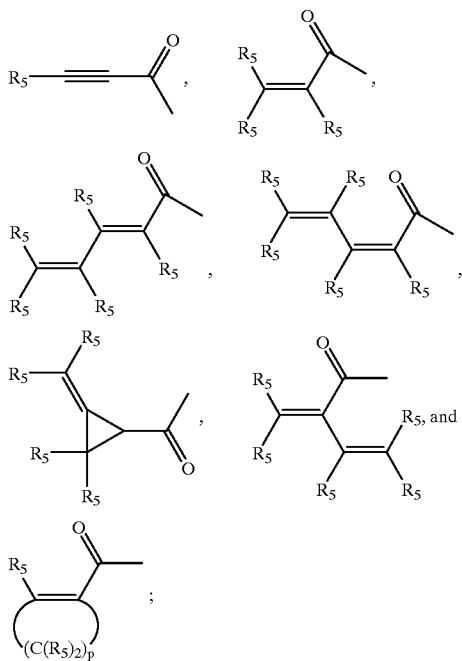

$R_5$ is independently and exclusively hydrogen, alkyl of 1–6 carbon atoms, carboxy, carboalkoxy of 1–6 carbon atoms, phenyl, or carboalkyl of 2–7 carbon atoms;

$R_1$ is hydrogen, halogen, alkyl of 1–6 carbon atoms, or alkoxy of 1–6 carbon atoms;

$R_4$ is hydrogen, halogen, alkyl of 1–6 carbon atoms, or alkoxy of 1–6 carbon atoms; and $R_3$ is hydrogen, alkyl of 1–6 carbon atoms, alkoxy of 1–6 carbon atoms, hydroxy, or trifluoromethyl;

X is not a phenyl ring exclusively substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

further provided that when $R_2$ is

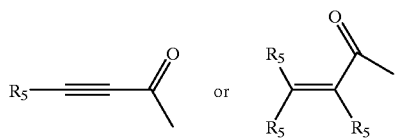

and $R_5$ is hydrogen or alkyl of 1–6 carbon atoms, $R_3$ is not halogen;

and still further provided that
when $R_6$ is alkenyl of 2–7 carbon atoms or alkynyl of 2–7 carbon atoms, such alkenyl or alkynyl moiety is bound to a nitrogen or oxygen atom through a saturated carbon atom;

and finally provided that
when Y is —$NR_6$— or $R_7$ is —$NR_6R_6$ then g=2–6;
when M is —O— and $R_7$ is —$OR_6$ then p=1–4;
when Y is —$NR_6$— then k=2–4;
when Y is —O— and M or W is —O— then k=1–4 and when W is a bond with Het bonded through a nitrogen atom and Y is —O— or —$NR_6$— then k=2–4.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, and N,N-dialkylcarbamoyl substituents include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R"$ radical, where R" is an alkyl radical of 1–6 carbon atoms. Carboxyalkyl is defined as a $HO_2C$—R'"— radical where R'" is a divalent alkyl radical of 1–6 carbon atoms. Carboalkoxyalkyl is defined as a $R"O_2C$—R'"— radical where R'" is a divalent akyl radical and where R" and R'" together have 2–7 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as $R"CO_2CH_2$— radical, where R" is an alkyl radical of 1–6 carbon atoms. Alkoxymethyl is defined as $R"OCH_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as $R"SO_2$— radical, where R" is an alkyl radical of 1–6 carbon atoms. Alkylsulfonamido, alkenylsulfonamido, alkynylsulfonamido are defined as R"SO2NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R"R'NCO— radical, where R" is an alkyl radical of 1–6 carbon atoms, R' is an alkyl radical of 1–6 carbon atoms and R', and R" may be the same or different. When X is substituted, it is preferred that it is mono- , di- , or tri-substituted, with monosubstituted being most preferred. It is preferred that of the substituents R1, R3, and R4, at least one is hydrogen and it is most preferred that two or three be hydrogen. It is also preferred that X is a phenyl ring, Z is —NH—, and n=0.

Het is a heterocycle, as defined above which may be optionally mono- or di-substituted with $R_6$ on carbon or nitrogen and optionally mono-substituted on carbon with —$CH_2OR_6$. Het may be bonded to W via a carbon atom on the heterocyclic ring, or when Het is a nitrogen containing heterocycle which also contains a saturated carbon-nitrogen bond, such heterocycle may be bonded to W, via the nitrogen when. W is a bond. When Het is substituted with $R_6$, such substitution may be on a ring carbon, or in the case of a nitrogen containing heterocycle, which also contains a saturated carbon-nitrogen, such nitrogen may be substituted with $R_6$. Preferred substituted heterocycles include 2,6-disubstituted morpholine, 2,5-disubstituted thiomorpholine, 2-substituted imidazole, N-subsitituted 1,4-piperazine, N-subsitituted piperadine, and N-subsitituted pyrrolidine.

The term exclusively in the first proviso means that when all of the conditions are true, X cannot be a phenyl ring that is subsitituted only with one or a combination of the subsitituents contained in the proviso. For example if all of the conditions of the first proviso are met, X cannot be a phenyl ring di-subsitituted with hydroxy and alkyl moieties, but could be a phenyl ring di-substituted with halogen and mercapto moieties.

The compounds of this invention may contain one or more asymmetric carbons atoms; in such cases, the compounds of this invention cover the individual diasteromers, the racemates, and the individual R and S entantiomers thereof.

The preparation of the compounds of this invention encompassed by Formula 9 is described below in Flowsheet 1 where $R_1$, $R_3$, $R_4$, and X are defined and $R_{10}$ is alkyl of 1–6 carbon atoms (preferably isobutyl). $R_2'$ is a radical selected from the group consisting of:

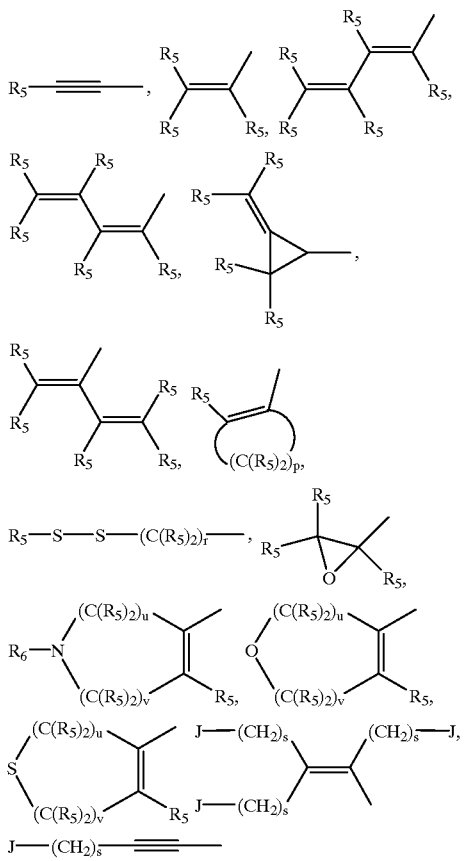

wherein $R_6$, $R_5$, J, s, r, u, and v are defined. According to the sequence of reaction outlined in Flowsheet 1, a 5-nitro-anthranilonitrile of Formula 2 is heated at about 100° C. with or without solvent containing an excess of N,N-dimethylformamide dimethyl acetal to furnish an amidine of Formula 3. Heating a solution of amidine 3 and the aniline 4 in acetic acid for 1 to 5 hours gives the 6-nitro-4-anilinoquinazolines of Formula 5. Reduction of the nitro group of 5 with a reducing agent such as iron using an acetic acid-alcohol mixture or an aqueous ammonium chloride-methanol mixture at elevated temperature or by catalytic hydrogenation gives the 6-amino4-anilinoquinazolines of Formula 6. Acylation of 6 with either an acid chloride of Formula 7 or a mixed anhydride of Formula 8 (which is prepared from the corresponding carboxylic acid) in an inert solvent such as tetrahydrofuran (THF) in the presence of an organic base such as pyridine, diisopropylethylamine, N-methylmorpholine, or triethylamine gives the compounds of this invention represented by Formula 9. In those cases where 7 or 8 have an asymmetric carbon atom, they can be used as the racemate or as the individual R or S enantiomers in which case the compounds of this invention will be in the racemic or R and S optically active forms, respectively. The 5-nitro-anthranilonitriles of Formula 2 needed to prepare the compounds of this invention are either already known to the art or can be prepared by procedures known in the art as detailed in the following references: Baudet, Recl.Trav.Chim.Pays-Bas, 43, 710 (1924); Hartmans, Recl.Trav.Chim.Pays-Bas, 65, 468, 469 (1946); Taylor et al., J.Amer.Chem.Soc., 82, 6058,6063 (1960); Taylor et al., J.Amer.Chem.Soc., 82, 3152,3154 (1960); Deshpande; Seshadri, Indian J.Chem., 11, 538 (1973); Katritzky, Alan R.; Laurenzo, Kathleen S., J.Org.Chem., 51, 5039–5040 (1986); Niclas, Hans-Joachim; Bohle, Matthias; Rick, Jens-Detlev; Zeuner,Frank; Zoelch, Lothar, Z.Chem., 25(4), 137–138 (1985). In those cases where the $R_2'$ moiety contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The former protecting group can be removed from the final products of Formula 9 by treatment with an acid such as trifluoroactic acid while the latter protecting group can be removed by catalytic hydrogenation. In those cases where the $R_2'$ moiety contains hydroxyl groups, the hydroxyl groups will first have to be protected prior to anhydride or acid chloride formation. Suitable protecting groups include, but are not limited to, t-butyldimethylsilyl, tetrahydropyranyl, or benzyl protecting groups. The first two protecting groups can be removed from the final products of formula 9 by treatment with an acid such as acetic acid or hydrochloric acid while the latter protecting group can be removed by catalytic hydrogenation. In those cases, where the X group of intermediate 6 contains primary or secondary amino groups or hydroxyl groups, it may be necessary to protect these groups prior to the reaction of 6 with the anhydride 7 or acid chloride 8. The same protecting groups describe above can be used and they can be removed from the products 9 as previously described. In those cases, where $R_1$, $R_3$, or $R_4$ of intermediate 5 contain primary or secondary amino groups or hydroxyl groups, it may be necessary to protect these groups prior to the reduction of 5 to give 6. The same protecting groups describe above can be used and they can be removed from the products 9 as previously described.

FLOWSHEET 1

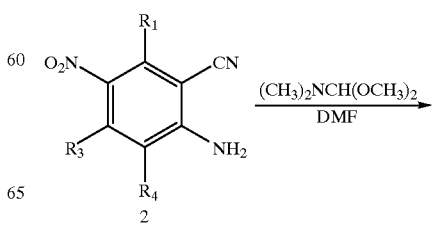

-continued

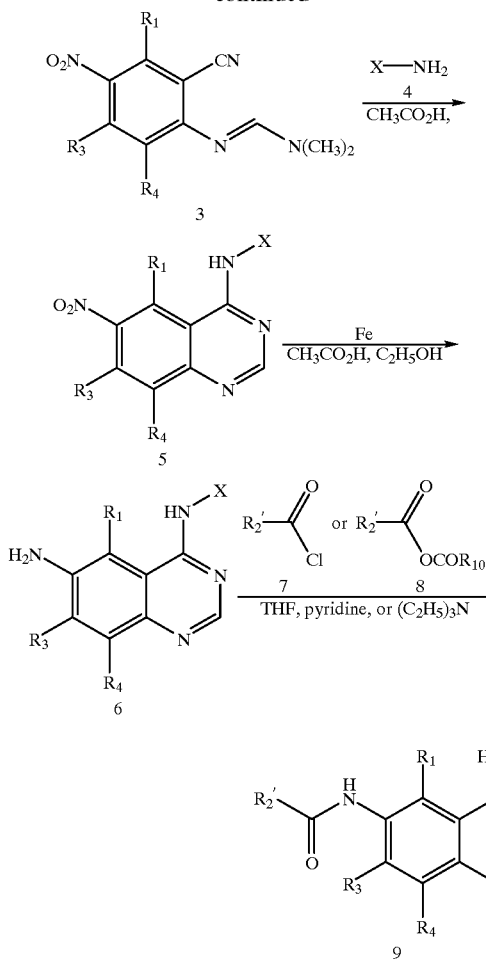

The preparation of the compounds of this invention encompassed by Formula 12 is described below in Flowsheet 2 wherein $R_1$, $R_3$, $R_4$, $R_5$, X, and n are described above. According to the reaction outlined in Flowsheet 2, the 6-amino-quinazolines of Formula 10 (prepared as in Flowsheet 1) are acylated with a cyclic anhydride of Formula 11 in an inert solvent such as tetrahydrofuran in the presence of a basic catalyst such as pyridine or triethylamine. In those cases where the $R_5$ contains primary or secondary amino groups, the amino groups will first have to be protected prior to anhydride formation. Suitable protecting groups include, but are not limited to, tert-butoxycarbonyl (BOC) and benzyloxycarbonyl (CBZ) protecting groups. The former protecting group can be removed from the final products of Formula 12 by treatment with an acid such as trifluoroactic acid while the latter protecting group can be removed by catalytic hydrogenation. In those cases where the $R_5$ contains hydroxyl groups, the hydroxyl groups will first have to be protected prior to anhydride formation. Suitable protecting groups include, but are not limited to, t-butyldimethylsilyl, tetrahydropyranyl, or benzyl protecting groups. The first two protecting group can be removed from the final products of formula 12 by treatment with an acid such as acetic acid or hydrochloric acid while the latter protecting group can be removed by catalytic hydrogenation. In those cases, where the X group of intermediate 10 contains primary or secondary amino groups or hydroxyl groups, it may be necessary to protect these groups prior to the reaction of 10 with the anhydride 11. The same protecting groups describe above can be used and they can be removed from the products 12 as previously described. In those cases, where $R_1$, $R_3$, or $R_4$ of intermediate 10 contain primary or secondary amino groups or hydroxyl groups, it may be necessary to protect these groups prior to the reaction of 10 and 11. The same protecting groups describe above can be used and they can be removed from the products 12 as previously described.

FLOWSHEET 2

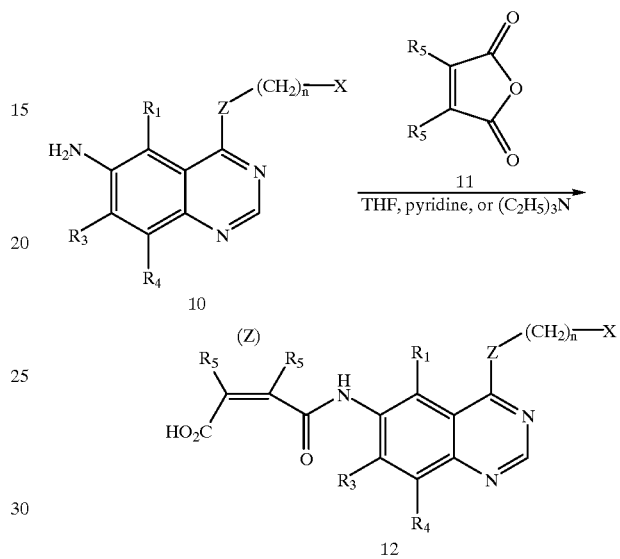

The preparation of the compounds of this invention encompassed by Formula 18 is described below in Flowsheet 3 wherein $R_1$, $R_3$, $R_4$, $R_{10}$, Z, n, and X are defined. $R_2'$ is described above. According to the reactions outlined in Flowsheet 3, a 4-chloro-6-nitroquinazoline, 10, (see Morley, J S. and Simpson, J. Chem.. Soc., 360 (1948) for the preparation of one such compound) can be reacted with an amine or aniline 11 by heating in an inert solvent such as tetrahydrofuran, butanol, or methoxyethanol to give compounds of Formula 14 where Z is —NH—. The reaction of 10 with a mercaptan or thiophenol 12 in an inert solvent can be accomplished using a base such as sodium hydride to give compounds of Formula 14 where Z is —S—. The reaction of 10 with a alcohol or phenol 12 in an inert solvent can be accomplished using a base such as sodium hydride to give compounds of Formula 14 where Z is —O—. Compounds of Formula 14 can be reduced to a 6-amino4-chloroquinazoline, 15, using a reducing agent such as sodium hydrosulfite in a two phase system consisting of tetrahydrofuran and water in the presence of a small amount of phase transfer catalyst or by using iron in refluxing protic solvents containing acetic acid or ammonium chloride. Acylation of 15 with either an acid chloride of Formula 16 or a mixed anhydride of Formula 17 (which is prepared from the corresponding carboxylic acid) in an inert solvent such as tetrahydrofuran (THF) in the presence of an organic base such as pyridine, triethylamine, diisopropylethylamine, or N-methyl morpholine gives the compounds of this invention of Formula 18. In those cases where 16 or 17 have an asymmetric carbon atom, they can be used as the racemate or as the individual R or S entantiomers in which case the compounds of this invention will be in the racemic or R and S optically active forms, respectively. In those cases, where the $R_2'$ contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The former protecting group can be removed from the final products of Formula 18 by treatment with an acid such as trifluoroactic acid while the latter protecting group can be removed by catalytic hydrogenation. In those cases where the $R_2$' contains hydroxyl groups, the hydroxyl groups may first have to be protected prior to anhydride or acid chloride formation. Suitable protecting groups include, but are not limited to, t-butyldimethylsilyl, tetrahydropyranyl, or benzyl protecting groups. The first two protecting groups can be removed from the final products of Formula 18 by treatment with an acid such as acetic acid or hydrochloric acid while the latter protecting group can be removed by catalytic hydrogenation. In those cases, in intermediates 11, 12, or 13 where X contains primary or secondary amino groups or hydroxyl groups, it may be necessary to protect these groups prior to the reaction with 10. The same amine or alcohol protecting groups describe above can be used and they can be removed from the products 18 as previously described.

FLOWSHEET 3

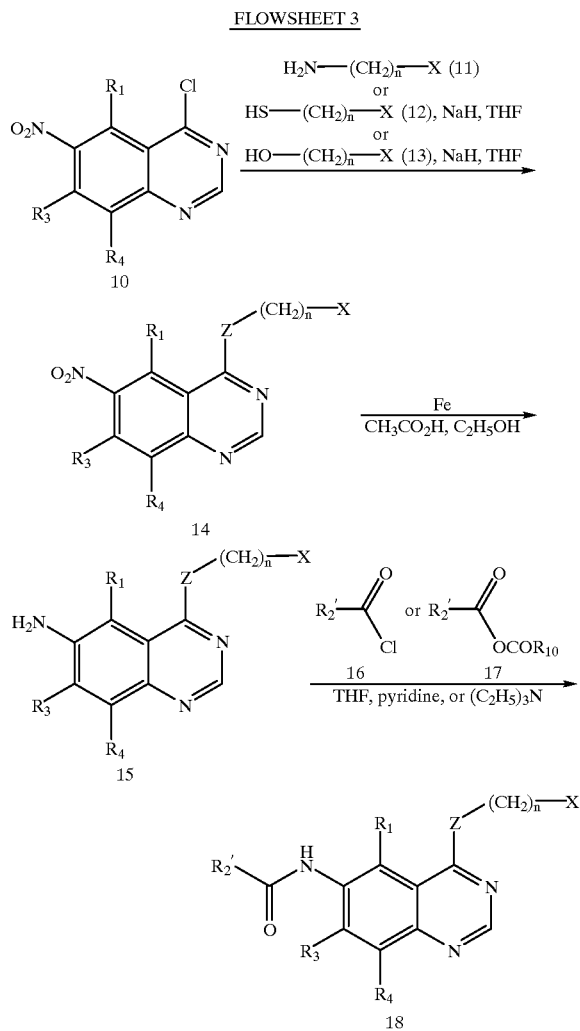

The preparation of the compounds of this invention encompassed by Formula 26 is described below in Flowsheet 4 wherein $R_1$, $R_3$, $R_4$, $R_{10}$, n, and X are defined. $R_2$' is described above. According to the reactions outlined in Flowsheet 4, the aniline 19 is heated with dimethylformamide dimethyl acetal (DMF-acetal) in an inert solvent to furnish compounds of the Formula 20. The nitro group of 20 is reduced to the corresponding amino compound 21 using a palladium catalyst and a source of hydrogen which can be hydrogen itself or cyclohexene. Acylation of 21 with either an acid chloride of Formula 22 or a mixed anhydride of Formula 23 (which is prepared from the corresponding carboxylic acid) in an inert solvent such as tetrahydrofuran (THF) in the presence of an organic base such as pyridine or N-methyl morpholine gives the compounds of Formula 24. In those cases where 22 or 23 have an asymmetric carbon atom, they can be used as the racemate or as the individual R or S entantiomers in which case the compounds of this invention will be in the racemic or R and S optically active forms, respectively. Heating a compound of Formula 24 with an aniline or benzylamine of Formula 25, in a inert solvent such as acetic acid gives the compounds of this invention represented by Formula 26. In those cases where the $R_2$' contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The former protecting group can be removed from the final products of Formula 26 by treatment with an acid such as trifluoroactic acid while the latter protecting group can be removed by catalytic hydrogenation. In those cases where the $R_2$' contains hydroxyl groups, the hydroxyl groups will first have to be protected prior to anhydride or acid chloride formation. Suitable protecting groups include, but are not limited to, t-butyldimethylsilyl, tetrahydropyranyl, or benzyl protecting groups. The first two protecting groups can be removed from the final products of formula 26 by treatment with an acid such as acetic acid or hydrochloric acid while the latter protecting group can be removed by catalytic hydrogenation. In those cases where in intermediate 25, X contains primary or secondary amino groups or hydroxyl groups it may be necessary to protect these groups prior to the reaction of 21 with the anhydride 23 or acid chloride 22. The same protecting groups describe above can be used and they can be removed from the products 26 as previously described. In those cases where in intermediate 19, $R_1$, $R_3$, or $R_4$ contain primary or secondary amino groups or hydroxyl groups it may be necessary to protect these groups prior to the reaction of 19 and dimethylformamide dimethyl acetal (DMF-acetal). The same protecting groups describe above can be used and they can be removed from the products 26 as previously described.

FLOWSHEET 4

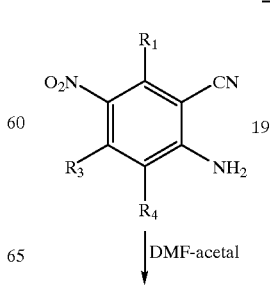

15
-continued

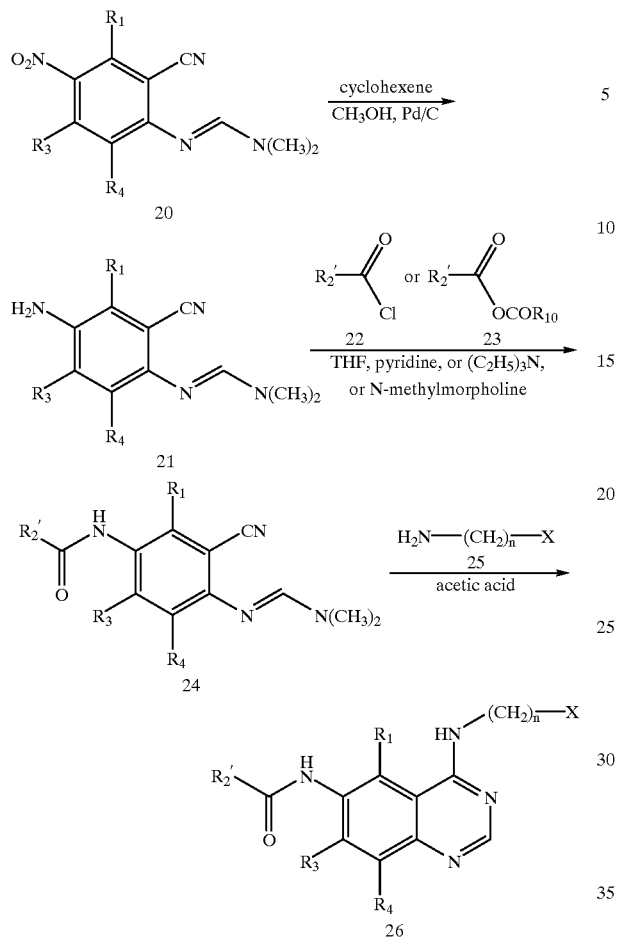

List A

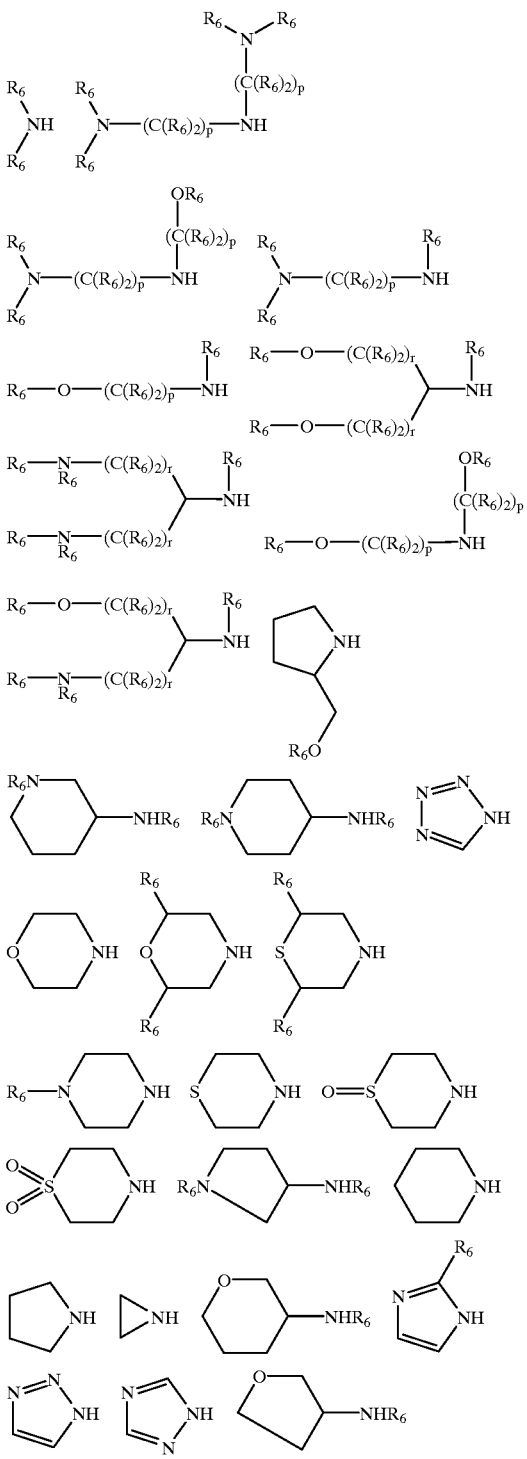

In addition to the methods described above in Flowsheets 1–4, the methods described in the following patent applications can be used to prepare many of the 6-amino-quinazolines (such as those of Formulas 6, 15, and 10 in the above flowsheets) that are needed to prepare the compounds of this invention: WO-9633981, WO-9633979, WO-9633978, WO-9616960, WO-9609294, WO-9630347, WO-9615118, WO-9609294, EP-635507, EP-602851, and EP-520722

In order to prepare the compounds of this invention, certain amines are required that are shown below in List A wherein $R_6$, p, and r are as defined above. These amines are available commercially, are known in the chemical literature, or can be prepared by simple procedures that are well known in the art. In some cases, these amines may have an asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these amines will be represented by the generic structure of the formula:

(R')$_2$NH, wherein this formula can represent a primary or secondary amine

In order to prepare the compounds of this invention certain alcohols are required that are shown below in List B wherein $R_6$, p, and r are as defined above. These alcohols are available commercially, are known in the chemical literature, or can be prepared by simple procedures that are well known in the art. In some cases, these alcohols may have an asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these alcohols will be represented by the generic structure of the formula:

R'OH

List B

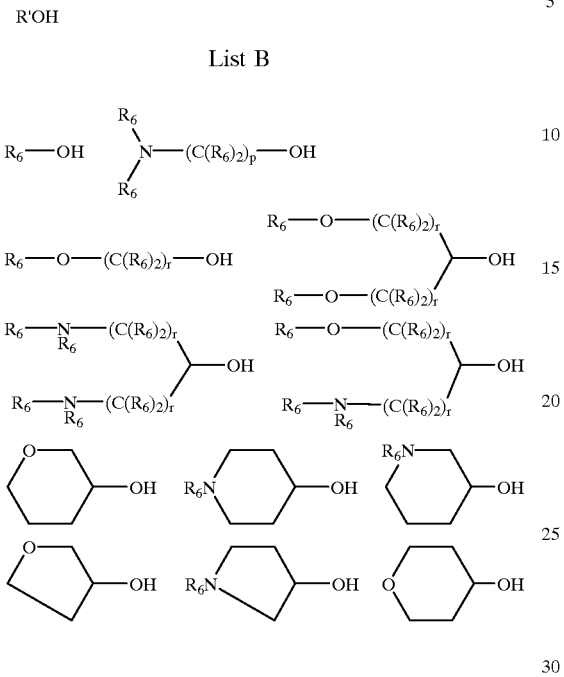

In order to prepare some of the compounds of this invention certain mixed anhydrides of Formulas 31, 34, and 38 are required; these are prepared as outlined below in Flowsheet 5–6 wherein $R_6$, $R_{10}$, X, Z, n, and s are as defined above. J' is a halogen atom chlorine, bromine, or iodine, or is a toslyate (p-toluenesulfonate) or mesylate (methanesulfonate) group. The reaction of 27 with an amine of List A is accomplished by heating in an inert solvent such as tetrahydrofuran or N,N-dimethylformamide, or using potassium or cesium carbonate in acetone. The temperature and duration of the heating will depend on the reactivity of 27; longer reaction times and higher temperatures may be required when s is greater than 1. Treatment of 28 with an alkyl lithium reagent followed by quenching with an atmosphere of dry carbon dioxide furnishes the carboxylic acids of formula 29. These can be converted to mixed anhydrides of Formula 31 using a reagent such as isobutylchloroformate in an inert solvent such as tetrahydrofuran in the presence of a base such as N-methylmorpholine. These anhydrides can then be used to prepare the compounds of this invention as described above in Flowsheets 1,3, and 4. The reaction of 27 with an alcohol of List B is accomplished using sodium hydride or other non-nucleophic base such as potassium or cesium carbonate in an inert solvent such as tetrahydrofuran, acetone, or N,N-dimethylformamide. In some cases, the alcohol of List B can also be the solvent of the reaction. Treatment of 32 with an alkyl lithium reagent followed by quenching with an atmosphere of dry carbon dioxide furnishes the carboxylic acids of formula 33. These can be converted to mixed anhydrides Formula 34 using a reagent such as isobutylchloroformate in an inert solvent such as tetrahydrofuran in the presence of a base such as N-methylmorpholine. These anhydrides can then be used to prepare the compounds of this invention as described above in Flowsheets 1,3, and 4.

FLOWSHEET 5

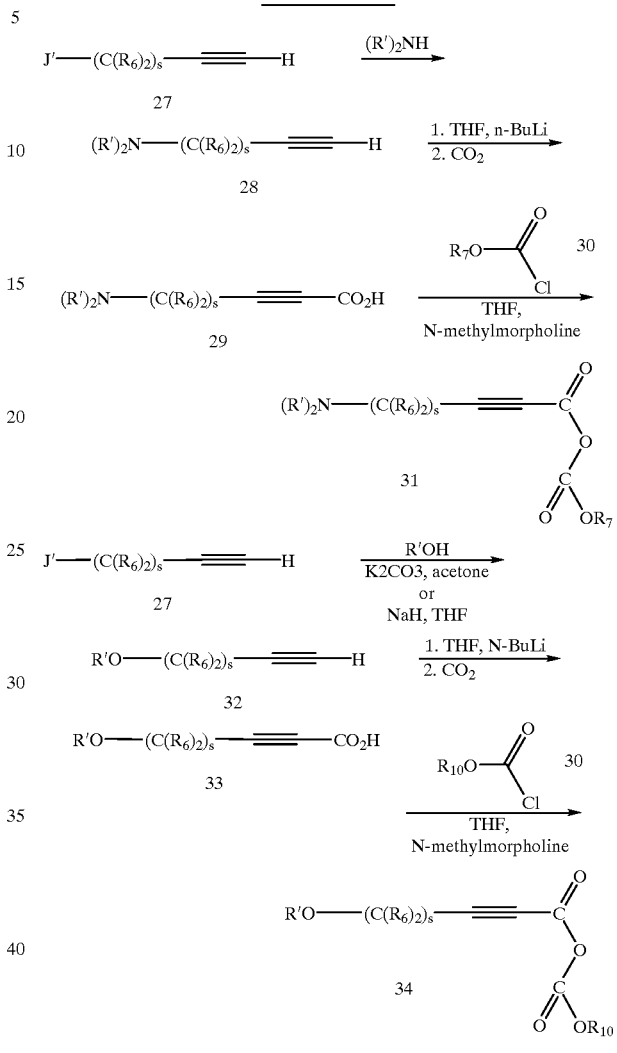

As outline in Flowsheet 6 below wherein $R_1$, $R_3$, $R_4$, $R_6$, $R_{10}$, X, Z, n, and s are as defined above, alcohols 35 can be protected with a t-butyl dimethysilyl protecting group by the reaction with the respective silyl chloride in methylene chloride in the presence of triethylamine and 4-N,N-dimethylamino pyridine (DMAP). The resulting protected alcohols, 36, are converted to the acetylenic Grignard reagents which, in turn, are maintained under an atmosphere of dry carbon dioxide to give the carboxylic acids 37. As described above these are converted to the mixed anhydrides 38 which on reaction with the 6-aminoquinazoline 39 (as described above in Flowsheets 1,3, and 4) 40. In the final step of the sequence, the silyl protecting group is removed by treating with acid in a protic solvent mixture to give the compounds of this invention represented by Formula 41.

FLOWSHEET 6

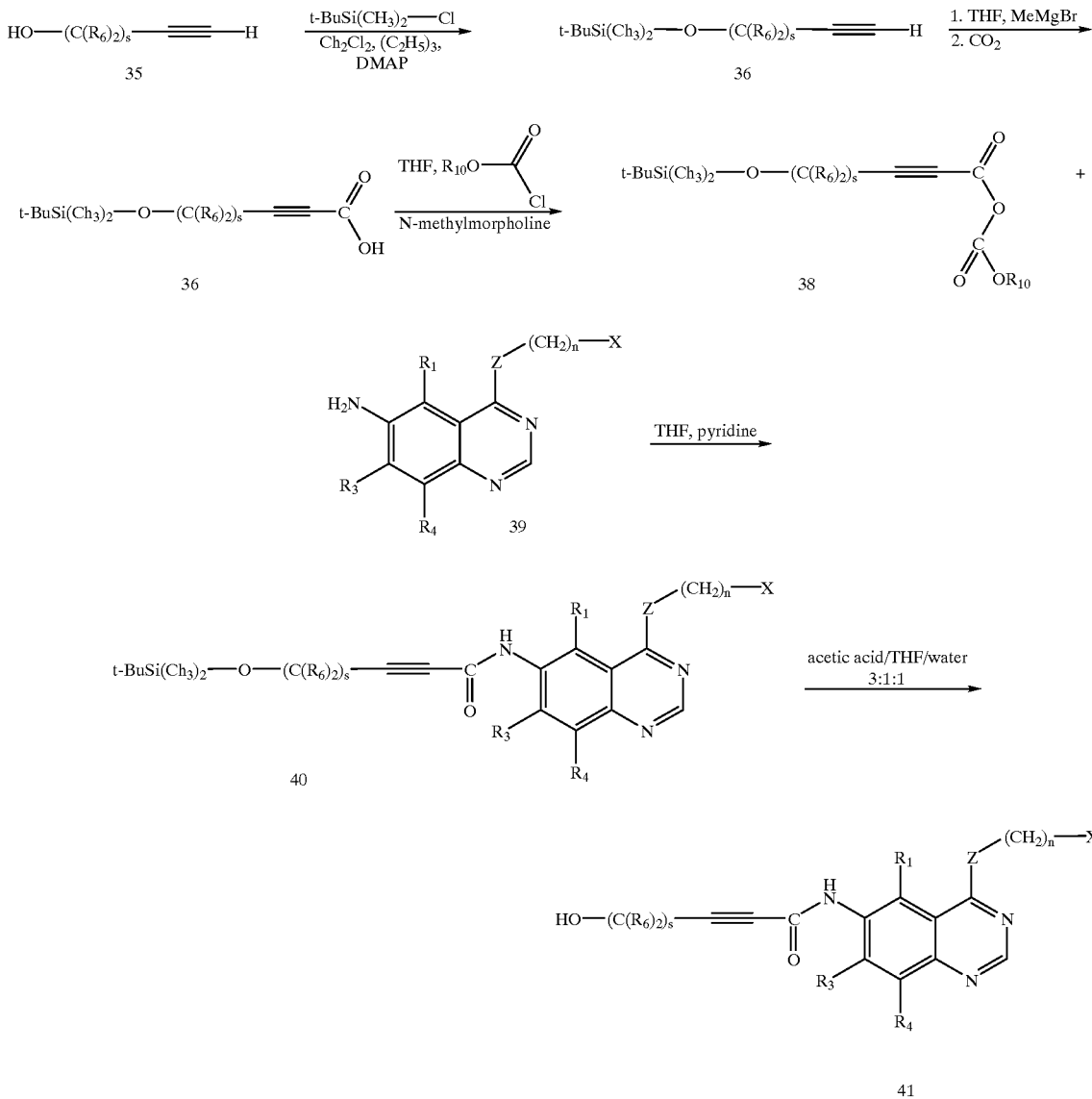

Compounds of this invention are also prepared as shown below in Flowsheet 7 wherein $R_1$, $R_3$, $R_4$, $R_6$, $R_{10}$, X, Z, n, and s are as defined above. J' is a halogen atom chlorine, bromine, or iodine, or is a toslyate or mesylate group. Treatment of 42 with an alkyl lithium reagent at low temperature followed by quenching with an atmosphere of dry carbon dioxide furnishes the carboxylic acids of formula 43. These can be converted to mixed anhydrides of Formula 44 using a reagent such as isobutylchloroformate in an inert solvent such as tetrahydrofuran in the presence of a base such as N-methylmorpholine. These anhydrides can then be used to prepare the compounds of this invention as by the reaction with the 6-amino-quinazolines 45 described above in Flowsheets 1,3, and 4. The reaction of 46 with an alcohol of List B is accomplished using sodium hydride or other non-nucleophic base in an inert solvent such as tetrahydrofuran or N,N-dimethylformamide to give the compounds of this invention represented by 47. In some cases, the alcohol of List B can also be the solvent of the reaction. The reaction of 46 with an amine of List A gives the compounds of this invention represented by 48 is accomplished by heating in an inert solvent such as tetrahydrofuran or N,N-dimethylformamide, or using potassium or cesium carbonate in acetone. The temperature and duration of the heating will depend on the reactivity of 46; longer reaction times and higher temperatures may be required when s is greater than 1.

FLOWSHEET 7

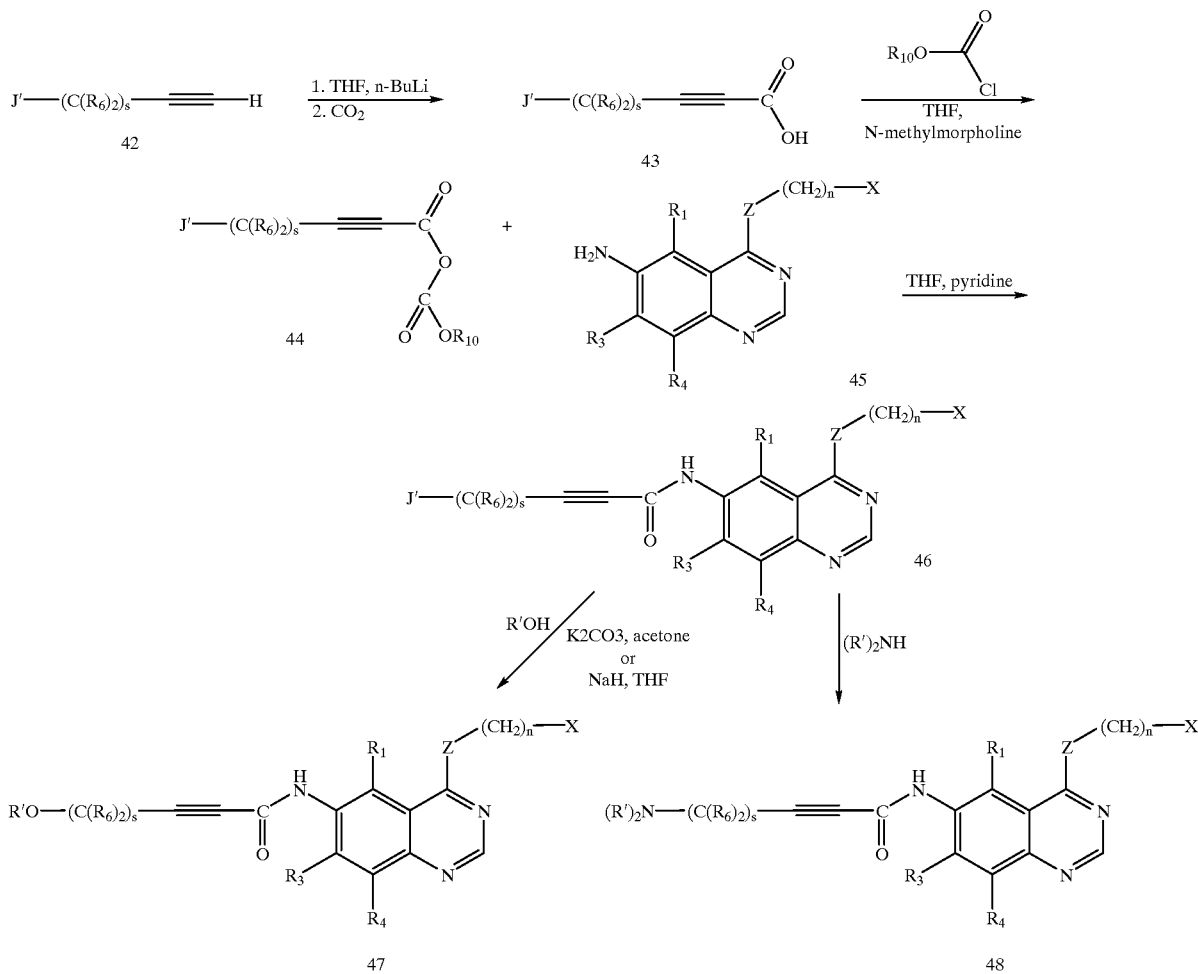

FLOWSHEET 8

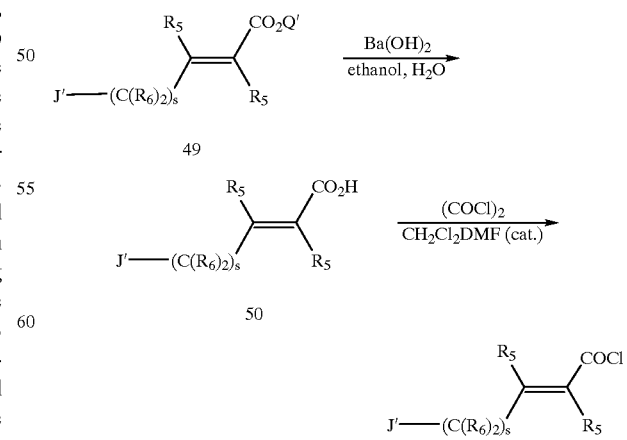

Other carboxylic acid chlorides and anhydrides needed to prepare some of the compounds of this invention are prepared as shown below in Flowsheet 8 wherein $R_6$, $R_5$, $R_{10}$, X, Z, J', n, and s are as defined above. Q' is an alkyl group of 1–6 carbon atoms. The esters 49, 53, or 57 can be hydrolyzed with a base such as barium hydroxide to give the respective carboxylic acid 50, 54, or 58. These acid can be converted to the respective carboxylic acid chlorides 51 or 56 by using oxalyl chloride and catalytic N,N-dimethylformamide in an inert solvent or respective mixed anhydrides 55 or 59 by using isobutyl chloroformate and an organic base such as N-methylmorpholine. The leaving group in compounds represented by Formula 52 can be displaced by the amines of List A or the alcohols of List B by using procedures previously described to give the intermediates 57 and 53, respectively. These carboxylic acid chlorides 51 and 56 and these anhydrides 55 and 59 can be used to prepare some of the compounds of this invention by using the methods outlined herein above in Flowsheets 1,3, and 4.

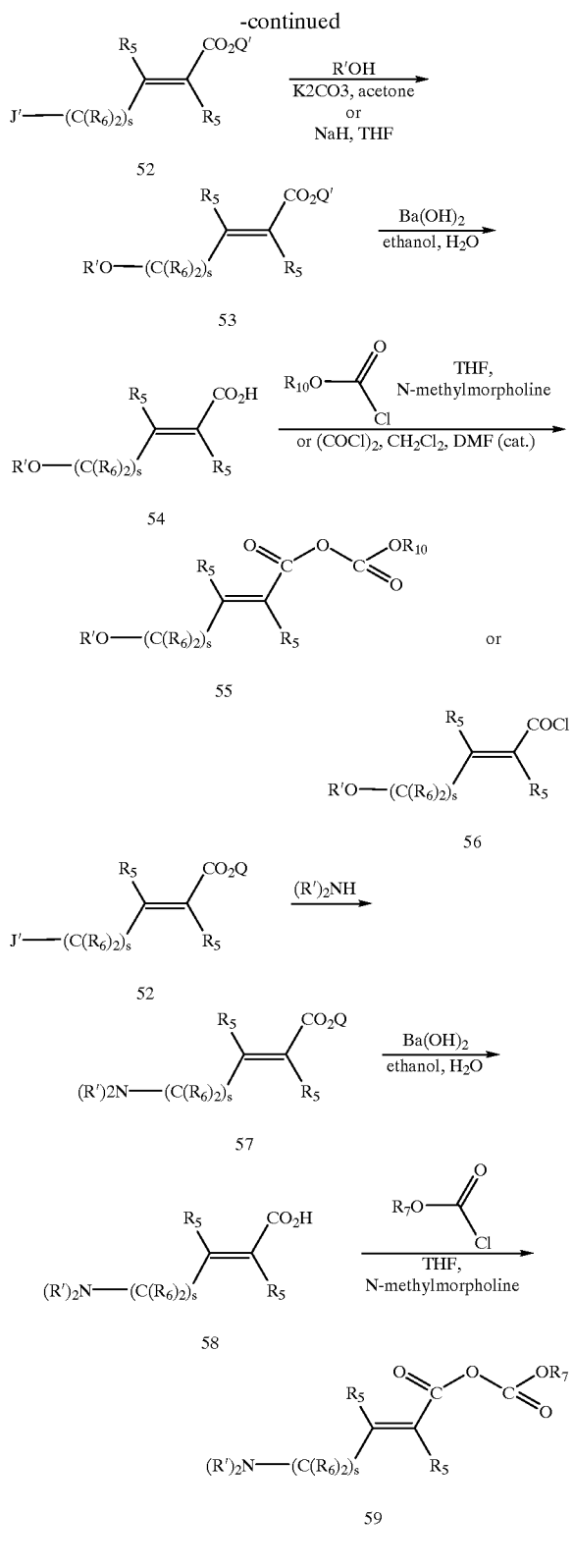

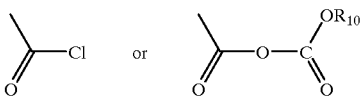

and A is the radical:

—N(R')$_2$, —OR', or —J' wherein —N(R')$_2$ is derived from the amines of List A, —OR' are derived from the alcohols of List B, and J' is a leaving group as defined previously. By making use of these carboxylic acid chlorides and anhydrides, by following the methods summarized above in Flowsheets 1, 3, and 4, and by pursuing the details described in the examples given below, many of the compounds of this invention can be prepared.

List C

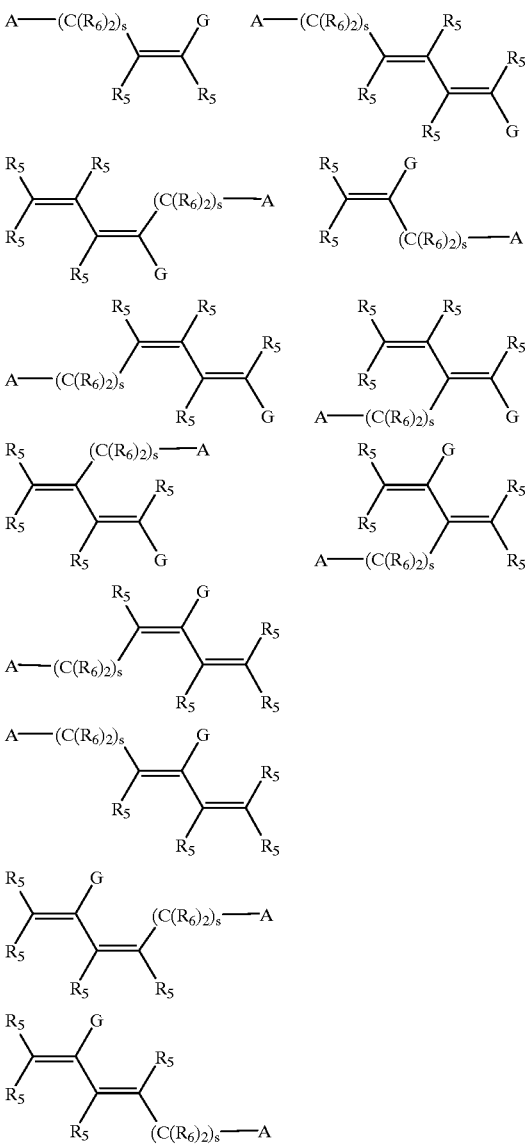

By using the methods identical to those outlined above in Flowsheet 8, it is possible to prepare the analogous carboxylic acid chlorides and anhydrides given below in List C wherein $R_6$, $R_5$, p, and s are as previously defined. G is the radical:

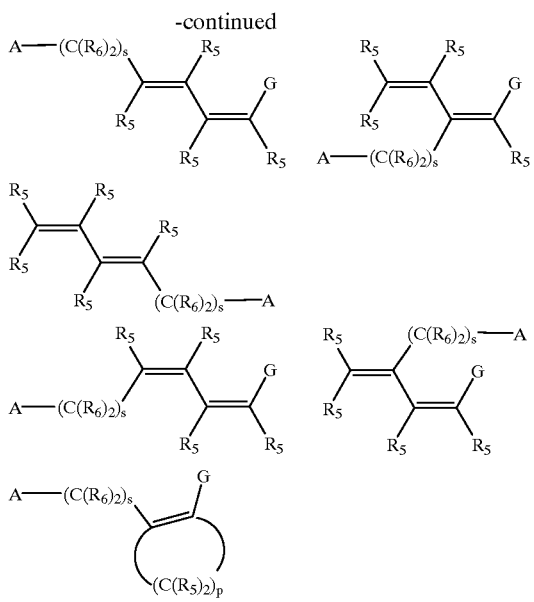

Compounds of this invention represented by Formulas 62–63 can be prepared as shown in Flowsheet 9 wherein $R_1$, $R_3$, $R_4$, $R_6$, $R_5$, $R_{10}$, X, Z, J', n, and s are as defined above. The reaction of the carboxylic acid chlorides 60 and the 6-aminoquinazolines 61 using an organic base in an inert solvent gives the compounds of this invention represented by Formula 62. The reaction of 62 with an alcohol of List B is accomplished using sodium hydride or other non-nucleophic base such as potassium or cesium carbonate in an inert solvent such as tetrahydrofuran, acetone, or N,N-dimethylformamide to give the compounds of this invention represented by 63. In some cases, the alcohol of List B can also be the solvent of the reaction. The reaction of 62 with an amine of List A to give the compounds of this invention represented by 64 is accomplished by heating in an inert solvent such as tetrahydrofuran or N,N-dimethylformamide. The temperature and duration of the heating will depend on the reactivity of 62; longer reaction times and higher temperatures may be required when s is greater than 1. In addition, by using this method, the carboxylic acid chlorides and mixed anhydrides listed in List C can be used to prepare the analogous compounds of this invention.

FLOWSHEET 9

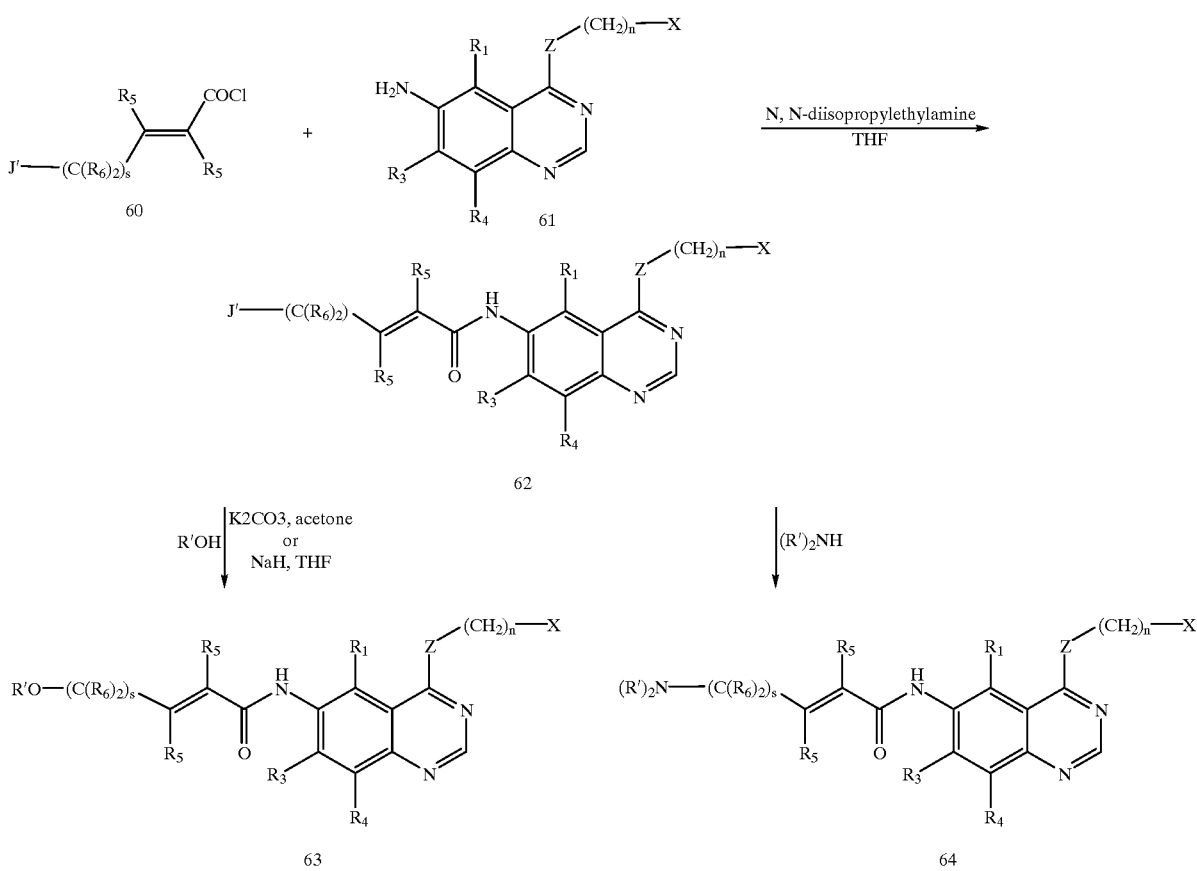

Some of the compounds of this invention can be prepared as outline below in Flowsheet 10 wherein $R_1$, $R_3$, $R_4$, $R_6$, $R_{10}$, X, Z, J', n, and r are as defined above. The acetylenic alcohols 65 can be coupled to the halides, mesylates, or tosylates 66 using a base such as sodium hydride in an inert solvent such as tetrahydrofuran. The resulting acetylene, 67, is then treated with an alkyl lithium reagent at low temperature. Maintaining the reaction under an atmosphere of carbon dioxide then gives the carboxylic acids 68. These, in turn, are reacted with the 6-amino-quinazolines, 69, via the mixed anhydrides to give the compounds of this invention represented by Formula 70. Alternatively, the intermediates 67 can be prepared starting with an alcohol 71 by first treating it with a base such as sodium hydride in an inert solvent such as tetrahydrofuran and then adding an acetylene 72 that has an appropriate leaving group. In a similar manner, the amino alcohols represented by the formula: $(R_6)_2N$—$(C(R_6)_2)_r$—OH by reacting with 72, and applying the chemistry of Flowsheet 10, can be converted to the compounds of this invention represented by the formula:

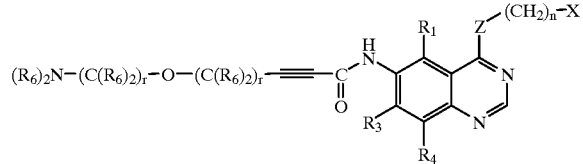

FLOWSHEET 10

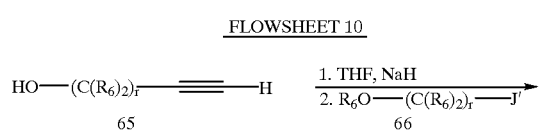

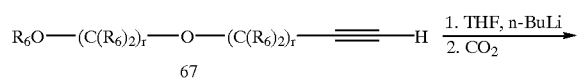

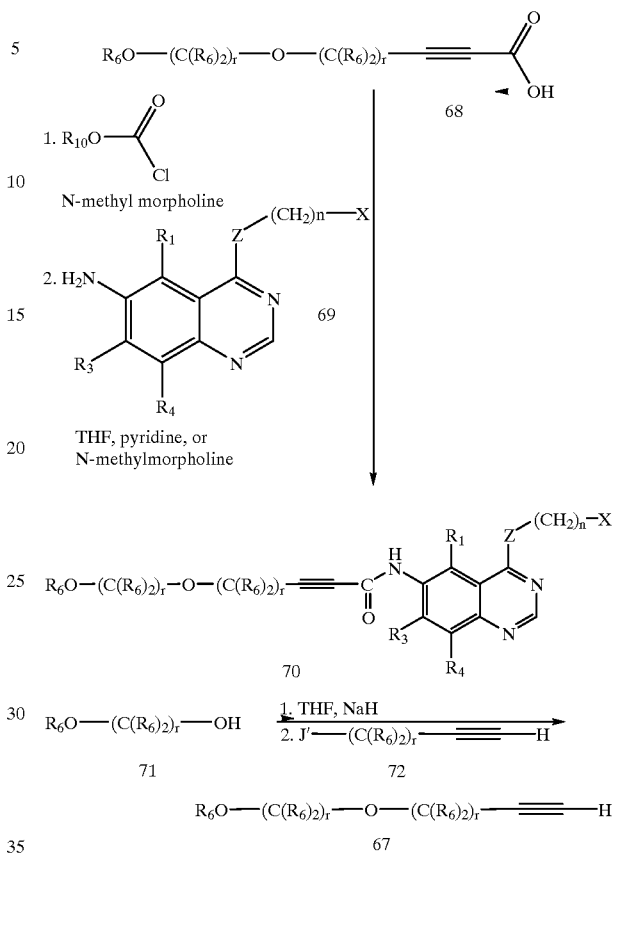

The compounds of this invention represented by Formula 76 and 77 are prepared as shown below in Flowsheet 11 wherein $R_1$, $R_3$, $R_4$, $R_6$, and n defined above and the amines $HN(R")_2$ are selected from the group:

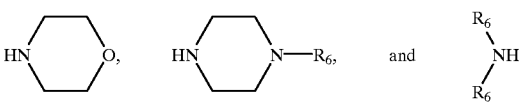

Refluxing 73 and 74 in an a solvent such as ethanol gives the intermediate 75 which can react with an amine in refluxing ethanol to give the compounds of this invention represented by Formula 76. Treating 75 with an excess of a sodium alkoxide in an inert solvent or a solvent from which the alkoxide is derived gives the compounds of this invention of Formula 77.

FLOWSHEET 11

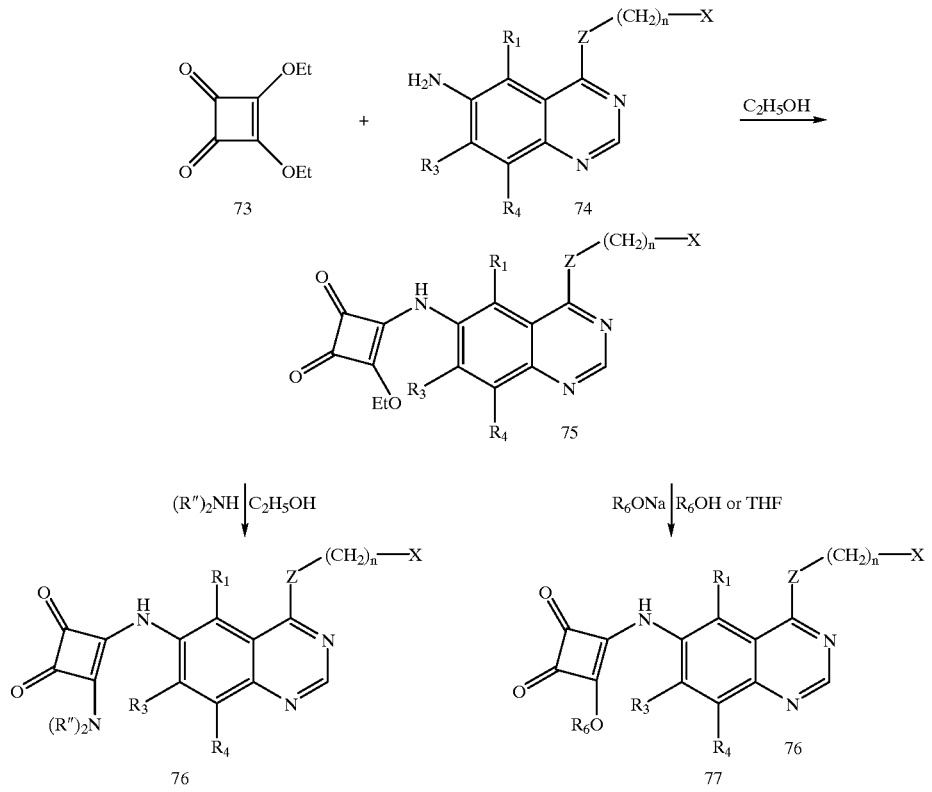

Compounds of this invention represented by Formula 83 can be prepared as shown in Flowsheet 12 wherein $R_1$, $R_3$, $R_4$, $R_6$, $R_5$, $R_{10}$, X, Z, n, and r are as defined above. The reaction of the mecapto carboxylic acids 78 with the reagents 79 give the compounds represented by Formula 80. Alternatively, 80 can be prepared from the mercaptan $R_5SH$ using the mercapto acid 78, triethylamine and 2,2'-dipyridyl disulfide. Mixed anhydride formation to give 81 followed by condensation with the 6-amino-quinazolines 82 give the compounds of this invention.

FLOWSHEET 12

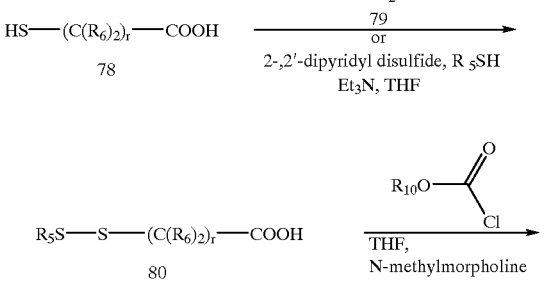

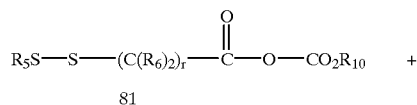

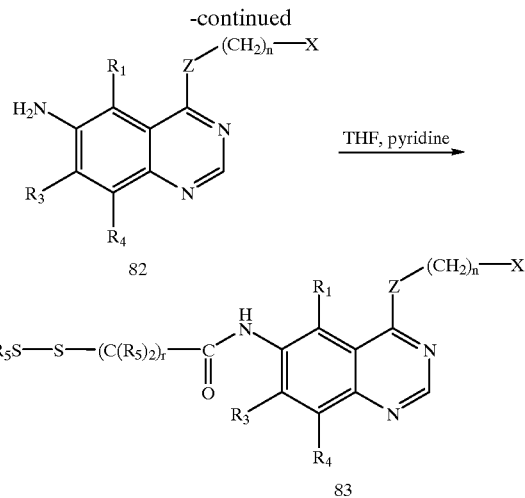

Compounds of this invention represented by Formulas 86–88 can be prepared as shown in Flowsheet 13 wherein $R_1$, $R_3$, $R_4$, $R_5$, J', X, Z, and n are as defined above. Q' is alkyl of 1–6 hydrogen atoms, alkoxy of 1–6 hydrogen atoms, hydroxy, or hydrogen. Akylation of 84 with the 6-amino-quinazolines 85 can be accomplished by heating in an inert solvent such as N,N-dimethylformamide using a base such as potassium carbonate to give the compounds of this invention represented by the Formula 86. When Q' is alkoxy, the ester group can be hydrolyzed to an acid using a base such as sodium hydroxide in methanol. In a similar manner, by using intermediates 89 and 90, the compounds of this invention represented by Formulas 87 and 88 can be prepared, respectively.

FLOWSHEET 13

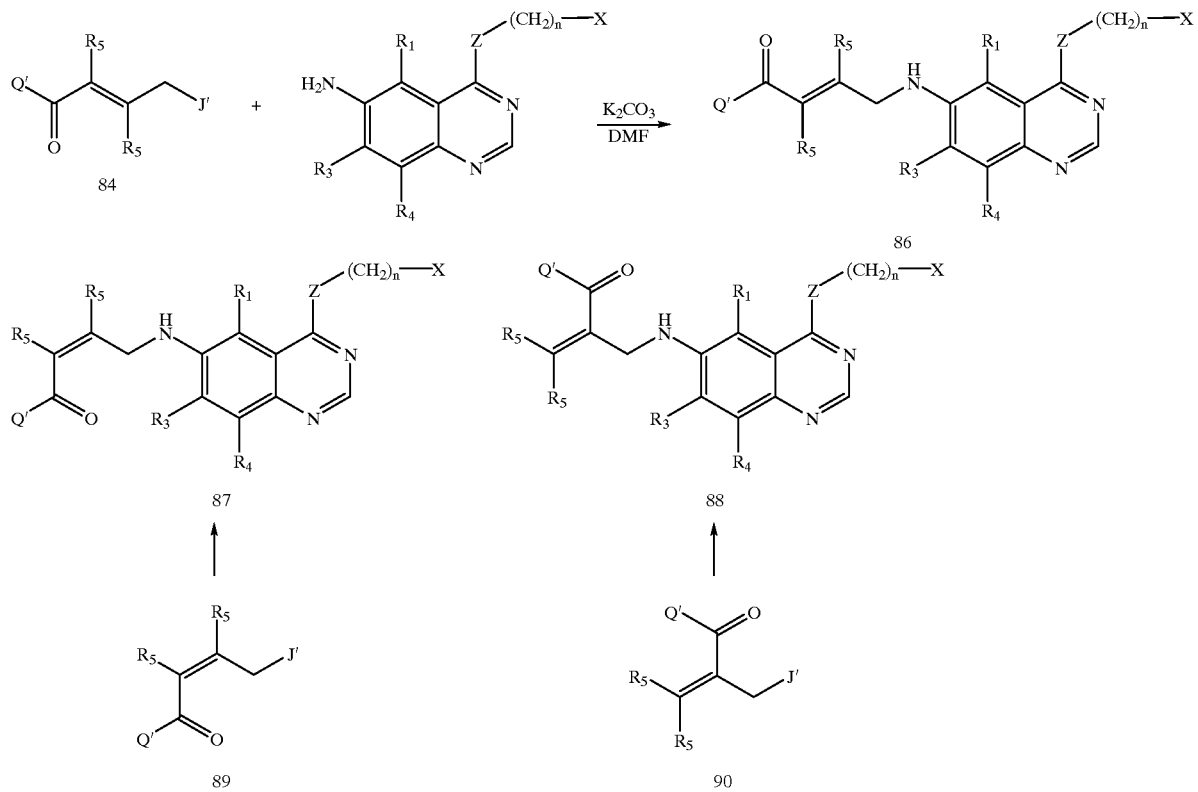

Compounds of this invention represented by Formula 93 can be prepared as shown in Flowsheet 14 wherein $R_1$, $R_3$, $R_4$, $R_5$, X, Z, and n are as defined above. The reaction of reagent 91 with the 6-amino-quinazolines 92 is accomplished using an excess of an organic base such as triethylamine and an inert solvent such as tetrahydrofuran to give compounds of this invention represented by Formula 93.

FLOWSHEET 14

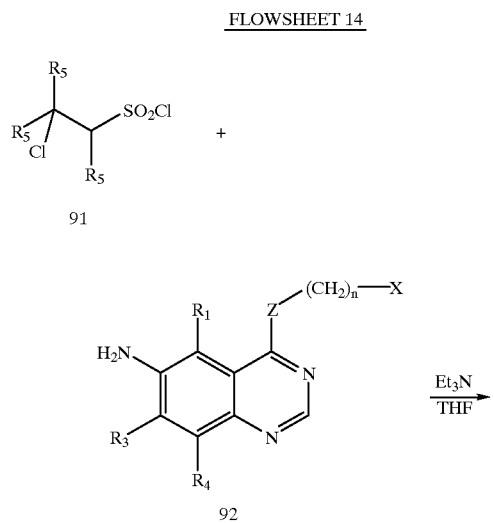

-continued

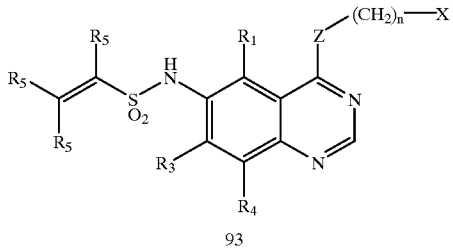

There are certain functional group manipulations that are useful to prepare the compounds of this invention that can be applied to various intermediate quinazolines as well as to the final compounds of this invention. These manipulations refer to the substituents $R_1$, $R_3$, or $R_4$ that are located on the quinazolines shown in the above Flowsheets. Some of these functional group manipulations are described below:

Where one or more of $R_1$, $R_3$, or $R_4$ is a nitro group, it can be converted to the corresponding amino group by reduction using a reducing agent such as iron in acetic acid or by catalytic hydrogenation. Where one or more of $R_1$, $R_3$, or $R_4$ is an amino group, it can be converted to the corresponding dialkyamino group of 2 to 12 carbon atoms by alkylation with at least two equivalents of an alkyl halide of 1 to 6 carbon atoms by heating in an inert solvent or by reductive alkylation using an aldehyde of 1 to 6 carbon atoms and a reducing agent such as sodium cyanoborohydride. Where one or more of $R_1$, $R_3$, or $R_4$ is a methoxy group, it can be converted to the corresponding hydroxy group by reaction with a demethylating agent such as boron tribromide in an inert solvent or by heating with pyridinium chloride with or without solvent. Where one or more of $R_1$, $R_3$, or $R_4$ is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a basic catalyst such as triethylamine or pyridine. Where one or more of $R_1$, $R_3$, or $R_4$ is an amino group, it can be converted to the corresponding alkyamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof. Where one or more of $R_1$, $R_3$, or $R_4$ is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a catalyst. Where one or more of $R_1$, $R_3$, or $R_4$ is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a catalyst. Where one or more of $R_1$, $R_3$, or $R_4$ is hydroxy, it can be converted to the corresponding alkynoyloxy group of 1–6 carbon atoms by reaction with an appropriate carboxylic acid chloride, anhydride, or mixed anhydride in a inert solvent using pyridine or a trialkylamine as a catalyst. Where one or more of $R_1$, $R_3$, or $R_4$ is carboxy or a carboalkoxy group of 2–7 carbon atoms, it can be converted to the corresponding hydroxymethyl group by reduction with an appropriate reducing agent such as borane, lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorous pentachloride to give a chloromethyl group. The hydroxymethyl group can be acylated with an appropriate acid chloride, anhydride, or mixed anhydride in an inert solvent using pyridine or a trialkylamine as a catalyst to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms. Where one or more of $R_1$, $R_3$, or $R_4$ is a halomethyl group, it can be converted to an alkoxymethyl group of 2–7 carbon atoms by displacing the halogen atom with a sodium alkoxide in an inert solvent. Where one or more of $R_1$, $R_3$, or $R_4$ is a halomethyl group, it can be converted to an aminomethyl group, N-alkylaminomethyl group of 2–7 carbon atoms or N,N-dialkylaminomethyl group of 3–14 carbon atoms by displacing the halogen atom with ammonia, a primary, or secondary amine, respectively, in an inert solvent.

In addition to the methods described herein above, there a number of patent applications that describe methods that are useful for the preparation of the compounds of this invention. The chemical procedures described in the application WO-9633981 can be used to prepare the quinazoline intermediates used in this invention wherein $R_1$, $R_3$, or $R_4$ are alkoxyalkylamino groups. The chemical procedures described in the application WO-9633980 can be used to prepare the quinazoline intermediates used in this invention wherein $R_1$, $R_3$, or $R_4$ are aminoalkylalkoxy groups. The chemical procedures described in the application WO-9633979 can be used to prepare the quinazoline intermediates used in this invention wherein $R_1$, $R_3$, or $R_4$ are alkoxyalkylamino groups. The chemical procedures described in the application WO-9633978 can be used to prepare the quinazoline intermediates used in this invention wherein $R_1$, $R_3$, or $R_4$ are aminoalkylamino groups. The chemical procedures described in the application WO-9633977 can be used to prepare the quinazoline intermediates used in this invention wherein $R_1$, $R_3$, or $R_4$ are aminoalkylalkoxy groups. Athough the above patent applications describe compounds where the indicated funtional group have been introduced onto the 6-position of the quinazoline, the same chemistry can be used to introduce the same groups unto positions occupied by the $R_1$, $R_3$, and $R_4$ substituents of the compounds of this invention.

Representative compounds of this invention were evaluated in several standard pharmacological test procedures that showed that the compounds of this invention possess significant activity as inhibitors of protein tyrosine kinases, and are antiproliferative agents. Based on the activity shown in the standard pharmacological test procedures, the compounds of this invention are therefore useful as antineoplastic agents. The test procedures used and results obtained are shown below.

Inhibition of Epidermal Growth Factor Receptor Kinase (EGF-R)

Test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme was obtained as a membrane extract of A431 cells (American Type Culture Collection, Rockville, Md.). A431 cells were grown in T175 flasks to 80% confluency. The cells were washed twice with phosphate buffered saline (PBS) without $Ca^{2+}$. Flasks were rotated for 1.5 hours in 20 mL PBS with 1.0 mM ethylenediaminetetraacetic acid (EDTA) at room temperature and centrifuged at 600 g for 10 minutes. The cells were solubilized in 1 mL per $5 \times 10^6$ cells of cold lysis buffer {10 mM 4-(2-hydroxyethyl)-1-piperazineethanesulfonic acid (HEPES), pH 7.6, 10 mM NaCl, 2 mM EDTA, 1 mM phenylmethylsulfonyl-fluoride (PMSF), 10 mg/mL aprotinin, 10 mg/mL leupeptin, 0.1 mM sodium orthovanadate} in a Dounce homogenizer with 10 strokes on ice. The lysate was centrifuged at 600 g for 10 minutes first to clear cell debris and the supernatant further centrifuged at 100,000 g for 30 min at 4° C. The membrane pellet was suspended in 1.5 mL HNG buffer (50 mM HEPES, pH 7.6, 125 mM NaCl, 10% glycerol). The membrane extract was divided into aliquots, immediately frozen in liquid nitrogen and stored at −70° C.

Test compounds were made into 10 mg/mL stock solutions in 100% dimethylsulfoxide (DMSO). Prior to experiment, stock solutions were diluted to 500 uM with 100% DMSO and then serially diluted to the desired concentration with HEPES buffer (30 mM HEPES, pH 7.4).

An aliquot of the A431 membrane extract (10 mg/mL) was diluted in 30 mM HEPES (pH 7.4) to give a protein concentration of 50 ug/mL. To 4 $\mu$l of enzyme preparation, EGF (1 $\mu$l at 12 $\mu$g/mL) was added and incubated for 10 min on ice followed by 4 $\mu$l of the test compound or buffer; this mix was incubated on ice for 30 min. To this was added the $^{33}$P-ATP (10 mCi/mL) diluted 1:10 in assay buffer along with the substrate peptide at a concentration of 0.5 mM (control reactions get no test compound) and the reaction was allowed to proceed for 30 min at 30° C. The reaction was stopped with 10% TCA and left on ice for at least 10 min after which tubes were microcentrifuged at full speed for 15 min. Twenty microliter portions of the supernatants were spotted on P81 phosphocellulose discs and washed twice in 1% acetic acid then water for 5 min each followed by scintillation counting. The inhibition data for representative compounds of the invention are shown below in TABLE 1. The $IC_{50}$ is the concentration of test compound needed to reduce the total amount of phosphorylated substrate by 50%. The % inhibition of the test compound was determined for at least three different concentrations and the $IC_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabled ATP ($\gamma$-$^{33}$P) incorporated onto the RR-SRC peptide substrate by the enzyme after 30 minutes at 30° C. in the presence of test compound as measured by liquid scintillation counting. CPM(control) is in units of counts per minute and was a number expressing the amount of radiolabled ATP ($\gamma$-$^{33}$P) incorporated onto the RR-SRC peptide substrate by the enzyme after 30 minutes at 30° C. in the absence of test compound as measured by liquid scintillation counting. The CPM values were corrected for the background counts produced by ATP in the absence of the enzymatic reaction. The $IC_{50}$ values reported in TABLE 1 are averages of the number of tests conducted.

TABLE 1

(cell membrane preparation)
Inhibition of Epidermal Growth Factor Receptor Kinase

| Compound | IC50 ($\mu$M) | Number of Tests |
|---|---|---|
| Example 59 | 0.00126 | 4 |
| Example 60 | 0.034 | 3 |
| Example 69 | 1 × 10−6 | 2 |
| Example 71 | 7 × 10−6 | 3 |
| Example 73 | 0.00084 | 3 |
| Example 75 | 0.001 | 6 |
| Example 77 | 0.003 | 1 |
| Example 79 | 0.0014 | 3 |

Inhibition of Epidermal Growth Factor Receptor Kinase (EGF-R) Using Recombinant Enzyme Representative test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this assay is the His-tagged cytoplasmic domain of EGFR. A recombinant baculovirus (vHcEGFR52) was constructed containing the EGFR cDNA encoding amino acids 645–1186 preceded by Met-Ala-(His)$_6$. Sf9 cells in 100 mm plates were infected at an moi of 10 pfu/cell and cells were harvested 48 h post infection. A cytoplasmic extract was prepared using 1% Triton X-100 and applied to Ni-NTA column. After washing the column with 20 mM imidazole, HcEGFR was eluted with 250 mM imidazole (in 50 mM $Na_2HPO_4$, pH 8.0, 300 mM NaCl). Fractions collected were dialyzed against 10 mM HEPES, pH 7.0, 50 mM NaCl, 10% glycerol, 1 ug/mL antipain and leupeptin and 0.1 mM Pefabloc SC. The protein was frozen in dry ice/methanol and stored −70° C.

Test compounds were made into 10 mg/mL stock solutions in 100% dimethylsulfoxide (DMSO). Prior to experiment, stock solutions were diluted to 500 uM with 100% DMSO and then serially diluted to the desired concentration with HEPES buffer (30 mM HEPES pH 7.4).

For the enzyme reaction, 10 uL of each inhibitor (at various concentrations) were added to each well of a 96-well plate. To this was added 3 uL of enzyme (1:10 dilution in 10 mM HEPES, pH 7.4 for final conc. of 1:120). This was allowed to sit for 10 min on ice and was followed by the addition of 5 ul peptide (80 uM final conc.), 10 ul of 4× Buffer (Table A), 0.25 uL $^{33}$P-ATP and 12 uL $H_2O$. The reaction was allowed to run for 90 min at room temperature and was followed by spotting the entire volume on to precut P81 filter papers. The filter discs were washed 2× with 0.5% phosphoric acid and radioactivity was measured using a liquid scintillation counter.

| Reagent | Final | 100 Rxns |
|---|---|---|
| 1M HEPES (pH 7.4) | 12.5 mM | 50 uL |
| 10mM $Na_3VO_4$ | 50 uM | 20 uL |
| 1M $MnCl_2$ | 10 mM | 40 uL |
| 1mM ATP | 20 uM | 80 uL |
| $^{33}$P-ATP | 2.5 uCi | 25 uL |

The inhibition data for representative compounds of the invention are shown below in TABLE 2. The $IC_{50}$ is the concentration of test compound needed to reduce the total amount of phosphorylated substrate by 50%. The % inhibition of the test compound was determined for at least three different concentrations and the $IC_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabled ATP ($\gamma$-$^{33}$P) incorporated onto the RR-SRC peptide substrate by the enzyme after 90 minutes at room temperature in the presence of test compound as measured by liquid scintillation counting. CPM(control) is in units of counts per minute and was a number expressing the amount of radiolabled ATP ($\gamma$-$^{33}$P) incorporated into the RR-SRC peptide substrate by the enzyme after 90 minutes at room temperature in the absence of test compound as measured by liquid scintillation counting. The CPM values were corrected for the background counts produced by ATP in the absence of the enzymatic reaction. The $IC_{50}$ values reported in TABLE 2 are averages of the number of tests conducted.

TABLE 2

(recombinant enzyme)
Inhibition of Epidermal Growth Factor Receptor Kinase

| Compound | IC50 ($\mu$M) | Number of Tests |
|---|---|---|
| Example 12 | 0.005 | 2 |
| Example 15 | 0.006 | 1 |
| Example 16 | 0.008 | 1 |
| Example 19 | 0.05 | 2 |
| Example 21 | 0.065 | 2 |
| Example 23 | 0.00031 | 2 |
| Example 25 | 0.014 | 2 |
| Example 28 | 0.0055 | 2 |
| Example 31 | 0.002 | 2 |
| Example 34 | 0.035 | 2 |

TABLE 2-continued (recombinant enzyme)
Inhibition of Epidermal Growth Factor Receptor Kinase

| Compound | IC50 ($\mu$M) | Number of Tests |
|---|---|---|
| Example 37 | 0.0045 | 2 |
| Example 40 | 0.0035 | 2 |
| Example 43 | 0.004 | 1 |
| Example 47 | 0.0003 | 1 |
| Example 48 | 0.002 | 1 |
| Example 49 | 0.1 | 1 |
| Example 50 | 0.0004 | 1 |
| Example 51 | 0.007 | 1 |
| Example 52 | 0 | 1 |
| Example 53 | 0.06 | 2 |
| Example 55 | 0.002 | 1 |
| Example 57 | 0.008 | 1 |
| Example 58 | 0.08 | 1 |
| Example 61 | 0.08 | 1 |
| Example 63 | $5 \times 10^{-6}$ | 2 |
| Example 65 | $1 \times 10^{-5}$ | 1 |
| Example 66 | $8 \times 10^{-7}$ | 2 |
| Example 67 | $7.5 \times 10^{-5}$ | 2 |
| Example 81 | 0.0007 | 2 |
| Example 82 | 0.001 | 1 |

Inhibition of Cancer Cell Growth

Human tumor cell lines were plated in 96-well plates (250 $\mu$A/well, $1-6 \times 10^4$ cells/mL) in RPMI 1640 medium, containing 5% FBS (Fetal Bovine Serum). Twenty four hours after plating, test compounds were added at five log concentrations (0.01–100 mg/mL) or at lower concentrations for the more potent compounds. After 48 hours exposure to test compounds, cells were fixed with trichloroacetic acid, and stained with Sulforhodamine B. After washing with trichloroacetic acid, bound dye was solubilized in 10 mM Tris base and optical density was determined using plate reader. Under conditions of the assay the optical density is proportional to the number of cells in the well. $IC_{50}$s (concentrations causing 50% inhibition of cell growth) were determined from the growth inhibition plots. The test procedure is described in details by Philip Skehan et. al, *J.Natl. Canc. Inst.*, 82, 1107–1112 (1990). These data are shown below in TABLE 3. Information about some of the cell lines used in these test procedures is available from the American Type Tissue Collection: Cell Lines and Hybridomas, 1994 Reference Guide, 8th Edition.

TABLE 3

Inhibition of Cancer Cell Growth as Measured by Cell Number ($IC_{50}$ $\mu$g/mL)

| Example | MB435 | A2780S | A2780DDP | MCF7 | SW620 | LOX | A431 | SKBR3 |
|---|---|---|---|---|---|---|---|---|
| 12 | 0.39 | 0.03 | 0.07 | 0.49 | 0.06 | 0.04 | 0.03 | <0.01 |
| 15 | 0.42 | 0.02 | 0.05 | 0.45 | 0.02 | 0.03 | 0.04 | 0.38 |
| 16 | 0.49 | 0.03 | 0.04 | 0.61 | 0.05 | 0.05 | 0.18 | <0.01 |
| 19 | 5.95 | 4.37 | 3.32 | 6.36 | 1.10 | 3.55 | 0.02 | 0.003 |
| 21 | 1.43 | 0.34 | 0.28 | 2.97 | 0.09 | 0.37 | 0.30 | 0.37 |
| 23 | 0.80 | 0.12 | 0.06 | 0.50 | 0.06 | 0.02 | 0.05 | 0.06 |
| 25 | 0.05 | 0.04 | 0.04 | 0.74 | 0.07 | 0.1 | 0.06 | 0.004 |
| 28 | 1.61 | 0.84 | 0.56 | 3.09 | 2.38 | 1.94 | 0.60 | 0.10 |
| 31 | 0.7 | 0.2 | 0.6 | NA | 0.4 | 0.5 | 0.01 | <0.01 |
| 47 | NA | 0.01 | 0.197 | 1.17 | 0.39 | 0.0772 | 0.023 | 0.496 |
| 48 | 5.48 | 4.74 | 3.71 | 5.42 | 2.81 | 3.55 | 3.11 | 3.79 |
| 49 | 5.20 | 4.81 | 3.16 | 6.72 | 3.61 | 3.48 | 2.83 | 3.57 |
| 50 | >100 | >100 | >100 | >100 | >100 | >100 | >100 | >100 |
| 51 | >100 | 56.85 | 6.92 | >100 | >100 | 56.45 | 6.84 | 6.21 |
| 52 | 26.81 | 27.04 | 41.15 | 53.08 | >100 | 7.60 | 8.42 | 38 |
| 53 | 4.31 | 2.89 | 4.73 | 5.09 | NA | 5.62 | 0.44 | NA |
| 55 | 2.8 | 0.02 | 0.5 | 5.0 | 0.1 | 0.2 | 0.4 | 0.3 |
| 57 | 5.7 | 0.7 | 2.5 | 8.7 | 1.8 | 0.9 | 2.8 | 1.2 |
| 59 | NA | 0.424 | 0.603 | 1.58 | 0.581 | 0.482 | 0.315 | NA |
| 60 | NA | 0.749 | 0.626 | 0.566 | 1.89 | 0.725 | 0.35 | NA |
| 61 | 4.35 | 1.86 | 1.39 | 3.62 | 0.43 | 0.50 | 0.73 | 0.04 |
| 63 | 4.5 | 0.8 | 4.0 | 17 | 5.5 | 3.9 | 0.6 | 10.01 |
| 65 | 13 | 5.2 | 6.5 | 42 | 8.1 | 5.3 | 3.2 | 0.3 |
| 66 | 5.4 | 3.9 | 5.1 | 7.6 | 5.1 | 4.9 | 0.007 | <0.01 |
| 67 | 45 | 22 | 43 | 59 | 52 | 46 | 0.01 | <0.01 |
| 69 | NA | 0.896 | 3.32 | 3.65 | 0.988 | 5.54 | 1.61 | NA |
| 71 | NA | 2.55 | 3.27 | 2.19 | 3.97 | 4.05 | 0.707 | NA |
| 73 | NA | 1.77 | 3.0 | 5.04 | 3.65 | 3.1 | 1.07 | NA |
| 75 | NA | 2.6 | 3.11 | 2.65 | 4.94 | 3.78 | 1.75 | NA |
| 79 | NA | 0.922 | 2.42 | 2.73 | 4.53 | 2.84 | 0.981 | NA |
| 81 | NA | 0.257 | 0.311 | 1.03 | 0.584 | 0.386 | 0.34 | 0.306 |
| 82 | NA | 0.0626 | 0.112 | 0.81 | 0.53 | 0.382 | 0.025 | 0.269 |

In Vivo Inhibition of the Growth of Human Epidermoid Tumors (A431)

BALB/c nu/nu female mice (Charles River, Wilmington, Mass.) were used in the in vivo standard pharmacological test procedures. Human epidermoid carcinoma cells A-431 (American Type Culture Collection, Rockville, Md. # CRL-155) were grown in vitro as described above. A unit of $5 \times 10^6$ cells were injected SC into mice. When tumors attained a mass of between 100 and 150 mg, the mice were randomized into treatment groups (day zero). Mice were treated IP or PO once a day either on days 1, 5, and 9 or on days 1 through 10 post staging with doses of either 80, 40 or 20, or 10 mg/kg/dose of the compound to be evaluated in 0.2% Klucel. Control animals received no drug. Tumor mass was determined every 7 days [(length×width$^2$)/2] for 28 days post staging. Relative tumor growth (Mean tumor mass on day 7, 14, 21, and 28 divided by the mean tumor mass on day zero) is determined for each treatment group. The %T/C (Tumor/Control) is determined by dividing the relative tumor growth of the treated group by the relative tumor growth of the placebo group and multiplying by 100. A compound is considered to be active if the %T/C is found to be ≦100%.

The ability of the compound of Example 21 to inhibit the growth of human epidermoid tumors (A431) in vivo demonstrated below in TABLE 4 below.

TABLE 4

In Vivo Inhibition of the Growth of Human Epidermoid Tumors (A431) in Mice by the Compound of Example 21

| Dose (mg/kg/dose)[a] PO | RTG[b] Day 7 | % T/C[c] | RTG[b] Day 16 | % T/C[c] | RTG[b] Day 21 | % T/C[c] | RTG[b] Day 28 | % T/C[c] | S/T[d] |
|---|---|---|---|---|---|---|---|---|---|
| Control | 5.68 |  | 10.27 |  | 12.86 |  | 13.94 |  | 10/10 |
| 40 | 4.51 | 79 | 8.58 | 84 | 8.54 | 66 | 9.08 | 65 | 5/5 |
| 20 | 5.67 | 100 | 8.39 | 82 | 8.27 | 64 | 10.07 | 72 | 5/5 |
| 10 | 3.96 | 70 | 5.80 | 56 | 5.36 | 42 | 5.92 | 42 | 5/5 |

[a]Drugs administered IP on days 1 through 10.
[b]Relative Tumor Growth = Mean Tumor Mass on Day 7, 14, 21, 28/Mean Tumor Mass on Day 0
[c]% T/C = Relative Tumor Growth of Treated Group/Relative Tumor Growth of Placebo Group X 100
[d]S/T = No. Survivors/No. Treated on Day +28 post tumor staging.

As indicated by the results presented in TABLE 4, the compound of Example 21 is an effective inhibitor of tumor growth in vivo and is therfore useful for the treatment of cancer.

The ability of the compound of Example 25 to inhibit the growth of human epidermoid tumors (A431) in vivo demonstrated below in TABLE 5 below As indicated by the results presented in TABLE 5, the compound of Example 25 is an effective inhibitor of tumor growth in vivo and is therfore useful for the treatment of cancer.

Based on the results obtained for representative compounds of this invention, the compounds of this invention are particularly useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. In addition, the compounds of this invention are useful in treating, inhibiting the growth of, or eradicating neoplasms of the breast and other organs that express the receptor protein produced by the erbB2 (Her2) oncogene. In addition, the compounds of this invention are useful in treating, inhibiting the progression of, or eradicating certain kidney diseases such as polycystic kidney disease that involve, at least in part, the deregulation of EGFR.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in

TABLE 5

In Vivo Inhibition of the Growth of Human Epidermoid Tumors (A431) in Mice by the Compound of Example 25

| Compound | RTG[b] Day 7 | % T/C[c] | RTG[b] Day 14 | % T/C[c] | RTG[b] Day 21 | % T/C[c] | RTG[b] Day 28 | % T/C[c] | S/T[d] |
|---|---|---|---|---|---|---|---|---|---|
| Control | 2.76 |  | 7.07 |  | 11.75 |  | 17.13 |  | 8/10 |
| *40 PO | 1.96 | 71 | 2.33 | 33 | 4.68 | 40 | 8.84 | 52 | 4/5 |

[a]Drugs on days 1 through 1 through 10*.
[b]Relative Tumor Growth = Mean Tumor Mass on Day 7, 14, 21, 28/Mean Tumor Mass on Day 0
[c]% T/C = Relative Tumor Growth of Treated Group/Relative Tumor Growth of Placebo Group X 100
[d]S/T = No. Survivors/No. Treated on Day +28 post tumor staging.

combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, and antiestrogens such as tamoxifen.

The preparation of representative examples of the compounds of this invention is described below.

EXAMPLE 1

N'-(2-Cyano-4-nitrophenyl)-N,N-dimethylformamidine

A 40.8 g portion of 5-nitro-anthranilonitrile and 40 mL of N,N-dimethylformamide dimethyl acetal were heated on a steam bath for 2 hours. The solvents were removed at reduced pressure and the residue was taken up in methylene chloride. After passing this solution through Magnesol the solvent was removed. After washing with ether 50.8 g of N'-(2-cyano-4-nitrophenyl)-N,N-dimethylformamidine was obtained.

EXAMPLE 2

N-(3-Bromophenyl)-6-nitro-4-quinazolinamine

A solution of 23.74 mL of 3-bromo aniline and 40.5 g N'-(2-cyano-4-nitrophenyl)-N,N-dimethylformamidine in 100 mL of glacial acetic acid was stirred and heated in an oil bath at 148° C. for 1.5 hours. On cooling, filtration of the resulting solid gives a quantitative yield of N-(3-bromophenyl)-6-nitro-4-quinazolinamine: mp=267–270° C.; mass spectrum (m/e): 345.

EXAMPLE 3

N-(3-Bromophenyl)-4,6-quinazolindiamine

A mixture of 34.5 g of N-(3-bromophenyl)-6-nitro4-quinazolinamine and 16.8 g of iron powder in 150 mL of ethanol and 150 mL of glacial acetic acid was heated in an oil bath at 120° C. for 2 hours. After filtration of the solid, solid sodium carbonate was added to the filtrate giving a solid. This was filtered, and the solid was extracted with methanol. The extracts were treated with charcoal and evaporated to a solid. After washing the solid with ether 27.5 g of N-(3-bromophenyl)-4,6-quinazolindiamine was obtained: mass spectrum (m/e): 315.

EXAMPLE 4

4-[[4-[(3-Bromophenyl)amino]-6-quinazolinyl] amino]-4-oxo-(Z)-2-butenoic acid

A 15 mL portion of pyridine was added to 1.6 g of N-(3-bromophenyl)-4,6-quinazolindiamine and 0.6 g of maleic anhydride. After stirring overnight, the solvents were removed on the rotary evaporator. The solid was taken up in about 400 mL of hot ethanol and the insoluble material filtered to give 0.33 g of 4-[[4-[(3-Bromophenyl)amino]-6-quinazolinyl]amino]-4-oxo-(Z)-2-butenoic acid: mass spectrum (m/e): M+H 413, 415.

EXAMPLE 5

6-amino-4-chloroquinazoline

A mixture consisting of 3.25 g of 4-chloro-6-nitroquinazoline, 10.8 g of sodium hydrosulfite, and 0.3 g of the phase transfer catalyst $(C_8H_{17})_3NCH_3^+Cl^-$ in 97 mL of tetrahydrofuran and 32 mL of water was stirred rapidly for 2 hours. The mixture was diluted with ether and the organic layer was separated. The organic solution was washed with brine and then dried over magnesium sulfate. The solution was passed through a small column of silica gel. The solvent was removed at 30° C. at reduced pressure giving 6-amino-4-chloroquinazoline which is used in the next step without additional purification.

EXAMPLE 6

[4-chloro-6-quinazolinyl]-2-butynamide

A solution of 1.64 g of 2-butynoic acid in 46 mL of tetrahydrofuran was cooled in an ice bath. A 2.34 mL portion of isobutyl chloroformate followed by a 4.13 mL portion of N-methyl morpholine were added. After about 10 minutes, this was poured into a solution of 6-amino-4-chloroquinazoline in 46 mL tetrahydrofuran. This mixture was stirred at room temperature for 2 hours. The mixture was poured into a mixture of brine and saturated sodium bicarbonate and extracted with ether. The ether solution was dried over magnesium sulfate and filtered. The solvent was removed giving [4-chloro-6-quinazolinyl]-2-butynamide as colored oil that was used in the next step without additional purification.

EXAMPLE 7

N-[4-[(3-Bromophenyl)amino]-6-quinazolinyl]-2-butynamide

A solution consisting of 1.76 g of [4-chloro-6-quinazolinyl]-2-butynamide and 1.23 g of 3-bromo aniline was refluxed under an inert atmosphere in 23 mL of isopropanol for 40 minutes. The mixture was cooled to room temperature and 200 mL of ether was added giving 0.4 g of N-[4-[(3-bromophenyl)amino]-6-quinazolinyl]-2-butynamide as the hydrochloride salt. Neutralizing with sodium bicarbonate solution, extracting with ethyl acetate, removal of the solvent, and recyrstallization from 1-butanol gives N-[4-[(3-bromophenyl)amino]-6-quinazolinyl]-2-butynamide as the free base.

EXAMPLE 8

N'-(4-Amino-2-cyanophenyl)-N,N-dimethylformamidine

A solution of 6.0 g (27.5 mmol) of N'-(2-cyano-4-nitrophenyl)-N,N-dimethylformamidine, 33.9 g (41.8 mL, 412.4 mmol) of cyclohexene, and 0.6 g of 10% Pd/C in 360 mL of methanol was refluxed for 4 hrs. The hot mixture was filtered through Celite. Solvent was removed and the residue was recrystallized from chloroform-carbon tetrachloride giving 4.9 g (95%) of the title compound as a light gray crystalline solid. mass spectrum (m/e): 188.9 (M+H, electrospray).

EXAMPLE 9

N-[3-Cyano-4-[[(dimethylamino)methylene]amino] phenyl]-2-butynamide

To a solution of 2.01 g (23.9 mmol) of 2-butynoic acid and 2.9 mL (22.3 mmol) isobutyl chloroformate in 30 mL tetrahydrofuran was stirred at 0° C. under nitrogen as 2.42 g (2.63 mL, 22.3 mmol) of N-methyl morpholine was added over 3 min. After stirring for 15 min., a solution of N'-(4-amino-2-cyanophenyl)-N,N-dimethylformamidine and 1.6 g (1.75 mL, 15.9 mmol) of N-methyl morpholine in 25 mL tetrahydrofuran was added over 4 min. The mixture was stirred 30 min. at 0° C. and 30 min. at room temperature. The mixture was diluted with 70 mL of ethyl acetate and poured into a mixture of brine and saturated sodium bicarbonate. The organic layer was dried ($MgSO_4$) and filtered through a pad of silica gel. The solvent was removed and the residue was stirred with 50 mL of ether. The suspended solid was collected to give 3.61 g (89%) of an off-white solid. mass spectrum (m/e): 255.0 (M+H, electrospray).

EXAMPLE 10

N-[4-[(3-Bromophenyl)amino]-6-quinazolinyl]-2-butynamide

A solution of 3.0 g (11.8 mmol) of N-[3-cyano-4-[[(dimethylamino)methylene]amino]phenyl]-2-butynamide and 2.23 g (12.98 mmol) of 3-bromo aniline in 18 mL of acetic acid was refluxed gently with stirring under nitrogen for 1 hr 15 min. The mixture was cooled in an ice bath and a solid mass formed. The solid was collected by filtration and washed with ether-acetonitrile 1:1 to give a yellow solid which was recrystallized from ethanol giving 2.51 g of N-[4-[(3-bromophenyl)amino]-6-quinazolinyl]-2-butynamide: mass spectrum (m/e): 381, 383.

EXAMPLE 11

4-Chloro-but-2-yanoic acid

Propargyl chloride (2 mL, 26.84 mmol) was dissolved in 40 mL of tetrahydrofuran under nitrogen and cooled to −78° C. After addition of n-butyllithium (5.4 mL, 13.42 mmol, 2.5 M in n-hexane) and stirred for 15 min, a stream of dry carbon dioxide was passed through it at −78° C. for two hours. The reaction solution was filtered and neutralized with 3.5 mL of 10% sulfuric acid. After evaporation of the solution, the residue was extracted with ether. The ether solution was washed with saturated brine solution, and dried over sodium sulfate. After evaporation of the dry ether solution, 0.957 g (60%) of an oil product was obtained: ESMS m/z 116.6 (M−H$^+$).

EXAMPLE 12

4-Chloro-but-2-ynoic acid [4-(3-bromo-phenylamino)-quinazolin-6yl]-amide

Isobutyl chloroformate (0.625 g, 4.58 mmol) and N-methylmorpholine (0.506 g, 5.00 mmol) were added to an ice cold solution of 0.542 g (4.58 mmol) of 4-chloro-but-2-yanoic acid in 7mL of tetrahydrofuran under nitrogen. After stirring for 30min, a solution of 0.72 g (2.287 mmol) of N-(3-bromophenyl)-4,6-quinazolindiamine in 3.35 mL of pyridine was added and the mixture was stirred at 0° C. for 1 h. The reaction was quenched with ice water. The product was collected by filtration, washed with water and ether, and dried in vacuo to give 0.537 g of brown solid; ESMS m/z 417.0 (M+H$^+$).

EXAMPLE 13

3-(tert-Butyl-dimethyl-silanyloxy)-but-2-yne

To an ice cold solution of tert-butydimethylsilyl chloride (31.8 g, 0.21 mmol), triethylamine (23.5 g, 0.23mol), 4-N, N-dimethylpyridine (0.103 g, 0.83 mmol) and methylene chloride (65 mL), was added dropwise propargyl alcohol (10.6 g, 0.192 mol) in 15 mL of methylene chloride. After stirring at room temperature for 21 hrs, the reaction solution was washed with brine and dried over sodium sulfate. After distillation, 22.87 g (0.135 mol) of the product was obtained; CIMS⁻ m/z 171.2 (M+H⁺).

Ref: Tetrahedron 37, 3974(1981)

EXAMPLE 14

4-(tert-Butyl-dimethyl-silanyloxy)-but-2-ynoic acid

A solution of 3-(tert-Butyl-dimethyl-silanyloxy)-but-2-yne (5 g, 29.4 mmol) in tetrahydrofuran (50 mL) was dropwise added into methylmagnesium bromide solution (11 mL, 294 mmol, 3M in ethyl ether) at 0° C. After stirring at 0° C. for 1.5 hr and then at room temperature for 2.5 hr, a stream of dry carbon dioxide was passed through the pale yellow solution for two hours. The solution was treated with an aqueous solution of ammonium chloride (2 g in 9 mL of water) and 200 mL of ethyl acetate. The mixture was titrated with 1% hydrochloric acid to pH 5.0. The ethyl acetate layer was then washed with water and dried over sodium sulfate. After evaporation, 6.28 g of product was obtained: HRMS m/z 215.1096 (M+H⁺).

EXAMPLE 15

4-(tert-Butyl-dimethyl-silanyloxy)-but-2-ynoic acid [4-(3-bromo-phenylamino)-quinazolin-6-yl]-amide Isobutyl chloroformate (0.39 g, 4.68) and N-methylmorpholine (0.555 g, 5.487 mmol) were added to an ice cold solution of 1 g (4.673 mmol) of 4-(tert-Butyl-dimethyl-silanyloxy)-but-2-ynoic acid in 32 mL of tetrahydrofuran under $N_2$. After stirring for 30 min, a solution of 0.9797 g 3.108 mmol) of N-(3-bromophenyl)-4,6-quinazolindiamine in 4 mL of pyridine was added and the mixture was stirred at 0° C. for 1 h. The reaction was quenched with ice water. The reaction solution was poured into ethyl acetate and washed with saturated sodium bicarbonate and brine. The product was collected and purified by flash column chromatography (60% ethyl acetate in hexane) to give 0.8 g of 4-(tert-Butyl-dimethyl-silanyloxy)-but-2-ynoic acid [4-(3-bromo-phenylamino)-quinazolin-6-yl]-amide: HRMS m/z 511.1145 (M+H⁺).

EXAMPLE 16

4-Hydroxy-but-2-ynoic acid [4-(3-bromo-phenylamino)-quinazolin-6-yl]-amide 4-(tert-Butyl-dimethyl-silanyloxy)-but-2-ynoic acid [4-(3-bromo-phenylamino)-quinazolin-6-yl]-amide (300 mg, 0.587 mmol) was dissolved in 60 mL of solution (acetic acid:water:tetrahydrofuran=3:1:1) and stirred at room temperature overnight. The reaction solution was treated with cold brine solution and extracted with ethyl acetate. The ethyl acetate solution was washed with sodium bicarbonate solution and brine. Evaporation of the dry ethyl acetate solution yielded 275 mg of the product: HRMS m/z 397.0258 (M+H⁺).

EXAMPLE 17

Hexa-2,4-dienoic acid amide

Propargyl bromide (27.3 g, 230 mmol) was added dropwise to a mixture of morpholine (20 g, 230 mmol) and cesium carbonate (75 g, 230 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 18 g of hexa-2,4-dienoic acid amide: mass spectrum (m/e): M+H 126.

EXAMPLE 18

4-Morpholin-4-yl-but-2-ynoic acid n-Butyl lithium in hexane (51 mL, 2.5M in n-hexane) was slowly added to hexa-2,4-dienoic acid amide (16 g, 128 mmol) in 200 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 13 g of 4-morpholin-4-yl-but-2-ynoic acid: mass spectrum (m/e) :M−H 168.

EXAMPLE 19

4-Morpholin-4-yl-but-2-ynoic acid [4-(3-bromo-phenylamino)-quinazolin-6-yl]-amide Isobutyl chloroformate (0.343 g, 2.5 mmol) and N-methylmorpholine (0.322 g, 3.18 mmol) were added to an ice cold solution of 0.540 g (3.18 mmol) of 4-morpholin-4-yl-but-2-ynoic acid in 50 mL of tetrahydrofuran under nitrogen. After stirring for 30 min, a solution of 0.500 g of N-(3-bromophenyl)-4,6-quinazolindiamine in 10 mL of pyridine was added and the mixture was stirred at 0° C. for 2 hr. The reaction was then quenched with ice water, poured into saturated sodium bicarbonate, and the product was extracted with ethyl acetate. Chromatography of the extract on silica gel, eluting with methanol/ethyl acetate (15:85), gave 0.240 g of 4-morpholin-4-yl-but-2-ynoic acid [4-(3-bromo-phenylamino)-quinazolin-6-yl]-amide: mass spectrum (m/e): M+H 466.

EXAMPLE 20

4-Dimethylamino-but-2-ynoic acid n-Butyl lithium in hexane (96 mL, 2.5 M in n-hexane) was slowly added to 1-dimethylamino-2-propyne (20 g, 240 mmol) in 100 mL of tetrahydrofuran under nitrogen. The mixture was stirred for 1 h at −78° C., then dry carbon dioxide was pass through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15.6 g of 4-dimethylamino -but-2-ynoic acid: mass spectrum (m/e) :M−H 126.

EXAMPLE 21

4-Dimethylamino-but-2-ynoic acid [4-(3-bromo-phenylamino)-quinazolin-6-yl]-amide Isobutyl chloroformate (0.235 g, 1.72 mmol) and N-methylmorpholine (0.534 g, 5.28 mmol) were added to an ice cold solution of 0.336 g (2.64 mmol) of 4-dimethylamino-but-2-ynoic acid in 30 mL of tetrahydrofuran under nitrogen. After stirring for 30 min, a solution of 0.416 g of N-(3-bromophenyl)-4,6-quinazolindiamine in 10 mL of pyridine was added and the mixture was stirred at 0° C. for 2 hr. The reaction was then quenched with ice water, poured into saturated sodium bicarbonate, and the product was extracted with ethyl acetate. Chromatography of the extract on silica gel, eluting with methanol/ethyl acetate (15:85), gave 0. 155 g of 4-dimethylamino-but-2-ynoic acid [4-(3-bromo-phenylamino)-quinazolin-6-yl]-amide: mass spectrum (m/e): M+H 424.

EXAMPLE 22

4-Methoxy-but-2-ynoic acid 3.0 M Methylmagnesium bromide in ether (93 mL) was slowly added to methyl propargyl ether (20 g, 280 mmol) in 300 mL of tetrahydrofuran under nitrogen. The mixture was stirred for 1 h at −78° C., then dry carbon dioxide was passed through overnight. The resulting solution was cooled to 0° C. and 125 mL of cold 10% sulfuric acid was added, keeping the temperature below 5° C. during the addition. The aqueous layer was extracted with ethyl acetate, then the ethyl acetate was evaporated, and the residue was distilled at reduced pressure (b.p. 87–90° C. at 0.3mmHg) to give 15.6 g of 4-dimethylamino-but-2-ynoic acid: mass spectrum (m/e):M−H 126.

EXAMPLE 23

4-Methoxy-but-2-ynoic acid [4-(3-bromo-phenylamino)-quinazolin-6-yl]-amide

Isobutyl chloroformate (0.432 g, 3.2 mmol) and N-methylmorpholine (0.959 g, 9.48 mmol) were added to an ice cold solution of 0.720 g (6.32 mmol) of 4-methoxy-but-2-ynoic acid in 30 mL of tetrahydrofuran under nitrogen. After stirring for 30 min, a solution of 0.500 g of N-(3-bromophenyl)-4,6-quinazolindiamine in 8 mL of pyridine was added and the mixture was stirred for 2 hr at 0° C. The reaction was then quenched with ice water, poured into saturated sodium bicarbonate, and the product was extracted with ethyl acetate. Chromatography of the extract on silica gel, eluting with methanol/ethyl acetate (15:85), gave 0.270 g of 4-Methoxy-but-2-ynoic acid [4-(3-bromo-phenylamino)-quinazolin-6-yl]-amide: mass spectrum (m/e): M+H 411.

EXAMPLE 24

4-Diethylamino-but-2-ynoic acid n-Butyl lithium in hexane (54 mL, 2.5M in n-hexane) was slowly added to 1-diethylamino-2-propyne (15 g, 135 mmol) in 60 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 9.2 g of 4-diethylamino-but-2-ynoic acid: mass spectrum (m/e) :M+H 156.

EXAMPLE 25

4-Diethylamino-but-2-ynoic acid[4-(3-bromo-phenylamino)-quinazolin-6-yl]-amide

Isobutyl chloroformate (0.975 g, 7.14 mmol) and N-methylmorpholine (1.500 g, 14.3 mmol) were added to an ice cold solution of 2.200 g (14.3 mmol) of 4-diethylamino-but-2-ynoic acid in 125 mL of tetrahydrofuran under nitrogen. After stirring for 30 min, a solution of 1.500 g of N-(3-bromophenyl)-4,6-quinazolindiamine in 12 mL of pyridine was added and the mixture was stirred for 2 hr at 0° C. The reaction was then quenched with ice water, poured into saturated sodium bicarbonate, and the product was extracted with ethyl acetate. Chromatography of the extract on silica gel, eluting with methanol/ethyl acetate (15:85), gave 0.750 g of 4-Ddimethylamino-but-2-ynoic acid [4-(3-bromo-phenylamino)-quinazolin-6-yl]-amide: mass spectrum (m/e): M+H 452.

EXAMPLE 26

1-Ethyl-4-prop-2-ynyl-piperazine

Propargyl bromide (20.8 g, 175 mmol) was added dropwise to a mixture of 1-ethyl piperazine (20 g, 175 mmol) and cesium carbonate (57 g, 175 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 19 g of 1-ethyl-4-prop-2-ynyl-piperazine: mass spectrum (m/e): M+H 153.

EXAMPLE 27

4-(4-Ethyl-piperazin-1-yl)-but-2-ynoic acid n-Butyl lithium in hexane (42 mL, 2.5M in n-hexane) was slowly added to 1-ethyl-4-prop-2-ynyl-piperazine (16 g, 105 mmol) in 80 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 18 g of 4-(4-ethyl-piperazin-1-yl)-but-2-ynoic acid: mass spectrum (m/e) :M−H 195.

EXAMPLE 28

4-(4-Ethyl-piperazin-1-yl)-but-2-ynoic acid [4-(3-bromo-phenylamino)-quinazolin-6-yl]-amide Isobutyl chloroformate (0.847 g, 6.2 mmol) and N-methylmorpholine (1.460 g, 14.4 mmol) were added to an ice cold solution of 1.900 g (9.52 mmol) of 4-(4-ethyl-piperazin-1-yl)-but-2-ynoic acid in 50 mL of tetrahydrofuran. After stirring for 30 min, a solution of 1.500 g of N-(3-bromophenyl)-4,6-quinazolindiamine in 10 mL of pyridine was added and the mixture was stirred for 2 hr at 0° C. The reaction was then quenched with ice water, poured into saturated sodium bicarbonate, and the product was extracted with ethyl acetate. Chromatography of the extract on silica gel, eluting with methanol/ethyl acetate (30:70), gave 1.450 g of 4-(4-Ethyl-piperazin-1-yl)-but-2-ynoic acid [4-(3-bromo-phenylamino)-quinazolin-6-yl]-amide: mass spectrum (m/e): M+H 493.

EXAMPLE 29

Bis-(2-methoxy-ethyl)-prop-2-ynyl-amine

Propargyl bromide (17.8 g, 150 mmol) was added dropwise to a mixture of bis(2-methoxy-ethyl)amine (20 g, 150 mmol) and cesium carbonate (49 g, 150 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 20 g of bis-(2-methoxy-ethyl)-prop-2-ynyl-amine: mass spectrum (m/e): M+H 172.

EXAMPLE 30

4-[Bis-(2-methoxy-ethyl)-amino]-but-2-ynoic acid n-Butyl lithium in hexane (42 mL, 2.5M in n-hexane) was slowly added to bis-(2-methoxy-ethyl)-prop-2-ynyl-amine (18 g, 105 mmol) in 80 mL of tetrahydrofuran under nitrogen. The mixture was stirred for 1 h at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 18 g of 4-[bis-(2-methoxy-ethyl)-amino]-but-2-ynoic acid: mass spectrum (m/e):M−H 214.

EXAMPLE 31

4-[3Bis-(2-methoxy-ethyl)-amino]-but-2-ynoic acid [4-(3-bromo-phenylamino)-quinazolin-6-yl]-amide Isobutyl chloroformate (0.845 g, 6.2 mmol) and N-methylmorpholine (0.963 g, 9.52 mmol) were added to an ice cold solution of 2.100 g (9.52 mmol) of 4-[bis-(2-methoxy-ethyl)-amino]-but-2-ynoic acid in 50 mL of tetrahydrofuran under nitrogen. After stirring for 30 min, a solution of 1.500 g of N-(3-bromophenyl)-4,6-quinazolindiamine in 10 mL of pyridine was added and the mixture was stirred for 2 hr at 0° C. The reaction was then quenched with ice water, poured into saturated sodium bicarbonate, and the product was extracted with ethyl acetate. Chromatography of the extract on silica gel, eluting with methanol/ethyl acetate (15:85), gave 0.660 g of 4-[Bis-(2-methoxy-ethyl)-amino]-but-2-ynoic acid [4-(3-bromo-phenylamino)-quinazolin-6-yl]-amide: mass spectrum (m/e): M+H 512.

EXAMPLE 32

1-Methyl-4-prop-2-ynyl-piperazine

Propargyl bromide (23.8 g, 200 mmol) was added dropwise to a mixture of 1-methyl-piperazine (20 g, 200 mmol) and cesium carbonate (65 g, 200 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 7.5 g of 1-methyl-4-prop-2-ynyl-piperazine: mass spectrum (m/e): M+H 139.

EXAMPLE 33

4-(4-Methyl-piperazin-1-yl)-but-2-ynoic acid n-Butyl lithium in hexane (17.2 mL, 2.5M in n-hexane) was slowly added to 1-methyl-4-prop-2-ynyl-piperazine (6.0 g, 43.5 mmol) in 40 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 7 g of 4-(4-methyl-piperazin-1-yl)-but-2-ynoic acid: mass spectrum (m/e):M−H 181.

EXAMPLE 34

4-(4-Methyl-piperazin-1-yl)-but-2-ynoic acid [4-(3-bromo-phenylamino)-quinazolin-6-yl]-amide Isobutyl chloroformate (0.905 g, 6.6 mmol) and N-methylmorpholine (1.550 g, 15.3 mmol) were added to an ice cold solution of 1.900 g (10.71 mmol) of 4-(4-methyl-piperazin-1-yl)-but-2-ynoic acid in 150 mL of tetrahydrofuran under nitrogen. After stirring for 30 min, a solution of 1.500 g of N-(3-bromophenyl)-4,6-quinazolindiamine in 12 mL of pyridine was added and the mixture was stirred for 2 hr at 0° C. The reaction was then quenched with ice water, then it was poured into saturated sodium bicarbonate, and the product was extracted with ethyl acetate. Chromatography of the extract on silica gel, eluting with methanol/ethyl acetate (30:70), gave 0.590 g of 4-(4-methyl-piperazin-1-yl)-but-2-ynoic acid [4-(3-bromo-phenylamino)-quinazolin-6-yl]-amide: mass spectrum (m/e): M+H 479.

EXAMPLE 35

(2-Methoxy-ethyl)-methyl-prop-2-ynyl-amine

Propargyl bromide (26.8 g, 225 mmol) was added dropwise to a mixture of N-(2-methoxyethyl)methyl amine (20 g, 225 mmol) and cesium carbonate (73 g, 225 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 14 g of (2-methoxy-ethyl)-methyl-prop-2-ynyl-amine: mass spectrum (m/e): M+H 127.

EXAMPLE 36

4-[(2-Methoxy-ethyl)-methyl-amino]-but-2-ynoic acid n-Butyl lithium in hexane (37.8 mL, 2.5 M in n-hexane) was slowly added to (2-methoxy-ethyl)-methyl-prop-2-ynyl-amine (12.0 g, 94.5 mmol) in 90 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15 g of 4-[(2-methoxy-ethyl)-methyl-amino]-but-2-ynoic acid: mass spectrum (m/e): M−H 170.

EXAMPLE 37

(2-Methoxy-ethyl)-methyl-amino-but-2-ynoic acid [4-(3-bromo-phenylamino)-quinazolin-6-yl]-amide Isobutyl chloroformate (0.845 g, 6.2 mmol) and N-methylmorpholine (1.2 g, 11.9 mmol) were added to an ice cold solution of 1.6 g (9.52 mmol) of (2-methoxy-ethyl)- methyl-amino-but-2-ynoic acid in 50 mL of tetrahydrofuran under nitrogen. After stirring for 30 min, a solution of 1.500 g of N-(3-bromophenyl)-4,6-quinazolindiamine in 15 mL of pyridine was added and the mixture was stirred for 2 hr at 0° C. The reaction was then quenched with ice water, then it was poured into saturated sodium bicarbonate, and the product was extracted with ethyl acetate. Chromatography of the extract on silica gel, eluting with methanol/ethyl acetate (15:85), gave 0.560 g of (2-methoxy-ethyl)-methyl-amino-but-2-ynoic acid [4-(3-bromo-phenylamino)-quinazolin-6-yl]-amide: mass spectrum (m/e): M+H 468.

EXAMPLE 38

Isopropyl-methyl-prop-2-ynyl-amine

Propargyl bromide (32.5 g, 273 mmol) was added dropwise to a mixture of isopropylmethyl amine (20 g, 273 mmol) and cesium carbonate (89 g, 273 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 6 g of isopropyl-methyl-prop-2-ynyl-amine: mass spectrum (m/e): M+H 111.

EXAMPLE 39

4-(Isopropyl-methyl-amino)-but-2-ynoic acid n-Butyl lithium in hexane (18.4 mL, 2.5 M in n-hexane) was slowly added to isopropyl-methyl-prop-2-ynyl-amine (5.1 g, 46 mmol) in 50 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 5.5 g of 4-(isopropyl-methyl-amino)-but-2-ynoic acid: mass spectrum (m/e): M−H 154.

EXAMPLE 40

Isopropyl-methyl-amino-but-2-ynoic acid [4-(3-bromo-phenylamino)-quinazolin-6-yl]-amide Isobutyl chloroformate (0.845 g, 6.2mmol) and N-methylmorpholine (1.0 g, 9.9 mmol) were added to an ice cold solution of 1.5 g (9.67 mmol) of isopropyl-methyl-amino-but-2-ynoic acid in 70 mL of tetrahydrofuran under nitrogen. After stirring for 30 min, a solution of 1.500 g of N-(3-bromophenyl)-4,6-quinazolindiamine in 15 mL of pyridine was added and the mixture was stirred for 2 hr at 0° C. The reaction was then quenched with ice water, poured into saturated sodium bicarbonate, and the product was extracted with ethyl acetate. Chromatography of the extract on silica gel, eluting with methanol/ethyl acetate (15:85), gave 0.870 g of isopropyl-methyl-amino-but-2-ynoic acid [4-(3-bromo-phenylamino)-quinazolin-6-yl]-amide: mass spectrum (m/e): M+H 452.

EXAMPLE 41

Diisopropyl-prop-2-ynyl -amine

Propargyl bromide (23.5 g, 197 mmol) was added dropwise to a mixture of diisopropyl amine (20 g, 197 mmol) and cesium carbonate (64 g, 197 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 12 g of diisopropyl-prop-2-ynyl-amine: mass spectrum (m/e): M+H 139.

EXAMPLE 42

4-Diisopropylamino-but-2-ynoic acid n-Butyl lithium in hexane (28.8 mL, 2.5 M in n-hexane) was slowly added to diisopropyl-prop-2-ynyl-amine (10.0 g, 72 mmol) in 70 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 11 g of 4-diisopropylamino-but-2-ynoic acid: mass spectrum (m/e): M−H 182.

EXAMPLE 43

Diisopropyl-amino-but-2-ynoic acid [4-(3-bromo-phenylamino)-quinazolin-6-yl]-amide Isobutyl chloroformate (0.845 g, 6.2 mmol) and N-methylmorpholine (1.0 g, 9.9 mmol) were added to an ice cold solution of 1.8 g (9.67 mmol) of diisopropyl-amino-but-2-ynoic acid in 100 mL of tetrahydrofuran under nitrogen. After stirring for 30 min, a solution of 1.500 g of N-(3-bromophenyl)-4,6-quinazolindiamine in 15 mL of pyridine was added and the mixture was stirred for 2 hr at 0° C. The reaction was then quenched with ice water, poured into saturated sodium bicarbonate, and the product was extracted with ethyl acetate. Chromatography of the extract on silica gel, eluting with methanol/ethyl acetate (5:95), gave 1.54 g of diisopropyl-methyl-amino-but-2-ynoic acid [4-(3-bromo-phenylamino)-quinazolin-6-yl]-amide: mass spectrum (m/e): M+H 480.

EXAMPLE 44

Allyl-methyl-prop-2-ynyl-amine

Propargyl bromide (33.4 g, 281 mmol) was added dropwise to a mixture of isopropyl-methyl- amine (20 g, 281 mmol) and cesium carbonate (90 g, 281 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 4.6 g of allyl-methyl-prop-2-ynyl-amine: mass spectrum (m/e): M+H 110.

EXAMPLE 45

4-(Allyl-methyl-amino)-but-2-ynoic acid n-Butyl lithium in hexane (16.4 mL, 2.5 M in n-hexane) was slowly added to allyl-methyl-prop-2-ynyl-amine (4.5 g, 46 mmol) in 50 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 4.1 g of 4-(allyl-methyl-amino)-but-2-ynoic acid: mass spectrum (m/e): M−H 152.

EXAMPLE 46

Allyl-methyl-amino-but-2-ynoic acid [4-(3-bromo-phenylamino)-quinazolin-6-yl]-amide Isobutyl chloroformate (0.845 g, 6.2 mmol) and N-methylmorpholine (1.0 g, 9.9 mmol) were added to an ice cold solution of 1.53 g (10.0 mmol) of allyl-methyl-amino-but-2-ynoic acid in 100 mL of tetrahydrofuran under nitrogen. After stirring for 30 min, a solution of 1.500 g of N-(3-bromophenyl)-4,6-quinazolindiamine in 15 mL of pyridine was added and the mixture was stirred for 2 hr at 0° C. The reaction was then quenched with ice water, then it was poured into saturated sodium bicarbonate, and the product was extracted with ethyl acetate. Chromatography of the extract on silica gel, eluting with methanol/ethyl acetate (5:95), gave 0.750 g of allyl-methyl-amino-but-2-ynoic acid [4-(3-bromo-phenylamino)-quinazolin-6-yl]-amide: mass spectrum (m/e): M+H 450.

EXAMPLE 47

N-[4-[(3-Bromophenyl)amino]-6-quinazolinyl]-3(E)-chloro-2-propenamide

A solution of 2.2 g of N-(3-bromophenyl)-4,6-quinazolindiamine and 1.13 g of diisopropyl methylamine in 25 mL of tetrahydrofuran was cooled in an ice bath as 1.0 g of 3-cis-chloroacryoyl chloride was added over 5 min. After stirring and cooling for 30 min and stirring at room temperature for another 30 min, the mixture was poured into a mixture of brine and saturated sodium bicarbonate. The mixture was extracted with ethyl acetate. The organic layer was dried over magnesium sulfate and the solvent was removed at reduced pressure. The residue was chromatographed on silica gel eluting with chloroform and ethyl acetate mixtures to give N-[4-[(3-bromophenyl)amino]-6-quinazolinyl]-3(E)-chloro-2-propenamide as a yellowish solid. mass spectrum (m/e): M+H 404.7.

EXAMPLE 48

3-[4-(3-Bromo-phenylamino)-quinazolin-6-ylamino]-4-ethoxy-cyclobut-3-ene-1,2-dione A solution of 1.08 g of 3,4-diethoxy-3-cyclobutene-1,2-dione and 1.0 g of N-(3-bromophenyl)-4,6-quinazolindiamine in 10 mL of ethanol was refluxed for 3 hr. The mixture was cooled to room temperature. The solid was collected by filtration and washed with ethanol to give 0.9 g of 3-[4-(3-Bromo-phenylamino)-quinazolin-6-ylamino]-4-ethoxy-cyclobut-3-ene-1,2-dione as a yellow powder: mass spectrum (m/e): M+H 441.1.

EXAMPLE 49

3-[4-(3-Bromo-phenylamino)-quinazolin-6-ylamino]-4-dimethylamino-cyclobut-3-ene-1,2-dione A mixture of 0.8 g of 3-[4-(3-Bromo-phenylamino)-quinazolin-6-ylamino]4-ethoxy-cyclobut-3-ene-1,2-dione, 8 mL of 40% dimethylamine, and 8 mL of ethanol was refluxed for 2 hr. The mixture was cooled to room temperature and the solid was collected and washed with ethanol and ether giving 0.7 g of 3-[4-(3-Bromo-phenylamino)-quinazolin-6-ylamino]-4-dimethylamino-cyclobut-3-ene-1,2-dione as a yellow powder: mass spectrum (m/e): M+H 438.1, 440.1.

EXAMPLE 50

3-[4-(3-Bromo-phenylamino)-quinazolin-6-ylamino]-4-methylamino-cyclobut-3-ene-1,2-dione A mixture of 0.8 g of 3-[4-(3-Bromo-phenylamino)-quinazolin-6-ylamino]-4-ethoxy-cyclobut-3-ene-1,2-dione, 15 mL of 33 % methylamine, 5 mL of water, and 5 mL of ethanol was refluxed for 5 hr. The mixture was cooled to room temperature and the solid was collected and washed with ethanol and ether giving 0.45 g of 3-[4-(3-Bromo-phenylamino)-quinazolin-6-ylamino]-4-methylamino-cyclobut-3-ene-1,2-dione as a yellow powder: mass spectrum (m/e): M+H 426.0.

EXAMPLE 51

3-Amino-4-[4-(3-bromo-phenylamino)-quinazolin-6-ylamino]-cyclobut-3-ene-1,2-dione A mixture of 0.8 g of 3-[4-(3-Bromo-phenylamino)-quinazolin-6-ylamino]-4-ethoxy-cyclobut-3-ene-1,2-dione, 8 mL of ammonium hydroxide, and 8 mL of ethanol was refluxed for 1 hr. The mixture was cooled to room temperature and the solid was collected and washed with ethanol and ether giving 0.65 g of 3-Amino-4-[4-(3-bromo-phenylamino)-quinazolin-6-ylamino]-cyclobut-3-ene-1,2-dione as a yellow powder: mass spectrum (m/e): M+H 412.1.

EXAMPLE 52

3-[4-(3-Bromo-phenylamino)-quinazolin-6-ylamino]-4-morpholin-4-yl-cyclobut-3-ene-1,2-dione A mixture of 0.8 g of 3-[4-(3-Bromo-phenylamino)-quinazolin-6-ylamino]-4-ethoxy-cyclobut-3-ene-1,2-dione, 4 mL of morpholine, and 20 mL of ethanol was refluxed for 2 hr. The mixture was cooled to room temperature and the solid was collected and washed with ethanol and ether giving 0.69 g of 3-[4-(3-Bromo-phenylamino)-quinazolin-6-ylamino]-4-morpholin-4-yl-cyclobut-3-ene-1,2-dione as a yellow powder: mass spectrum (m/e): M+H 480.1, 482.1.

EXAMPLE 53

1-Methyl-1,2,5,6-tetrahydro-pyridine-3-carboxylic acid 4-(3-bromo-phenylamino)-quinazolin-6-yl]-amide A solution of 0.75 g of N-(3-bromophenyl)-4,6-quinazolindiamine and 1.5 g of N,N-diisopropyl methyl amine in 15 mL of tetrahydrofuran was stirred at 0° C. as solid N-methyl-1,2,5,6-tetrahydronicotinyl chloride hydrochloride was added. Stirring was continued for 1 hr at 0° C. and 2 hr. at room temperature. The mixture was poured into a mixture of sodium bicarbonate and brine and extracted with ethyl acetate. The organic solution was dried over magnesium sulfate. The solvent was removed and the residue was chromatographed on silica gel eluting with ethyl acetate and methanol mixtures. The product eluted with ethyl acetate and methanol in a 4:1 ratio containing 1% triethylamine giving 0.9 g of 1-Methyl-1,2,5,6-tetrahydro-pyridine-3-carboxylic acid 4-(3-bromo-phenylamino)-quinazolin-6-yl]-amide as a light yellow powder: mass spectrum (m/e): M+H 438.3, 440.3.

EXAMPLE 54

4-(2-Methoxy-ethoxy)-but-2-ynoic acid

To a suspension of 6 g of 60% sodium hydride in mineral oil in 200 mL of tetrahydrofuran at 0° C. with stirring under nitrogen was added dropwise 10 g of methoxyethanol over 15 min. The mixture was stirred an additional 1 hr. To the stirred mixture at 0° C. was added 19.54 g of propargyl bromide (80% in toluene). Stirring was continued at room temperature over night. The mixture was filtered and the solvent was removed from the filtrate. The residue was distilled. The distillate was dissolved in 250 mL of ether. The solution was stirred under nitrogen and cooled to −78° C. as 40 mL of 2.5 molar n-butyl lithium in hexanes was added over 15 min. Stirring was continued for another 1.5 hr. Dry carbon dioxide was allowed to pass over the surface of the stirring reaction mixture as it warmed from −78° C. to room temperature. The mixture was stirred under a carbon dioxide atmosphere over night. The mixture was poured into a mixture of 100 mL of ammonium chloride and sodium chloride. The organic layer was separated and dried over magnesium sulfate. The solvent was removed and the residue was maintained at 100° C. at 4 mm for 1 hr giving 11.4 g 4-(2-Methoxy-ethoxy)-but-2-ynoic acid.

EXAMPLE 55

4-(2-Methoxy-ethoxy)-but-2-ynoic acid [4-(3-bromo-phenylamino)-quinazolin-6-yl]-amide To a stirred solution of 0.72 g of 4-(2-Methoxy-ethoxy)-but-2-ynoic acid and 0.57 mL of isobutyl chloroformate in 15 mL of tetrahydrofuran at 0° C. was added 0.5 mL of N-methylmorpholine followed by 1.2 g of solid N-(3-bromophenyl)-4,6-quinazolindiamine. Stirring was continued for 1 hr at 0° C. and 30 min at room temperature. The mixture was stored over night at −10° C. The mixture was poured into saturated sodium bicarbonate and extracted with ethyl acetate. The organic solution was dried over magnesium sulfate. The solvent was removed and the residue was chromatographed on silica gel eluting with ethyl acetate, choroform, and methanol solvent mixtures to give 0.55 g of 4-(2-Methoxy-ethoxy)-but-2-ynoic acid [4-(3-bromo-phenylamino)-quinazolin-6-yl]-amide as a yellow solid: mass spectrum (m/e): M+H 454.9, 456.9.

EXAMPLE 56

4-Methoxymethoxy-but-2-ynoic acid

To a suspension of 8.2 g of 60% sodium hydride in mineral oil in 271 mL of tetrahydrofuran at 0° C. with stirring under nitrogen was added dropwise 10 g of propargyl alcohol over 15 min. The mixture was stirred an additional 30 min. To the stirred mixture at 0° C. was added 15.8 g of chloromethylmethyl ether. Stirring was continued at room temperature over night. The mixture was filtered and the solvent was removed from the filtrate. The residue was distilled (35–38° C., 4 mm) giving 8.5 g of a liquid. The distillate was dissolved in 200 mL of ether. The solution was stirred under nitrogen and cooled to −78° C. as 34.1 mL of 2.5 molar n-butyl lithium in hexanes was added over 15 min. Stirring was continued for another 1.5 hr. Dry carbon dioxide was allowed to pass over the surface of the stirring reaction mixture as it warmed from −78° C. to room temperature. The mixture was stirred under a carbon dioxide atmosphere over night. The mixture was poured into a mixture of 14 mL of hydrochloric acid and 24 mL of water. The organic layer was separated and dried over magnesium sulfate. The solvent was removed and the residue was maintained at 100° C. at 4 mm for 1 hr giving 10.4 g 4-Methoxymethoxy-but-2-ynoic acid.

EXAMPLE 57

4-Methoxymethoxy-but-2-ynoic acid [4-(3-bromo-phenylamino)-quinazolin-6-yl]-amide To a stirred solution of 0.66 g of 4-methoxymethoxy-but-2-ynoic acid and 0.60 mL of isobutyl chloroformate in 16 mL of tetrahydrofuran at 0° C. was added 0.5 mL of N-methylmorpholine followed by 1.2 g of solid N-(3-bromophenyl)-4,6-quinazolindiamine. Stirring was continued for 1 hr at 0° C. and 30 min at room temperature. Another equal amount of mixed anhydride as prepared above was added. The mixture was stirred an addition 30 min and stored at −10° C. over night. The mixture was poured into saturated sodium bicarbonate and extracted with ethyl acetate. The organic solution was dried over magnesium sulfate. The solvent was removed and the residue was chromatographed on silica gel eluting with ethyl acetate and choroform solvent mixtures to give 0.35 g of 4-Methoxymethoxy-but-2-ynoic acid [4-(3-bromo-phenylamino)-quinazolin-6-yl]-amide as a tan solid: mass spectrum (m/e): M+H 441.0.

EXAMPLE 58

4-Methoxy-but-2-enoic acid [4-(3-bromo-phenylamino)-quinazolin-6-yl]-amide

A mixture of 54 g of methyl 4-bromocrotonate and 30.2 g of calcium carbonate in 200 mL of methanol was refluxed for 5 days. The mixture was filtered and the solvent was removed from the filtrate. The residue was dissolved in ether and washed with water containing a trace of hydrochloric acid. The ether solution was dried over magnesium sulfate. The solvent was removed and the residue was distilled to give 30.6 g of methyl 4-methoxycrotonate. This material was stirred in 170 mL of 1N sodium hydroxide for 3 min. The solution was washed with ether and the aqueous layer was acidified with sulfuric acid. The mixture was extracted several times with ether. The combined extracts were washed with brine and dried over magnesium sulfate. The solvent was removed to give 4-methoxycrotonic acid as a crystalline solid. A 10 g portion of this acid was stirred in 50 mL of benzene at 0° C. and 8.3 mL of oxalyl chloride was added. The mixture was stirred at room temperature for 6 hr. The solvent was removed and the residue was distilled to give 4-methoxycrotonyl chloride as a colorless liquid.

To a stirred solution of 1.0 g of N-(3-bromophenyl)-4,6-quinazolindiamine and 0.62 g of diisopropyl methylamine in 21 mL of tetrahydrofuran at 0° C. was added 0.62 g of 4-methoxycrotonyl chloride. The mixture was stirred at 0° C. for 1.5 hr and 10 min at room temperature. The mixture was poured into saturated sodium bicarbonate-brine and extracted with ethyl acetate. The organic solution was dried over magnesium sulfate. The solution was filtered through silica gel and the solvent was removed. The residue was recrystallized from 1-butanol to give 1.25 g of 4-Methoxy-but-2-enoic acid [4-(3-bromo-phenylamino)-quinazolin-6-yl]-amide as a yellow solid: mass spectrum (m/e): M+H 415.0.

EXAMPLE 59

2-{[4-(3-Bromo-phenylamino)-quinazolin-6-ylamino]-methyl}-acrylic acid methyl ester A mixture of 3.15 g (0.01 Moles) of N-(3-Bromophenyl)-4,6-quinazolindiamine, 1.32 mL (1.96 g; 0.011 mol) of methyl 2-bromomethyl acrylate, and 2.76 g (0.02 mol) of potassium carbonate in 2 mL of N,N,-dimethylformamide was stirred for 1 ½ hours at room temperature. Then the reaction was poured into water, and the resulting mixture was extracted with two portions of ethyl acetate. The ethyl acetate solution was poured directly onto a chromatography column, and the column eluted with ethyl acetate. Two major products came off the column, the second of which contained the desired product. After evaporation of the solvents, the residue was boiled with methylene chloride. Addition of some hexanes gave a solid which was filtered. The filtrate was evaporated until a solid formed. This gave 0.88 g of the product, which melted at 157–162° C. MS (M+H) 413, 415.

EXAMPLE 60

(E)-4-[4-(3-Bromo-phenylamino)-quinazolin-6-ylamino]-but-2-enoicacid methyl ester A mixture of 3.15 g (0.01 Moles) of N-(3-bromophenyl)-4,6-quinazolindiamine, 1.38 mL (1.96 g; 0.011 moles, 85% pure) of methyl 4-bromocrotonate, and 2.76 g (0.02 moles) of potassium carbonate in 20 mL of N,N,-dimethylformamide was stirred and heated in an oil bath at 80 degrees for 1 hour. The reaction was poured into water, and the resulting mixture was extracted with 3–50 mL portions of ethyl acetate. The combined extracts were washed with 5–50 mL portions of water, then with 25 mL of brine. The ethyl acetate solution was dried over anhydrous magnesium sulfate, then taken to a gum in vacuo. Trituration of this gum with methylene chloride gave 0.875 rams (21%) of CL 151757, melting at 185–190° C. MS M+H=413, 415.

EXAMPLE 61

But-2-ynoic acid [4-(3-dimethylamino-phenylamino)-quinazolin-6-yl]-amide

A mixture of 2.54 grams (0.01 moles) of but-2-ynoic acid [3-cyano-4-(dimethylamino-methyleneamino)-phenyl]-amide, 2.40 grams (0.0115 moles) of N, N-dimethyl-1,3-phenylenediamine dihydrochloride, and 1.59 grams (0.0115 moles) of potassium carbonate in 2.5 mL of glacial acetic acid and 5 mL of acetonitrile was refluxed for an hour. On cooling the solid was filtered and recrystallized from methyl cellusolve to give 2.02 grams (58%) of the desired product, which melted at 252–254° C. MS M+H=346.1.

EXAMPLE 62

2-Morpholin4-ylmethyl-acrylic acid

In a manner described by Krawczyk [Henryk Krawczyk, Synthetic Communications, 25 641–650, (1995)] an 8.8 mL (8.8 g; 0.1 mole) portion of morpholine was added to 6.6 g (0.22 eq) of paraformaldehyde and 10.4 g (0.1 mole) of malonic acid in 100 mL of dioxane. After heating in an oil bath at 70 deg for 1 1/12 hours, the solvents were removed in vacuo. The residue was dissolved in acetone, some insoluble material being filtered. The filtrate was taken to an oil in vacuo. This oil was chromatographed on silica gel. Elution of the product with 1:19 methanol methylene chloride gave 5.51 g (32%) of the product, which melted at 121–125° C.

EXAMPLE 63

N-[4-(3-Bromo-phenylamino)-quinazolin-6-yl]-2-morpholin-4-ylmethyl-acrylamide

A tetrahydrofuran solution of 2.06 g (0.012 moles) of 2-Morpholin-4-ylmethyl-acrylic acid in 25 mL of tetrahydrofuran was cooled in an ice bath, and 1.56 mL (1.64 g; 0.012 mole) of isobutylchloroformate was added, giving a precipitate. This was followed by 1.32 mL (1.22 g; 0.012 mole) of N-methylmorpholine. After 2 minutes, 3.15 g (0.01 mole) of N-(3-bromophenyl)-4,6-quinazolindiamine in 25 mL of pyridine was added. Cooling and stirring were continued for 1 ½ hours. Then the reaction was poured onto ice and 25 mL of ethyl acetate. The resulting mixture was extracted with 3 portions of ethyl acetate. The combined ethyl acetate extracts were washed with brine, dried over sodium sulfate, and taken to an oil in vacuo. This was washed with water and chromatographed on silica gel. The column was eluted with a gradient ranging from 1:1 ethyl acetate hexanes to 1:19 methanol ethyl acetate. The fifth fraction contained 0.733 g (15%) of the desired product Mass Spectrum (m/e) M+H 235.5.

EXAMPLE 64

4-Bromo crotonic acid

After the method of Braun [Giza Braun, J. Am. Chem. Soc. 52, 3167 (1930)], 11.76 mL (17.9 grams 0.1 moles) of methyl 4-bromo crotonate in 32 mL of ethanol and 93 mL of water was cooled to −11° C. The reaction was stirred vigorously, and 15.77 g (0.05 moles) of finely powdered barium hydroxide was added portionwise over a period of about an hour. Cooling and vigorous stirring were continued for about 16 hours. The reaction mixture was then extracted with 100 mL of ether. The aqueous layer was treated with 2.67 mL (4.91 g; 0.05 moles) of concentrated sulfuric acid. The resulting mixture was extracted with 3–100 mL portions of ether. The combined ethereal extracts were washed with 50 mL of brine, then dried over sodium sulfate. The solution was taken to an oil in vacuo. This oil was taken up in about 400 mL of boiling heptane, leaving a gum. The heptane solution was separated and boiled down to about 50 mL. Cooling gave 3.46 g of product.

EXAMPLE 65

4-Bromo-but-2-enoic acid [4-(3-bromo-phenylamino)-quinazolin-6-yl]-amide

A 2.88 mL (4.19 g; 0.033 mole) portion of oxalyl chloride was added to 2.47 g (0.015 moles) of 4-bromo crotonic acid suspended in 25 mL of dichloromethane. To this was added 3 drops of N,N-dimethylformamide. After stirring for about 1 ½ hours, the solvents were removed in vacuo, and the residual oil was dissolved in 20 mL of tetrahydrofuran. This solution was cooled in an ice bath, and a solution of 4.72 g (0.015 moles) of N-(3-bromophenyl)-4,6-quinazolindiamine in 50 mL of tetrahydrofuran was added dropwise. This was followed, still with cooling by the dropwise addition of 2.61 mL (1.99g; 0.015 moles) of diisopropylethylamine in 10 mL of tetrahydrofuran. After cooling and stirring an hour, 80 mL of ethyl acetate and 100 mL of water were added. The layers were separated, and the aqueous layer was extracted with 100 mL of 1:1 tetrahydrofuran ethyl acetate. The combined organic layers were washed with 50 mL of brine, then dried over sodium sulfate. The solution was taken to a solid in vacuo. This solid was digested for an hour with 100 mL of ethyl acetate to give 5.87 g (84%) of product. Mass spectrum (m/e) M+H 460.8, 62.8, 464.8.

EXAMPLE 66

4-Dimethylamino-but-2-enoic acid [4-(3-bromo-phenylamino)-quinazolin-6-yl]-amide Twenty five milliliters of 2N dimethylamine in tetrahydrofuran were stirred and cooled in an ice bath, and a solution of 1.16 g (2.5 mmoles) of 4-Bromo-but-2-enoic acid [4-(3-bromo-phenylamino)-quinazolin-6-yl]-amide in 20 mL of tetrahydrofuran and 10 mL of N,N-dimethylformamide was added dropwise. After stirring for 2 hours, 45 mL of ethyl acetate and 30 mL of saturated aqueous sodium bicarbonate were added, and the layers were separated. The organic layer was extracted with 25 mL of brine, dried over sodium sulfate, and taken to an oil in vacuo. This was chromatographed on silica gel with 1:4 methanol methylene chloride to give 475 mg (44%) of the desired product, which melted at 215–217° C. Mass spectrum (m/e) M+2H 213.4, 214.4. M+H 426.1.

EXAMPLE 67

4-Diethylamino-but-2-enoic acid [4-(3-bromo-phenylamino)-quinazolin-6-yl]-amide

A solution of 5.17 mL (3.65 g; 50 mmoles) of diethylamine in 20 mL of tetrahydrofuran was stirred and cooled in an ice bath, and a solution of 1.16 g (2.5 mmoles) of 4-Bromo-but-2-enoic acid [4-(3-bromo-phenylamino)-quinazolin-6-yl]-amide in 10 mL of tetrahydrofuran and 5 mL of N,N-dimethylformamide was added dropwise. After stirring for 2 hours, 45 mL of ethyl acetate and 30 mL of saturated aqueous sodium bicarbonate were added, and the layers were separated. The organic layer was extracted with 25 mL of brine, dried over sodium sulfate, and taken to an oil in vacuo. This was chromatographed on silica gel with 1:9 methanol methylene chloride to give 677 mg (59%) of the desired product, which melted at 196–199° C. Mass spectrum (m/e) M+2H 228.5.

EXAMPLE 68

Methyldisulfanyl-acetic acid

Mercaptoacetic acid (0.82 mL) was stirred in 50 mL of water and cooled to 0° C. in an ice bath. A solution of 1.33 mL methyl methanethiosulfonate in 20 mL of ethanol was added to the solution dropwise. The mixture was allowed to warm to room temperature and stirred overnight. Saturated aqueous NaCl (20 mL) added to the mixture and 2 portions of 150 mL ether were used to extract the aqueous solution. The combined ether layers were washed with 30 mL of saturated aqueous NaCl solution and dried with magnesium sulfate. Evaporation of the ether gave 2.43 g of a light yellow oil. Kugelrohr distillation gave 1.23 g colorless oil. $^1$HMR (CDCL$_3$): δ10.08(s, 1H); δ3.54 (s, 2H); δ2.5(s, 3H). MS(EI): m/z 137.9 (M$^+$). Adapted a procedure from T. F. Parsons, et al., J. Org. Chem., 30, 1923 (1965).

EXAMPLE 69

N-[4-(3-Bromo-phenylamino)-quinazolin-6-yl]-2-methyldisulfanyl-acetamide

A solution of 1.23 grams of disulfide acid from Example 68 in 30 mL of tetrahydrofuran was cooled in an ice bath. A 1.15 mL portion of isobutyl chloroformate followed by a 0.98 mL portion of N-methyl morpholine was added. After stirring for 5 minutes at 0° C., 0.93 grams of 6-amino 4-(3-bromoanilino)quinazoline was added. The mixture was stirred for 3 hours at 0° C. and then allowed to warm to room temperature. The reaction was quenched with water and the tetrahydrofuran was evaporated under vacuum. Addition of methylene chloride followed by washing the methylene chloride layer with water and evaporation of the solvent gave a crude product. Silica gel chromatography with methanol in methylene chloride gave 0.11 grams of product.

$^1$HNMR (DMSO): δ10.55(s, 1H); δ9.98(s, 1H); δ8.71(d, 1H, J=1.8); δ8.58(s, 1H); δ8.15(t, 1H, J=1.9); δ7.87(m, 3H); δ7.35(m, 2H); δ3.74(s, 2H); δ244(s, 3H).

MS(Electrospray): m/z 435.1, 437.1 (M+H)$^+$

Analysis for C$_{17}$H$_{15}$BrN$_4$OS$_2$ calcd: C:46.90; H:3.47; N: 12.87 found: C:46.79; H3.32; N: 12.47

EXAMPLE 70

3-Methyldisulfanyl-propionic acid 0.9 mL of 3-mercaptopropionic acid was stirred in 50 mL of water and cooled to 0° C. in an ice bath. 20 mL of ethanol solution of 1.11 mL methyl methanethiosulfonate was added to the solution dropwise. The mixture was allowed to warm back to room temperature and stirred overnight. 20 mL of saturated NaCl solution added to the mixture and 2 portions of 150 mL ether was used to extract the aqueous solution. The combined ether layers were washed with 30 mL of saturated aqueous NaCl solution and dried with magnesium sulfate. Evaporation of the ether gave a light yellow oil. Kugelrohr distillation gave 1.5 g of a colorless oil.

$^1$NMR (CDCl$_3$): δ8.85(s, b); δ2.9(t, 2H, J=6); δ2.8(t, 2H, J=6); δ2.45(s, 3H).

EXAMPLE 71

N-[4-(3-Bromo-phenylamino)-quinazolin-6-yl]-3-methyldisulfanyl-propionamide

A solution of 1.5 grams of disulfide acid from Example 70 in 30 mL of tetrahydrofuran was cooled in an ice bath. A 1.28 mL portion of isobutyl chloroformate followed by a 1.08 mL portion of N-methyl morpholine were added. After stirring for 5 minutes at 0° C., 0.77 grams of 6-amino 4-(3-bromoanilino)quinazoline was added. The mixture was stirred for 3 hours at 0° C. and then allowed to warm to room temperature. The reaction was quenched with water and the tetrahydrofuran was evaporated under vacuum. Addition of methylene chloride followed by washing the methylene chloride layer with water and evaporation of the solvent gave a crude product. Silica gel chromatography with methanol in methylene chloride gave 0.22 grams light yellow solid of product.

$^1$HNMR (DMSO): δ10.42(s, 1H); δ9.94(s, 1H); δ8.73(d, 1H, J=1.5); δ8.58(s, 1H); δ8.18 (t, 1H, J=1.8); δ7.85(m, 3H); δ7.33(m, 2H); δ3.06(t, 2H, J=7.2); d2.85(t, 2H, J=6.6); δ2.46(s, 3H).

MS(Electrospray): m/z 449.1, 451.1 (M+H)$^+$

Analysis for C$_{18}$H$_{17}$BrN$_4$OS$_2$ calcd: C:48.11; H:3.11: N: 12.47 found: C:47.91; H:3.85; N: 11.58

EXAMPLE 72

2-Methyldisulfanyl-propionic acid

2-Mercaptopropionic acid (1.25 mL) was stirred in 50 mL of water and cooled to 0° C. in an ice bath. A solution of 1.57 mL methyl methanethiosulfonate in 20 mL of ethanol was added to the solution dropwise. The mixture was allowed to warm to room temperature and stirred overnight. Saturated aqueous NaCl (20 mL) was added to the mixture and 2 portions of 150 mL ether were used to extract the aqueous solution. The ether extraction was back washed with 30 mL of saturated NaCl solution and dried with magnesium sulfate. Evaporation of ether to give 2 g colorless oil.

$^1$HNMR (CDCl$_3$): δ3.55(q,1H,J=7.1 Hz); 2.46(s,3H); d1.51(d, 3H,J=7.1Hz).

MS(Electrospray): n/z 151 (M–H)$^-$.

EXAMPLE 73

N-[4-(3-Bromo-phenylamino)-quinazolin-6-yl]-2-methyldisulfanyl-propionamide

A solution of 2 grams of disulfide acid from Example 72 in 50 mL of tetrahydrofuran was cooled in an ice bath. A 1.7 mL portion of isobutyl chloroformate followed by a 1.4 mL portion of N-methyl morpholine were added. After stirring for 5 minutes at 0° C., 1.0 grams of 6-amino 4-(3-bromoanilino)quinazoline was added. The mixture was stirred for 3 hours at 0° C. and then allowed to warm to room temperature. The reaction was quenched with water and the tetrahydrofuran was evaporated under vacuum. Addition of methylene chloride followed by washing the methylene chloride layer with water and evaporation of the solvent gave a crude product. Silica gel chromatography with methanol in methylene chloride gave 0.7 grams white solid of product.

$^1$HNMR (DMSO): δ10.54(s, 1H); δ9.98(s, 1H); δ8.74(d, 1H, J=1.8); δ8.58(s, 1H); δ8.15(s, 1H); δ7.87(m, 3H); δ7.33 (m, 2H); δ3.90(q, 1H, J=7.0); δ2.43 (s, 3H); δ1.50(d, 3H, J=6.9).

MS(Electrospray): m/z 449.1, 451.1 (M+H)$^+$

Analysis for C$_{18}$H$_{17}$BrN$_4$OS$_2$ calcd: C:48.11; H:3.81: N: 12.47 found: C:47.74; H3.67; N: 12.32

EXAMPLE 74 tert-Butyldisulfanyl-acetic acid

To 11 g (50 mmol) of 2-,2'-dipyridyl disulfide and 8.4 mL (60 mmol) of triethyl amine in 100 mL of tetrahydrofuran at 0° C. as added 2.8 mL (40 mmol) of mercaptoacetic acid in 5 mL of tetrahydrofuran. The ice bath was removed and after one hour 6.8 mL (65 mmol) tert-butyl thiol was added. The reaction was allowed to stir overnight at ambient temperature before diluting with ether and washing three times with 1N aqueous HCl. The product was then extracted into 10% aqueous NaOH. The aqueous phase was washed twice with ether and then acidified with HCl to pH ~3.5. The product was extracted with ether, dried with Na2SO4, filtered and evaporated under reduced pressure to give a crude product. This material was distilled by Kugelrohr distillation to give 6.6 g (37 mmol, 92%) of partially purified product. This material was used in the next step without further purification.

EXAMPLE 75

N-[4-(3-Bromo-phenylamino)-quinazolin-6-yl]-2-tert-butyldisulfanyl-acetamide

A solution of 2.7 grams of disulfide acid from Example 74 in 25 mL of tetrahydrofuran was cooled in an ice bath. A 1.9 mL portion of isobutylchloroformate followed by a 1.6 mL portion of N-methyl morpholine were added. After stirring for 5 minutes at 0° C., 1.0 grams of N-(3-bromophenyl)4,6-quinazolindiamine was added. The mixture was stirred for 3 hours at 0° C. and then allowed to warm to room temperature. The reaction was quenched with water and the tetrahydrofuran was evaporated under vacuum. Addition of methylene chloride followed by washing the methylene chloride layer with water and evaporation of the solvent gave a crude product. Silica gel chromatography with methanol in methylene chloride gave 0.3 grams white solid of product.

$^1$HNMR (DMSO): δ10.50(s, 1H); δ9.97(s, 1H); δ8.71(d, 1H, J=1.8); δ8.58(s, 1H); δ8.16(s, 1H); δ7.84(m, 3H); δ7.34 (m, 2H); δ3.75(s, 2H); δ1.34(d, 9).

MS(Electrospray): m/z 477.1, 479.1 (M+H)$^+$

Analysis for C$_{20}$H$_{21}$BrN$_4$OS$_2$ calcd: C:50.31; H:4.43: N: 11.73 found: C:49.73; H:4.16; N: 11.62

EXAMPLE 76 iso-Butyldisulfanyl-acetic acid

To 11 g (50 mmol) of 2-,2'-dipyridyl disulfide and 10.5 mL (75 mmol) of triethyl amine in 100 mL of tetrahydrofuran at 0° C. as added 3.5 mL (50 mmol) of mercaptoacetic acid in 5 mL of tetrahydrofuran. The ice bath was removed and after one hour 5.5 mL (50 mmol) iso-butyl thiol was added. The reaction was allowed to stir overnight at ambient temperature before diluting with ether and washing three times with 1N aqueous HCl. The product was then extracted into 10% aqueous NaOH. The aqueous phase was washed twice with ether and then acidified with HCl to pH ~3.5. The product was extracted with ether, dried with Na2SO4, filtered and evaporated under reduced pressure to give a crude product. This material was distilled by Kugelrohr distillation to give 3.0 g (17 mmol, 33%) of partially purified product. This material was used in the next step without further purification.

EXAMPLE 77

N-[4-(3-Bromo-phenylamino)-quinazolin-6-yl]-2-isobutyldisulfanyl-acetamide

A solution of 3.0 grams of disulfide acid from Example 76 in 50 mL of tetrahydrofuran was cooled in an ice bath. A 2.1 mL portion of isobutyl chloroformate followed by a 1.8 mL portion of N-methyl morpholine were added. After stirring for 5 minutes at 0° C., 0.85 grams of 6-amino 4-(3-bromoanilino)quinazoline was added. The mixture was stirred for 3 hours at 0° C. and then allowed to warm to room temperature. The reaction was quenched with water and the tetrahydrofuran was evaporated under vacuum. Addition of methylene chloride followed by washing the methylene chloride layer with water and evaporation of the solvent gave a crude product. Silica gel chromatography with methanol in methylene chloride gave 0.15 grams white solid of product.

$^1$HNMR (DMSO): δ11.0(s, 1H); δ9.98(s, 1H); δ8.71(s, 1H,); δ8.58(s, 1H); δ8.15(m, 1H); δ7.84(m, 3H); δ7.32(m, 2H); δ3.72(s, 2H); δ2.70(d, 2H, J=6.9); δ1.92(m, 1H); δ0.92(d, 6H, J=6.6).

MS(Electrospray): m/z 477.2, 479.2 (M+H)$^+$

Analysis for C$_{20}$H$_{21}$BrN$_4$OS$_2$ calcd: C:50.31; H:4.43: N: 11.73 found: C:50.13; H:4.34; N: 11.56

EXAMPLE 78 iso-Propyldisulfanyl-acetic acid

To 11 g (50 mmol) of 2-,2'-dipyridyl disulfide and 8.4 mL (60 mmol) of triethyl amine in 100 mL of tetrahydrofuran at 0° C. as added 2.8 mL (40 mmol) of mercaptoacetic acid in 5 mL of tetrahydrofuran. The ice bath was removed and after one hour 6.0 mL (65 mmol) isopropyl thiol was added. The reaction was allowed to stir overnight at ambient temperature before diluting with ether and washing three times with 1N aqueous HCl. The product was then extracted into 10% aqueous NaOH. The aqueous phase was washed twice with ether and then acidified with HCl to pH ~3.5. The product was extracted with ether, dried with Na2SO4, filtered and evaporated under reduced pressure to give a crude product. This material was distilled by Kugelrohr distillation to give 3.5 g (21 mmol, 42%) of partially purified product. This material was used in the next step without further purification.

EXAMPLE 79

N-[4-(3-Bromo-phenylamino)-quinazolin-6-yl]-2-isopropyldisulfanyl-acetamide

A solution of 1.4 grams of disulfide acid from Example 78 in 30 mL of tetrahydrofuran was cooled in an ice bath. A 1.1 mL portion of isobutyl chloroformate followed by a 0.9 mL portion of N-methylmorpholine were added. After stirring for 5 minutes at 0° C., 0.66 grams of N-(3-bromophenyl)-4,6-quinazolindiamine was added. The mixture was stirred for 3 hours at 0° C. and then allowed to warm to room temperature. The reaction was quenched with water and the tetrahydrofuran was evaporated under vacuum. Addition of methylene chloride followed by washing the methylene chloride layer with water and evaporation of the solvent gave a crude product. Silica gel chromatography with methanol in methylene chloride gave 0.01 grams of product.

$^1$HNMR (DMSO): δ10.65(s, 1H); δ10.01(s, 1H); δ8.74(s, 1H,); δ8.59(bs, 1H); δ8.18(m, 1H); δ7.95(m, 1H); δ7.85(m, 2H) δ7.35(m, 2H); δ3.73(s, 2H); δ3.15(m, 1H); δ1.27(d, 6H, J=6.6).

MS(Electrospray): m/z 463.1, 465.1 (M+H)$^+$

HRMS(EI): Calcd462.0184, Found462.0140

EXAMPLE 80

2,3-epoxy-proponic acid

To a suspension of 2.0 g of glycidol and 20.0 g of sodium periodate in 27 mL of acetonitrile and 40.5 mL of water was added RuCl3.(H2O)3 at room temperature. The resulting reaction mixture was stirred vigorously for 2hr., and then was diluted with 270 mL of ether. The organic phase was separated. The aqueous phase was extracted with ether (3×100 mL). The combined organic solvents were dried over Na2SO4 and filtered through a celite pad. Removal of the solvent gave the crude product. Purification of the crude product on flash chromatography yielded 1.12 g of the epoxy acid as liquid in 47% yield.
Reference: Dominique Pons, Moique Savignac and Jean-Pierre Genet, Tetrahedron
Letters,
31(35), P.5023–5026, 1990.

EXAMPLE 81

Oxirane-2-carboxylic acid [4-(3-bromo-phenylamino)-quinazolin-6-yl]-amide

A solution of 280 mg of 2,3-epoxy propoinic acid in 2.0 mL of tetrahydrofuran was cooled in an ice bath. A 0.42 mL portion of isobutyl chloroformate followed by a 0.48 mL portion of N-methylmorpholine were added. After 5 minutes, a suspension of 500 mg of N-(3-bromophenyl)-4,6-quinazolindiamine in 4 mL of tetrahydrofuran was added. The resulting reaction mixture was stirred at 0° C. for 3 hr., and then was diluted with 30 mL of water. The aqueous solution was extrated with 50 mL of ethyl acetate. The organic phase was separated, dried over Na2SO4 and filtered. The solvent was removed at reduced pressure to give a solid residue. Purification of the crude produt on preparative TLC afforded 109.9 mg of the product as yellow solid in 18 % yield; mp 228–300° C.; mass(m/e) 385.0264.

EXAMPLE 82

Ethenesulfonic acid [4-(3-bromo-phenylamino)-quinazolin-6-yl]-amide

To a solution of N-(3-bromophenyl)-4,6-quinazolindiamine (315 mg, 1 mmol) and triethylamine (0.5 mL) in THF (50 mL) at 0° C. was dropwise added 2-chloroethylsulfonyl chloride (490 mg, 3 mmol). After the solution was stirred at 0° C. for 10 min, it was chromatographed on silica gel with 10% methanol in chloroform to give 212 mg of ethenesulfonic acid [4-(3-bromo-phenylamino)-quinazolin-6-yl]-amide as an light yellow solid: HRMS (m/e): M+403.9937. Modified a method from A. A. Goldberg, J. Chem., Soc., 464 (1945).

What is claimed is:

1. A compound of formula 1 having the structure

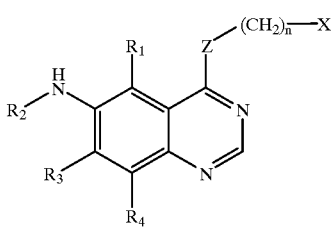

wherein:
X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

$R_1$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_7$—$(C(R_6)_2)_g$—Y—, $R_7$—$(C(R_6)_2)_p$—M—$(C(R_6)_2)_k$—Y—, or Het-W—$(C(R_6)_2)_k$—Y—

Y is a divalent radical selected from the group consisting of

—$(CH_2)_a$— , —O— , and —$\underset{R_6}{N}$— ;

$R_7$ is —$NR_6R_6$, or —$OR_6$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is a heterocycle, optionally mono- or di-substituted on carbon or nitrogen with $R_6$ and optionally mono-substituted on carbon with —$CH_2OR_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;

$R_2$, is selected from the group consisting of

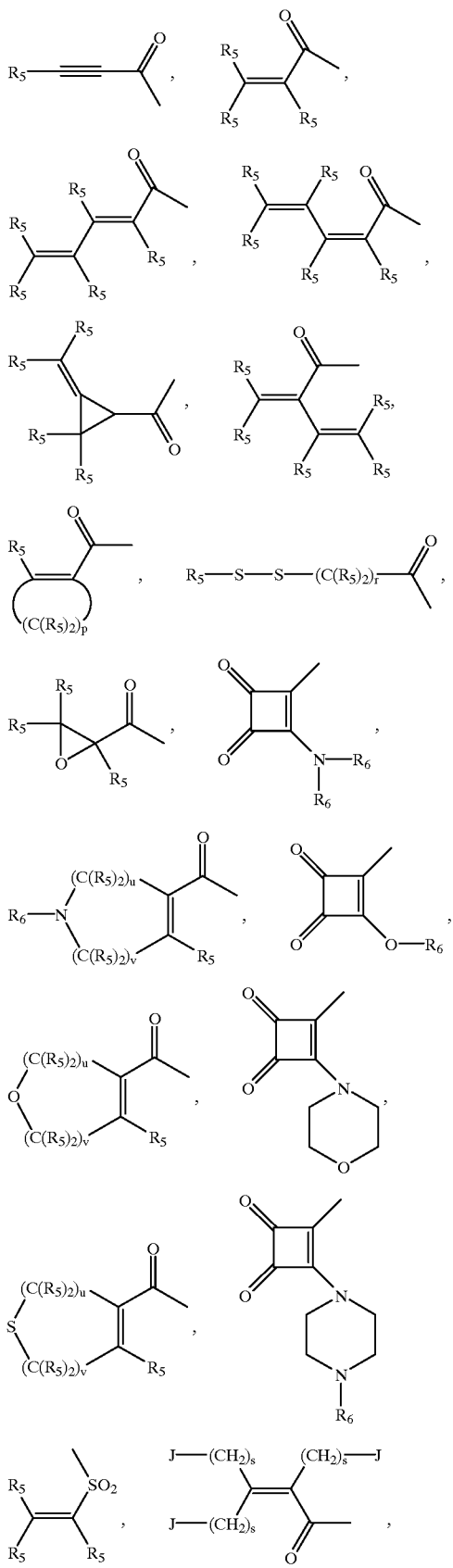

$R_5$ is independently hydrogen, alkyl of 1–6 carbon atoms, carboxy, carboalkoxy of 1–6 carbon atoms, phenyl, carboalkyl of 2–7 carbon atoms, $R_7$—(C(R_6)_2)_s—, $R_7$—(C(R_6)_2)_p—M—(C(R_6)_2)_r—, $R_8R_9$—CH—M—(C(R_6)_2)_r—, or Het-W—(C(R_6)_2)_r—;

$R_8$, and $R_9$ are each, independently, —(C(R_6)_2)_rNR_6R_6, or —(C(R_6)_2)_rOR_6;

J is independently hydrogen, chlorine, fluorine, or bromine;

Q is alkyl of 1–6 carbon atoms or hydrogen;

a=0 or 1;
g=1–6;
k=0–4;
n is 0–1;
p=2–4;
q=0–4;
r=1–4;
s=1–6;
u=0–4 and v=0–4, wherein the sum of u+v is 2–4;
or a pharmaceutically acceptable salt thereof,
provided that when:
  Z is NH;
  n is 0;
  $R_2$ is selected from the group consisting of $R_5$ is independently and exclusively hydrogen, alkyl of 1–6 carbon atoms, carboxy, carboalkoxy of 1–6 carbon atoms, phenyl, or carboalkyl of 2–7 carbon atoms;

$R_1$ is hydrogen, halogen, alkyl of 1–6 carbon atoms, or alkoxy of 1–6 carbon atoms;

$R_4$ is hydrogen, halogen, alkyl of 1–6 carbon atoms, or alkoxy of 1–6 carbon atoms; and $R_3$ is hydrogen, alkyl of 1–6 carbon atoms, alkoxy of 1–6 carbon atoms, hydroxy, or trifluoromethyl;

X is not an unsubstituted phenyl ring, or a phenyl ring exclusively substituted with one or more substitutents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

further provided that when $R_2$ is and $R_5$ is hydrogen or alkyl of 1–6 carbon atoms, $R_3$ is not halogen;

and still further provided that
  when $R_6$ is alkenyl of 2–7 carbon atoms or alkynyl of 2–7 carbon atoms, such alkenyl or alkynyl moiety is bound to a nitrogen or oxygen atom through a saturated carbon atom;

and finally provided that
  when Y is —NR_6— or $R_7$ is —NR_6R_6 then g=2–6;
  when M is —O— and $R_7$ is —OR_6 then p=1–4;
  when Y is —NR_6— then k=2–4;
  when Y is —O— and M or W is —O— then k=1–4
  and when W is a bond with Het bonded through a nitrogen atom and Y is —O— or —NR_6— then k=2–4.

2. The compound according to claim 1 wherein n=0, Z is —NH—, and X a phenyl ring unsubstituted or substituted with halogen or alkyl of 1–6 carbon atoms or a pharmaceutically acceptable salt thereof.

3. The compound according to claim 2 wherein $R_1$, $R_3$, and $R_4$ are hydrogen.

4. A compound according to claim 1 which is 4-dimethylamino-but-2-enoic acid [4-(3-bromo-phenylamino)-quinazolin-6-yl]-amide or a pharmaceutically acceptable salt thereof.

5. A compound of claim 1 which is 4-morpholin-4-yl-but-2-ynoic acid [4-(3-bromo-phenylamino)-quinazolin-6-yl]-amide, 4-dimethylamino-but-2-ynoic acid [4-(3-bromo-phenylamino)-quinazolin-6-yl]-amide, 4-diethylamino-but-2-ynoic acid [4-(3-bromo-phenylamino)-quinazolin-6-yl]-amide, 4-(4-ethyl-piperazin-1-yl)-but-2-ynoic acid [4-(3-bromo-phenylamino)-quinazolin-6-yl]-amide, 4-(4-methyl-piperazin-1-yl)-but-2-ynoic acid [4-(3-bromo-phenylamino)-quinazolin-6-yl]-amide, 4-[bis-(2-methoxy-ethyl)-amino]-but-2-ynoic acid [4-(3-bromo-phenylamino)-quinazolin-6-yl]-amide, (2-methoxy-ethyl)-methyl-amino-but-2-ynoic acid [4-(3-bromo-phenylamino)-quinazolin-6-yl]-amide, isopropyl-methyl-amino-but-2-ynoic acid [4-(3-bromo-phenylamino)-quinazolin-6-yl]-amide, diisopropyl-amino-but-2-ynoic acid [4-(3-bromo-phenylamino)-quinazolin-6-yl]-amide, allyl-methyl-amino-but-2-ynoic acid [4-(3-bromo-phenylamino)-quinazolin-6-yl]-amide, or but-2-ynoic acid [4-(3-dimethylamino-phenylamino)-quinazolin-6-yl]-amide or a pharmaceutically accetable salt thereof.

6. A compound of claim 1 which is 4-methoxy-but-2-ynoic acid [4-(3-bromo-phenylamino)-quinazolin-6-yl]-amide, 4-(2-methoxy-ethoxy)-but-2-ynoic acid [4-(3-bromo-phenylamino)-quinazolin-6-yl]-amide, or 4-methoxymethoxy-but-2-ynoic acid [4-(3-bromo-phenylamino)-quinazolin-6-yl]-amide or a pharmaceutically accetable salt thereof.

7. A compound of claim 1 which is 3-[4-(3-bromo-phenylamino)-quinazolin-6-ylamino]-4-ethoxy-cyclobut-3-ene-1,2-dione, 3-[4-(3-bromo-phenylamino)-quinazolin-6-ylamino]-4-dimethylamino-cyclobut-3-ene-1,2-dione, 3-[4-(3-bromo-phenylamino)-quinazolin-6-ylamino]-4-methylamino-cyclobut-3-ene-1,2-dione, 3-amino-4-[4-(3-bromo-phenylamino)-quinazolin-6-ylamino]-cyclobut-3-ene-1,2-dione, or 3-[4-(3-bromo-phenylamino)-quinazolin-6-ylamino]-4-morpholin-4-yl-cyclobut-3-ene-1,2-dione or a pharmaceutically accetable salt thereof.

8. A compound of claim 1 which is 4-methoxy-but-2-enoic acid [4-(3-bromo-phenylamino)-quinazolin-6-yl]-amide, or 1-methyl-1,2,5,6-tetrahydro-pyridine-3-carboxylic acid 4-(3-bromo-phenylamino)-quinazolin-6-yl]-amide or a pharmaceutically acceptable salt thereof.

9. A compound of claim 1 which is N-[4-(3-bromo-phenylamino)-quinazolin-6-yl]-2-morpholin-4-ylmethyl-acrylamide, or 4-diethylamino-but-2-enoic acid [4-(3-bromo-phenylamino)-quinazolin-6-yl]-amide, or a pharmaceutically accetable salt thereof.

10. A compound of claim 1 which is N-[4-(3-bromo-phenylamino)-quinazolin-6-yl]-2-methyldisulfanyl-propionamide, N-[4-(3-bromo-phenylamino)-quinazolin-6-yl]-3-methyldisulfanyl-propionamide, N-[4-(3-bromo-phenylamino)-quinazolin-6-yl]-2-methyldisulfanyl-acetamide, N-[4-(3-bromo-phenylamino)-quinazolin-6-yl]-2-tert-butyldisulfanyl-acetamide, N-[4-(3-bromo-phenylamino)-quinazolin-6-yl]-2-isobutyldisulfanyl-acetamide, or N-[4-(3-bromo-phenylamino)-quinazolin-6-yl]-2-isopropyldisulfanyl-acetamide or a pharmaceutically accetable salt thereof.

11. A compound which is 2-{[4-(3-bromo-phenylamino)-quinazolin-6-ylamino]-methyl}-acrylic acid methyl ester, or (E)-4-[4-(3-bromo-phenylamino)-quinazolin-6-ylamino]-methyl}-but-2-enoicacid methyl ester or a pharmaceutically acceptable salt thereof.

12. A compound which is 4-chloro-but-2-ynoic acid [4-(3-bromo-phenylamino)-quinazolin-6-yl]-amide, 4-hydroxy-but-2-ynoic acid [4-(3-bromo-phenylamino)-quinazolin-6-yl]-amide, N-[4-[(3-bromophenyl)amino]-6-quinazolinyl]-3(E)-chloro-2-propenamide, 4-bromo-but-2-enoic acid [4-(3-bromo-phenylamino)-quinazolin-6-yl]-amide, oxirane-2-carboxylic acid [4-(3-bromo-phenylamino)-quinazolin-6-yl]-amide, or ethenesulfonic acid[4-(3-bromo-phenylamino)-quinazolin-6-yl]-amide or a pharmaceutically acceptable salt thereof.

13. A method of inhibiting the biological effects of a deregulated protein tyrosine kinase in a mammal in need thereof which comprises administering to said mammal an effective amount of a compound of formula 1 having the structure

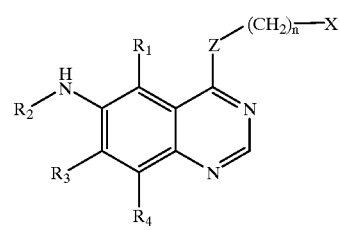

1 wherein:
X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

$R_1$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_7-(C(R_6)_2)_g-Y-$, $R_7-(C(R_6)_2)_p-M-(C(R_6)_2)_k-Y-$, or Het-W-$(C(R_6)_2)_k-Y-$ Y is a divalent radical selected from the group consisting of $-(CH_2)_a-$, $-O-$, and $-\underset{R_6}{N}-$ ;

$R_7$ is $-NR_6R_6$, or $-OR_6$;
M is $>NR_6$, $-O-$, $>N-(C(R_6)_2)_pNR_6R_6$, or $>N-(C(R_6)_2)_p-OR_6$;
W is $>NR_6$, $-O-$ or is a bond;
Het is a heterocycle, optionally mono- or di-substituted on carbon or nitrogen with $R_6$ and optionally mono-substituted on carbon with $-CH_2OR_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;
$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;
$R_2$, is selected from the group consisting of

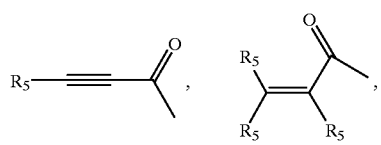

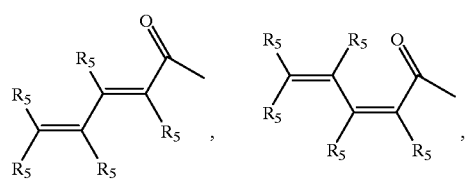

-continued

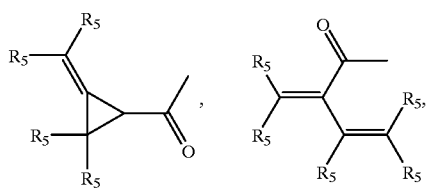

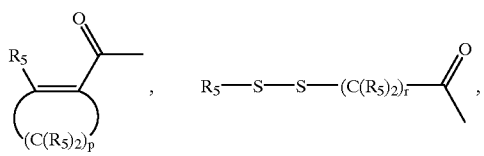

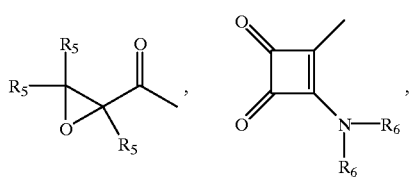

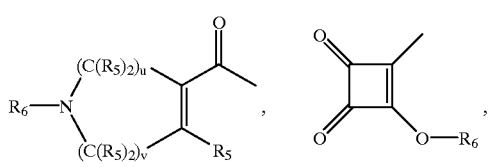

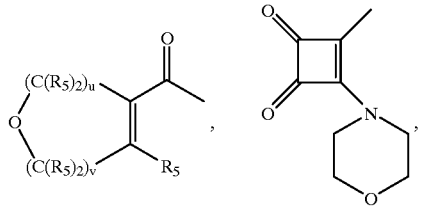

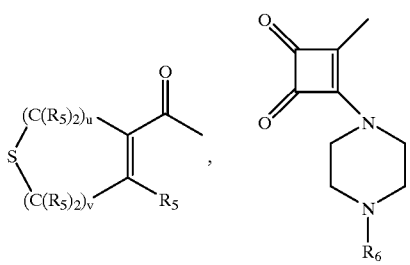

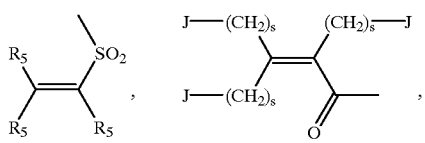

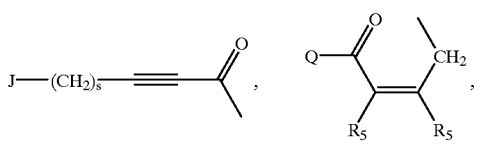

-continued

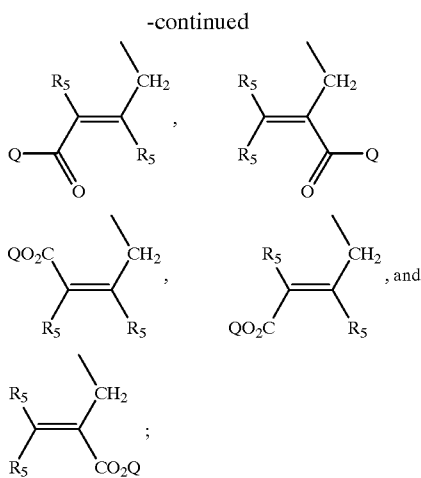

$R_5$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0 or 1;

g=1–6;

k=0–4;

n is 0–1;

p=2–4;

q=0–4;

r=1–4;

s=1–6;

u=0–4 and v=0–4, wherein the sum of u+v is 2–4;

or a pharmaceutically acceptable salt thereof, provided that when:
  Z is NH;
  n is 0;
  $R_2$ is selected from the group consisting of

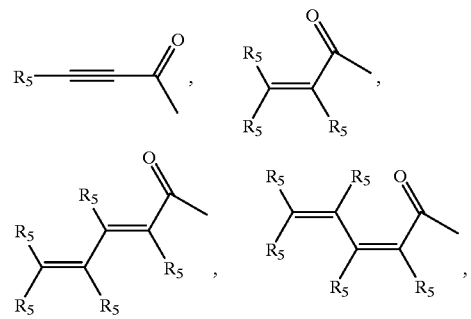

-continued

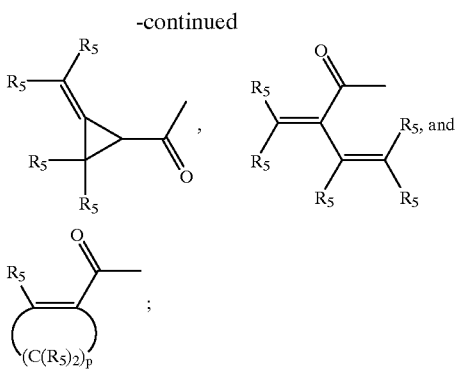

$R_5$ is independently and exclusively hydrogen, alkyl of 1–6 carbon atoms, carboxy, carboalkoxy of 1–6 carbon atoms, phenyl, or carboalkyl of 2–7 carbon atoms;

$R_1$ is hydrogen, halogen, alkyl of 1–6 carbon atoms, or alkoxy of 1–6 carbon atoms;

$R_4$ is hydrogen, halogen, alkyl of 1–6 carbon atoms, or alkoxy of 1–6 carbon atoms; and $R_3$ is hydrogen, alkyl of 1–6 carbon atoms, alkoxy of 1–6 carbon atoms, hydroxy, or trifluoromethyl;

X is not an unsubstituted phenyl ring, or a phenyl ring exclusively substituted with one or more substitutents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

further provided that when $R_2$ is

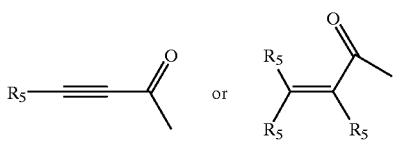

and $R_5$ is hydrogen or alkyl of 1–6 carbon atoms,
$R_3$ is not halogen;

and still further provided that
  when $R_6$ is alkenyl of 2–7 carbon atoms or alkynyl of 2–7 carbon atoms, such alkenyl or alkynyl moiety is bound to a nitrogen or oxygen atom through a saturated carbon atom;

and finally provided that
  when Y is —NR$_6$— or $R_7$ is —NR$_6$R$_6$ then g=2–6;
  when M is —O— and $R_7$ is —OR$_6$ then p=1–4;
  when Y is —NR$_6$— then k=2–4;
  when Y is —O— and M or W is —O— then k=1–4
  and when W is a bond with Het bonded through a nitrogen atom and Y is —O— or —NR$_6$— then k=2–4.

14. A method of treating, inhibiting the growth of, or eradicating neoplasms in a mammal in need thereof which comprises administering to said mammal an effective amount of a compound of formula 1 having the structure

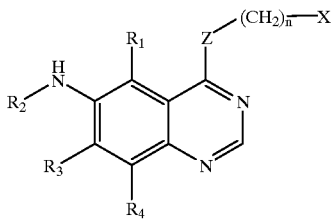

wherein:
- X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;
- Z is —NH—, —O—, —S—, or —NR—;
- R is alkyl of 1–6 carbon atoms, or carboalkyl of 2–7 carbon atoms;
- $R_1$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_7$—$(C(R_6)_2)_g$—Y—, $R_7$—$(C(R_6)_2)_p$—M—$(C(R_6)_2)_k$—Y—, or Het-W—$(C(R_6)_2)_k$—Y—

Y is a divalent radical selected from the group consisting of

—$(CH_2)_a$—, —O—, and —N($R_6$)—;

$R_7$ is —$NR_6R_6$, or —$OR_6$;

M is >$NR_6$, —O—, >N—$(C(R_6)_2)_p$$NR_6R_6$, or >N—$(C(R_6)_2)_p$—$OR_6$;

W is >$NR_6$, —O— or is a bond;

Het is a heterocycle, optionally mono- or di-substituted on carbon or nitrogen with $R_6$ and optionally mono-substituted on carbon with —$CH_2OR_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;

$R_2$, is selected from the group consisting of

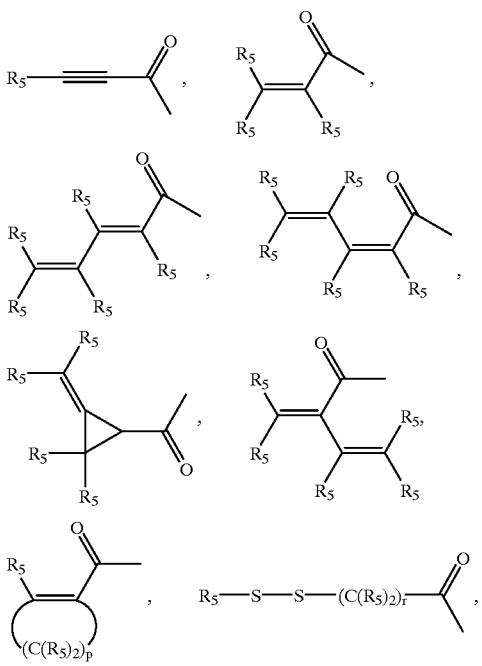

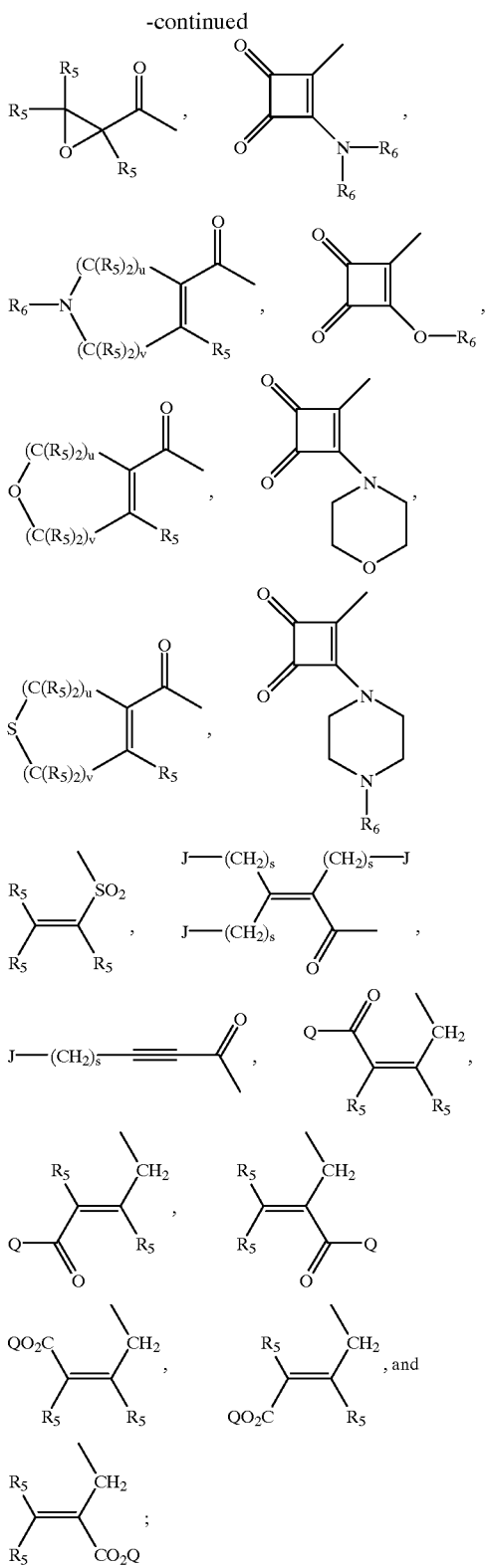

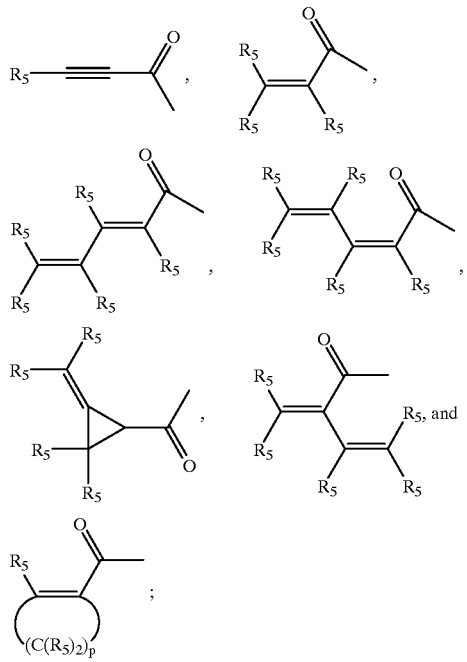

$R_5$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0 or 1;

g=1–6;

k=0–4;

n is 0–1;

p=2–4;

q=0–4;

r=1–4;

s=1–6;

u=0–4 and v=0–4, wherein the sum of u+v is 2–4;

or a pharmaceutically acceptable salt thereof, provided that when:

Z is NH;

n is 0;

$R_2$ is selected from the group consisting of $R_5$ is independently and exclusively hydrogen, alkyl of 1–6 carbon atoms, carboxy, carboalkoxy of 1–6 carbon atoms, phenyl, or carboalkyl of 2–7 carbon atoms;

$R_1$ is hydrogen, halogen, alkyl of 1–6 carbon atoms, or alkoxy of 1–6 carbon atoms;

$R_4$ is hydrogen, halogen, alkyl of 1–6 carbon atoms, or alkoxy of 1–6 carbon atoms; and $R_3$ is hydrogen, alkyl of 1–6 carbon atoms, alkoxy of 1–6 carbon atoms, hydroxy, or trifluoromethyl;

X is not an unsubstituted phenyl ring, or a phenyl ring exclusively substituted with one or more substitutents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

further provided that when $R_2$ is $$R_5-\!\!\!\equiv\!\!\!-\!\!\!\overset{O}{\underset{}{\text{C}}}\!\!\!-\quad\text{or}\quad \underset{R_5\quad R_5}{\overset{R_5}{\text{C}=\text{C}}}\!\!\!-\overset{O}{\underset{}{\text{C}}}\!\!\!-$$

and $R_5$ is hydrogen or alkyl of 1–6 carbon atoms, $R_3$ is not halogen;

and still further provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and finally provided that when Y is —$NR_6$— or $R_7$ is —$NR_6R_6$ then g=2–6;
when M is —O— and $R_7$ is —$OR_6$ then p=1–4;
when Y is —$NR_6$— then k=2–4;
when Y is —O— and M or W is —O— then k=1–4
and when W is a bond with Het bonded through a nitrogen atom and Y is —O— or —$NR_6$— then k=2–4.

15. The method according to claim 14 wherein the neoplasm expresses EGFR or erbB2 (Her2).

16. The method according to claim 14 wherein the neoplasm is selected from the group consisting of breast, kidney, bladder, mouth, larynx, esophagus, stomach, colon, ovary, and lung.

17. A method of treating, inhibiting the progression of, or eradicating polycystic kidney disease in a mammal in need thereof which comprises administering to said mammal an effective amount of a compound of formula 1 having the structure $$\text{1}$$

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

$R_1$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_7$—$(C(R_6)_2)_g$—Y—, $R_7$—$(C(R_6)_2)_p$—M—$(C(R_6)_2)_k$—Y—, or Het-W—$(C(R_6)_2)_k$—Y—

Y is a divalent radical selected from the group consisting of

-continued

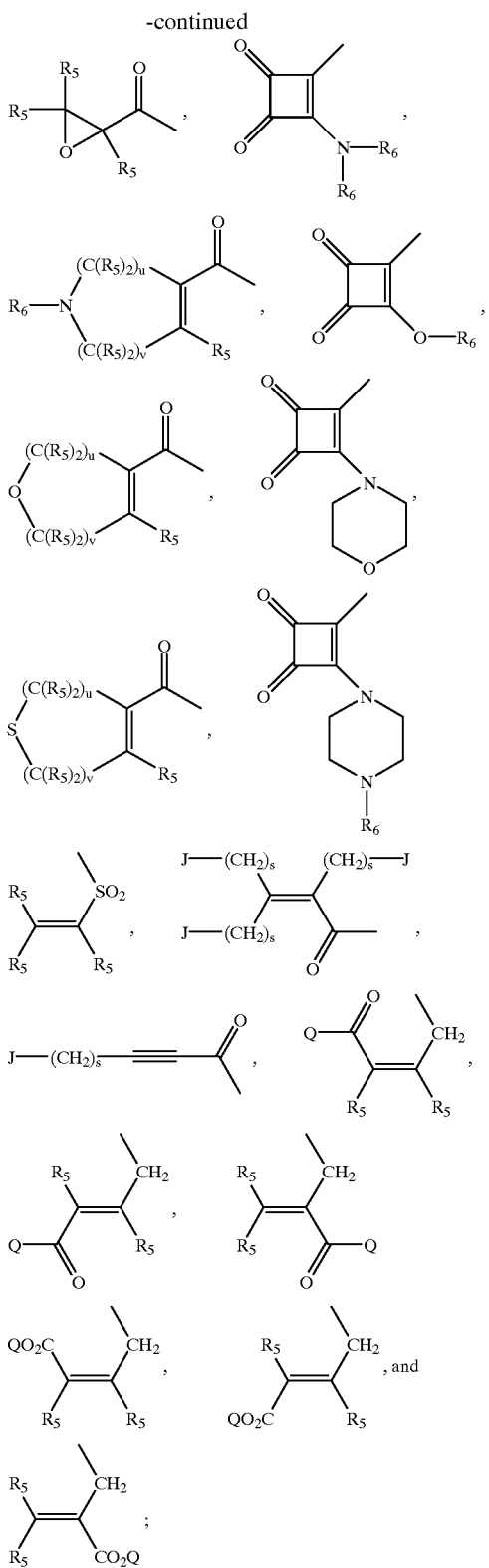

$R_7$ is —$NR_6R_6$, or —$OR_6$;
M is >$NR_6$, —O—, >N—$(C(R_6)_2)_p NR_6R_6$, or >N—$(C(R_6)_2)_p$—$OR_6$;
W is >$NR_6$, —O— or is a bond;
Het is a heterocycle, optionally mono- or di-substituted on carbon or nitrogen with $R_6$ and optionally mono- substituted on carbon with —$CH_2OR_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;

$R_2$, is selected from the group consisting of

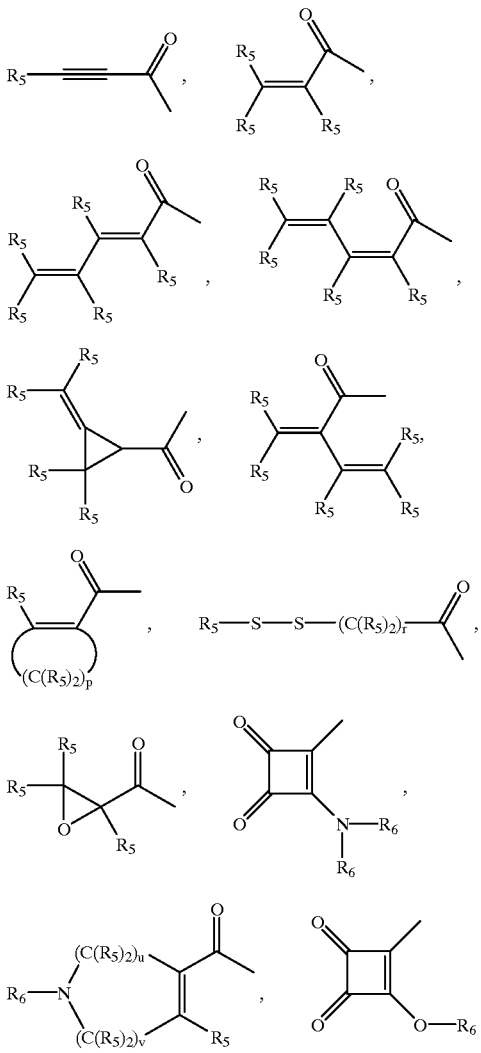

-continued

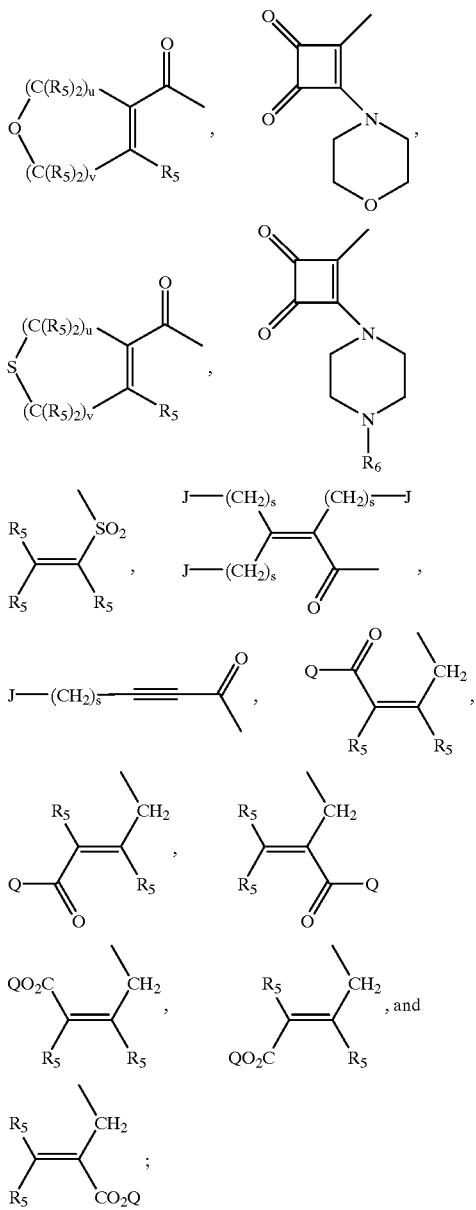

R$_5$ is independently hydrogen, alkyl of 1–6 carbon atoms, carboxy, carboalkoxy of 1–6 carbon atoms, phenyl, carboalkyl of 2–7 carbon atoms, R$_7$—(C(R$_6$)$_2$)$_s$—, R$_7$—(C(R$_6$)$_2$)$_p$—M—(C(R$_6$)$_2$)$_r$—, R$_8$R$_9$—CH—M—(C(R$_6$)$_2$)$_r$—, or Het-W—(C(R$_6$)$_2$)$_r$—;

R$_8$, and R$_9$ are each, independently, —(C(R$_6$)$_2$)$_r$NR$_6$R$_6$, or —(C(R$_6$)$_2$)$_r$OR$_6$;

J is independently hydrogen, chlorine, fluorine, or bromine;

Q is alkyl of 1–6 carbon atoms or hydrogen;

a=0 or 1;
g=1–6;
k=0–4;
n is 0–1;
p=2–4;
q=0–4;
r=1–4;
s=1–6;
u=0–4 and v=0–4, wherein the sum of u+v is 2–4;
or a pharmaceutically acceptable salt thereof,
provided that when:
  Z is NH;
  n is 0;
  R$_2$ is selected from the group consisting of

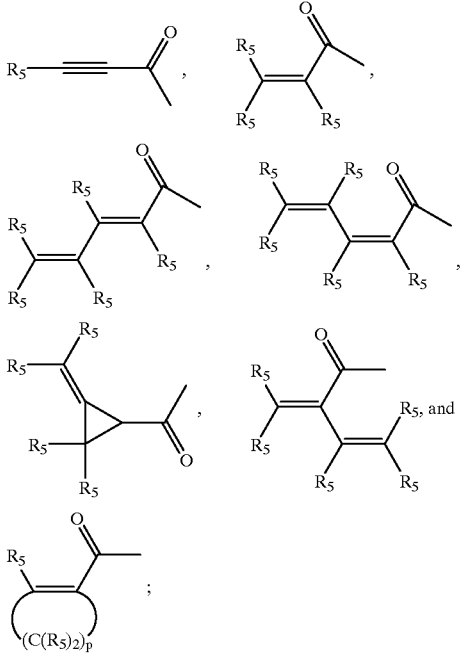

R$_5$ is independently and exclusively hydrogen, alkyl of 1–6 carbon atoms, carboxy, carboalkoxy of 1–6 carbon atoms, phenyl, or carboalkyl of 2–7 carbon atoms;

R$_1$ is hydrogen, halogen, alkyl of 1–6 carbon atoms, or alkoxy of 1–6 carbon atoms;

R$_4$ is hydrogen, halogen, alkyl of 1–6 carbon atoms, or alkoxy of 1–6 carbon atoms; and R$_3$ is hydrogen, alkyl of 1–6 carbon atoms, alkoxy of 1–6 carbon atoms, hydroxy, or trifluoromethyl;

X is not an unsubstituted phenyl ring, or a phenyl ring exclusively substituted with one or more substitutents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

further provided that when R$_2$ is

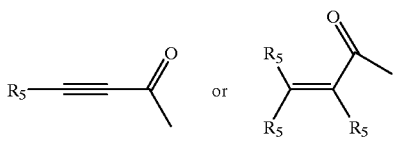

and R$_5$ is hydrogen or alkyl of 1–6 carbon atoms, R$_3$ is not halogen;

and still further provided that
  when R$_6$ is alkenyl of 2–7 carbon atoms or alkynyl of 2–7 carbon atoms, such alkenyl or alkynyl moiety is bound to a nitrogen or oxygen atom through a saturated carbon atom;
and finally provided that
when Y is —NR$_6$— or R$_7$ is —NR$_6$R$_6$ then g=2–6;
when M is —O— and R$_7$ is —OR$_6$ then p=1–4;
when Y is —NR$_6$— then k=2–4;
when Y is —O— and M or W is —O— then k=1–4
and when W is a bond with Het bonded through a nitrogen atom and Y is —O— or —NR$_6$— then k=2–4.

18. A pharmaceutical composition which comprises a compound of formula 1 having the structure

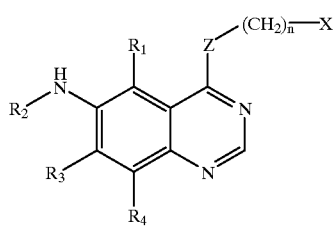

wherein:
X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;
Z is —NH—, —O—, —S—, or —NR—;
R is alkyl of 1–6 carbon atoms, or carboalkyl of 2–7 carbon atoms;
R$_1$, R$_3$, and R$_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $$R_7\text{—}(C(R_6)_2)_g\text{—}Y\text{—},\ R_7\text{—}(C(R_6)_2)_p\text{—}M\text{—}(C(R_6)_2)_k\text{—}Y\text{—},\text{ or}$$
$$\text{Het-W—}(C(R_6)_2)_k\text{—}Y\text{—}$$

Y is a divalent radical selected from the group consisting of $$\text{—}(CH_2)_a\text{—},\quad \text{—}O\text{—},\quad \text{and}\quad \text{—}\underset{R_6}{N}\text{—};$$

R$_7$ is —NR$_6$R$_6$, or —OR$_6$;
M is >NR$_6$, —O—, >N—(C(R$_6$)$_2$)$_p$NR$_6$R$_6$, or >N—(C(R$_6$)$_2$)$_p$—OR$_6$;
W is >NR$_6$, —O— or is a bond;
Het is a heterocycle, optionally mono- or di-substituted on carbon or nitrogen with R$_6$ and optionally mono-substituted on carbon with —CH$_2$OR$_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;
R$_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;
R$_2$, is selected from the group consisting of

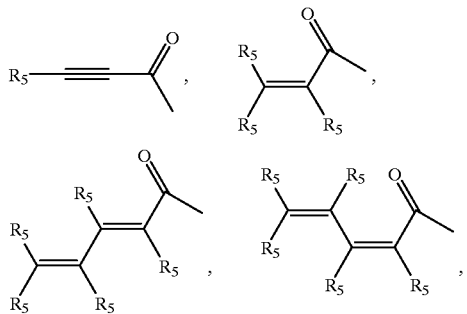

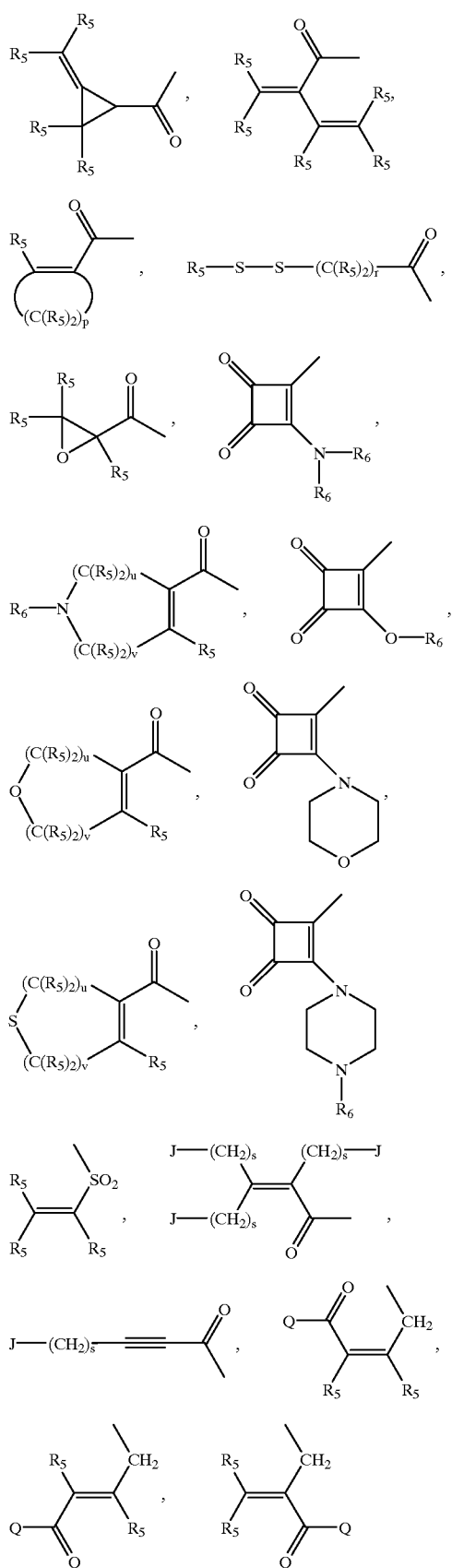
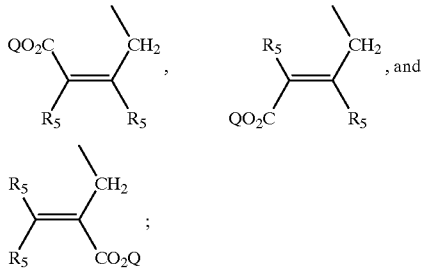
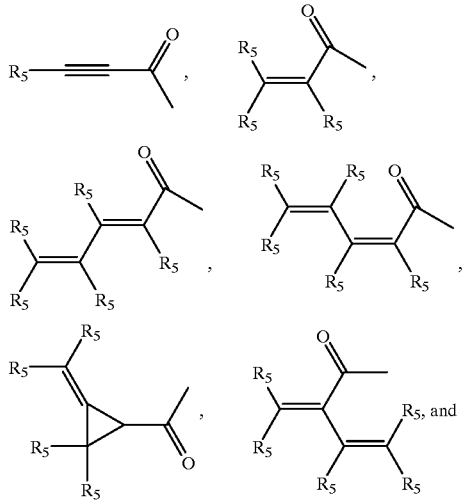

$R_5$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-W—$(C(R_6)_2)_r$—;

$R_8$, and $R_9$ are each, independently, —$(C(R_6)_2)_r NR_6R_6$, or —$(C(R_6)_2)_r OR_6$;

J is independently hydrogen, chlorine, fluorine, or bromine;

Q is alkyl of 1–6 carbon atoms or hydrogen;

a=0 or 1;

g=1–6;

k=0–4;

n is 0–1;

p=2–4;

q=0–4;

r=1–4;

s=1–6;

u=0–4 and v=0–4, wherein the sum of u+v is 2–4;

or a pharmaceutically acceptable salt thereof, provided that when:

Z is NH;

n is 0;

$R_2$ is selected from the group consisting of

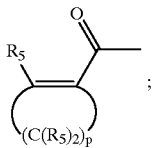

$R_5$ is independently and exclusively hydrogen, alkyl of 1–6 carbon atoms, carboxy, carboalkoxy of 1–6 carbon atoms, phenyl, or carboalkyl of 2–7 carbon atoms;

$R_1$ is hydrogen, halogen, alkyl of 1–6 carbon atoms, or alkoxy of 1–6 carbon atoms;

$R_4$ is hydrogen, halogen, alkyl of 1–6 carbon atoms, or alkoxy of 1–6 carbon atoms; and $R_3$ is hydrogen, alkyl of 1–6 carbon atoms, alkoxy of 1–6 carbon atoms, hydroxy, or trifluoromethyl;

X is not an unsubstituted phenyl ring, or a phenyl ring exclusively substituted with one or more substitutents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

further provided that when $R_2$ is

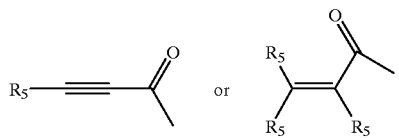

and $R_5$ is hydrogen or alkyl of 1–6 carbon atoms, $R_3$ is not halogen;

and still further provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and finally provided that when Y is —$NR_6$— or $R_7$ is —$NR_6R_6$ then g=2–6;
when M is —O— and $R_7$ is —$OR_6$ then p=1–4;
when Y is —$NR_6$— then k=2–4;
when Y is —O— and M or W is —O— then k=1–4
and when W is a bond with Het bonded through a nitrogen atom and Y is —O— or —$NR_6$— then k=2–4 and a pharmaceutical carrier.

* * * * *